(12) United States Patent
Bumann

(10) Patent No.: US 7,425,429 B2
(45) Date of Patent: Sep. 16, 2008

(54) METHOD FOR THE IDENTIFICATION OF TISSUE-SPECIFIC REGULATORY SEQUENCES

(75) Inventor: Dirk Bumann, Berlin (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 448 days.

(21) Appl. No.: 10/505,082

(22) PCT Filed: Feb. 19, 2003

(86) PCT No.: PCT/EP03/01676

§ 371 (c)(1),
(2), (4) Date: Aug. 19, 2004

(87) PCT Pub. No.: WO03/070941

PCT Pub. Date: Aug. 28, 2003

(65) Prior Publication Data

US 2005/0164962 A1    Jul. 28, 2005

Related U.S. Application Data

(60) Provisional application No. 60/394,777, filed on Jul. 5, 2002, provisional application No. 60/357,103, filed on Feb. 19, 2002.

(51) Int. Cl.
*C12P 21/02*    (2006.01)

(52) U.S. Cl. ............... 435/69.1; 435/320.1; 435/252.3; 435/252.8

(58) Field of Classification Search ....................... None
See application file for complete search history.

(56) References Cited

U.S. PATENT DOCUMENTS 5,994,077 A    11/1999    Cormack et al.
6,010,705 A *  1/2000    Thune et al. .............. 424/234.1

OTHER PUBLICATIONS

Sampson et al., Expert. Rev. vaccines, vol. 2, 2003, pp. 437-445.*
Sheela et al., Clinical and Diagnostic Laboratory Immunology, vol. 10, 2003, pp. 670-679.*
McClelland et al., "Complete genome sequence of Salmonella enterica serovar Typimurium LT2", Nature, vol. 413, No. 6858, Oct. 25, 2001, pp. 852-856.
Dunstan et al., "Use of in vivo-regulated promoters to deliver antigens from attenuated Salmonella enterica var. Typhimurium", Infection and Immunity, American Society for Microbiology, vol. 67, No. 10, Oct. 1999, pp. 5133-5141.
Bumann et al., "Regulated antigen expression in live recombinant Salmonella enterica serovar Typhimurium strongly affects colonization capabilities and specific CD4(+)-T-cell response.", Infection and Immunity. vol. 69, No. 12, Dec. 2001, pp. 7493-7500.

* cited by examiner

*Primary Examiner*—James S Ketter
(74) *Attorney, Agent, or Firm*—Rothwell Figg Ernst & Manbeck P.C.

(57) ABSTRACT

The invention relates to a method for the identification of regulatory sequences in genomes of micro-organisms, isolated ex vivo from infected tissues. The invention further relates to promoters in salmonellae identified by said method.

22 Claims, 18 Drawing Sheets

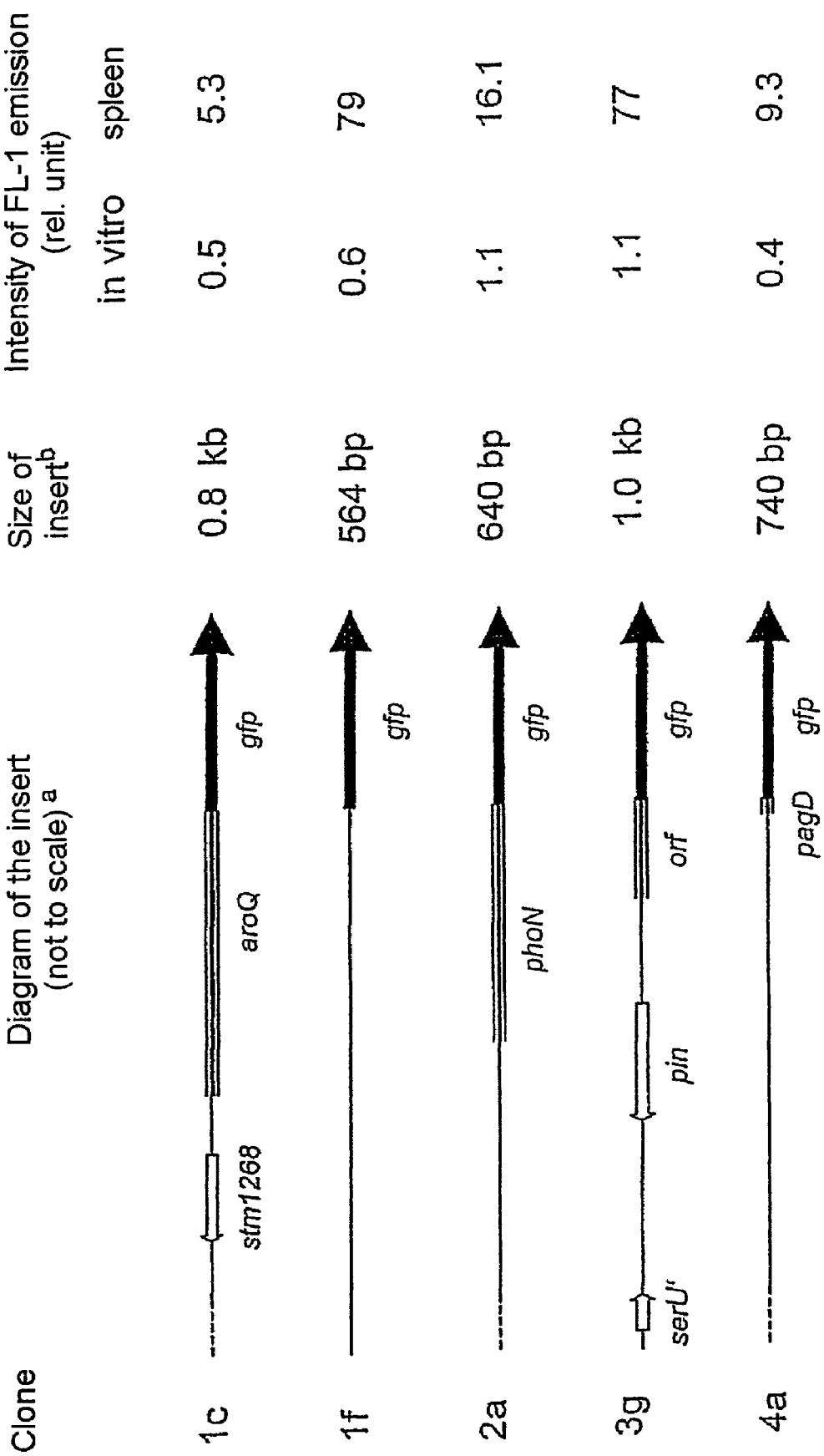

Figure 1:
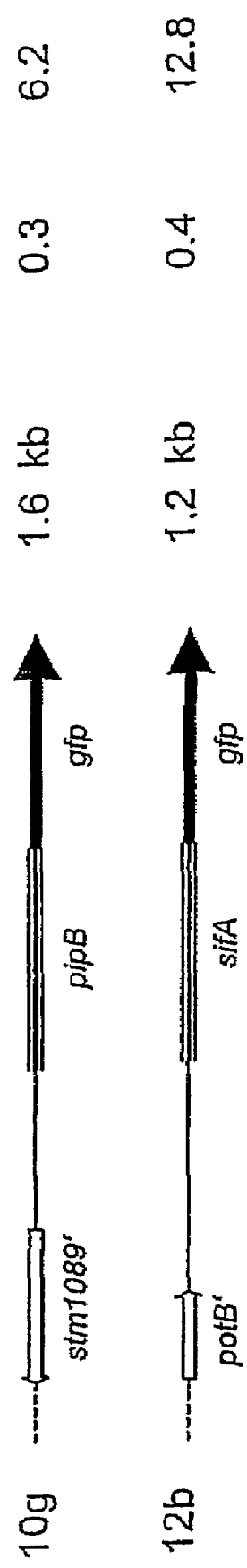

a: ORFs which are upstream of the junction site in the gfp fusion are striped. Insert regions which are adjacent to the junction site in the gfp fusion were sequenced (650-900 bp); b: size estimated on the basis of PCR products, apart from in the case of 1f, for which the complete sequence is available.

Figure 2

```
>pGFP_OVA
CCGGGGATCCTCTAGATTTAAGAAGGAGATATACATATGAGTAAAGGAGAAGAACTTTTC
ACTGGAGTTGTCCCAATTCTTGTTGAATTAGATGGTGATGTTAATGGGCACAAATTTTCT
GTCAGTGGAGAGGGTGAAGGTGATGCAACATACGGAAAACTTACCCTTAAATTTATTTGC
ACTACTGGAAAACTACCTGTTCCATGGCCAACACTTGTCACTACTTTCGCGTATGGTCTT
CAATGCTTTGCGAGATACCCAGATCATATGAAACAGCATGACTTTTTCAAGAGTGCCATG
CCCGAAGGTTATGTACAGGAAGAACTATATTTTCAAAGATGACGGGAACTACAAGACA
CGTGCTGAAGTCAAGTTTGAAGGTGATACCCTTGTTAATAGAATCGAGTTAAAAGGTATT
GATTTTAAAGAAGATGGAAACATTCTTGGACACAAATTGGAATACAACTATAACTCACAC
AATGTATACATCATGGCAGACAAACAAAGAATGGAATCAAAGTTAACTTCAAAATTAGA
CACAACATTGAAGATGGAAGCGTTCAACTAGCAGACCATTATCAACAAAATACTCCAATT
GGCGATGGCCCTGTCCTTTTACCAGACAACCATTACCTGTCCACACAATCTGCCCTTTCG
AAAGATCCCAACGAAAAGAGAGACCACATGGTCCTTCTTGAGTTTGTAACAGCTGCTGGG
ATTACACATGGCATGGATGAACTATACAAAGAATCTCTGAAAATCTCTCAGGCTGTTCAC
GCTGCTCACGCTGAAATCAACGAAGCTGGTCGTGAAGTAGTAGGTTAACTGCAGCCAAGC
TTCTGTTTTGGCGGATGAGAGAAGATTTTCAGCCTGATACAGATTAAATCAGAACGCAGA
AGCGGTCTGATAAAACAGAATTTGCCTGGCGGCAGTAGCGCGGTGGTCCCACCTGACCCC
ATGCCGAACTCAGAAGTGAAACGCCGTAGCGCCGATGGTAGTGTGGGTCTCCCCATGCG
AGAGTAGGGAACTGCCAGGCATCAAATAAAACGAAAGGCTCAGTCGAAAGACTGGGCCTT
TCGTTTTATCTGTTGTTTGTCGGTGAACGCTCTCCTGAGTAGGACAAATCCGCCGGGAGC
GGATTTGAACGTTGCGAAGCAACGGCCCGGAGGGTGGCGGGCAGGACGCCCGCCATAAAC
TGCCAGGCATCAAATTAAGCAGAAGGCCATCCTGACGGATGGCCTTTTGCGTTTCTACA
AACTCTTTTGTTTATTTTTCTAAATACATTCAAATATGTATCCGCTCATGAGACAATAAC
CCTGATAAATGCTTCAATAATATTGAAAAGGAAGAGTATGAGTATTCAACATTTCCGTG
TCGCCCTTATTCCCTTTTTTGCGGCATTTTGCCTTCCTGTTTTTGCTCACCCAGAAACGC
TGGTGAAAGTAAAAGATGCTGAAGATCAGTTGGGTGCACGAGTGGGTTACATCGAACTGG
ATCTCAACAGCGGTAAGATCCTTGAGAGTTTTCGCCCCGAAGAACGTTTTCCAATGATGA
GCACTTTTAAAGTTCTGCTATGTGGCGCGGTATTATCCCGTGTTGACGCCGGGCAAGAGC
AACTCGGTCGCCGCATACACTATTCTCAGAATGACTTGGTTGAGTACTCACCAGTCACAG
AAAAGCATCTTACGGATGGCATGACAGTAAGAGAATTATGCAGTGCTGCCATAACCATGA
GTGATAACACTGCGGCCAACTTACTTCTGACAACGATCGGAGGACCGAAGGAGCTAACCG
CTTTTTTGCACAACATGGGGGATCATGTAACTCGCCTTGATCGTTGGGAACCGGAGCTGA
ATGAAGCCATACCAAACGACGAGCGTGACACCACGATGCCTGTAGCAATGGCAACAACGT
TGCGCAAACTATTAACTGGCGAACTACTTACTCTAGCTTCCCGGCAACAATTAATAGACT
GGATGGAGGCGGATAAAGTTGCAGGACCACTTCTGCGCTCGGCCCTTCCGGCTGGCTGGT
TTATTGCTGATAAATCTGGAGCCGGTGAGCGTGGGTCTCGCGGTATCATTGCAGCACTGG
GGCCAGATGGTAAGCCCTCCCGTATCGTAGTTATCTACACGACGGGGAGTCAGGCAACTA
TGGATGAACGAAATAGACAGATCGCTGAGATAGGTGCCTCACTGATTAAGCATTGGTAAC
TGTCAGACCAAGTTTACTCATATATACTTTAGATTGATTTAAAACTTCATTTTTAATTTA
AAAGGATCTAGGTGAAGATCCTTTTGATAATCTCATGACCAAAATCCCTTAACGTGAGT
TTTCGTTCCACTGAGCGTCAGACCCCGTAGAAAGATCAAAGGATCTTCTTGAGATCCTT
TTTTTCTGCGCGTAATCTGCTGCTTGCAAACAAAAAAACCACCGCTACCAGCGGTGGTTT
GTTTGCCGGATCAAGAGCTACCAACTCTTTTTCCGAAGGTAACTGGCTTCAGCAGAGCGC
AGATACCAAATACTGTCCTTCTAGTGTAGCCGTAGTTAGGCCACCACTTCAAGAACTCTG
TAGCACCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGCAGCGGT
CGGGCTGAACGGGGGGTTCGTGCACACAGCCCAGCTTGGAGCGAACGACCTACACCGAAC
TGAGATACCTACAGCGTGAGCTATGAGAAAGCGCCACGCTTCCCGAAGGGAGAAAGGCGG
ACAGGTATCCGGTAAGCGGCAGGGTCGGAACAGGAGAGCGCACGAGGGAGCTTCCAGGGG
GAAACGCCTGGTATCTTTATAGTCCTGTCGGGTTTCGCCACCTCTGACTTGAGCGTCGAT
TTTTGTGATGCTCGTCAGGGGGCGGAGCCTATGGAAAAACGCCAGCAACGCGGCCTTTT
```

Figure 2 (continued)

```
TACGGTTCCTGGCCTTTTGCTGGCCTTTTGCTCACATGTTCTTTCCTGCGTTATCCCCTG
ATTCTGTGGATAACCGTATTACCGCCTTTGAGTGAGCTGATACCGCTCGCCGCAGCCGAA
CGACCGAGCGCAGCGAGTCAGTGAGCGAGGAAGCGGAAGAGCGCCTGATGCGGTATTTTC
TCCTTACGCATCTGTGCGGTATTTCACACCGCATATGGTGCACTCTCAGTACAATCTGCT
CTGATGCCGCATAGTTAAGCCAGTATACACTCCGCTATCGCTACGTGACTGGGTCATGGC
TGCGCCCCGACACCCGCCAACACCCGCTGACGCGCCCTGACGGGCTTGTCTGCTCCCGGC
ATCCGCTTACAGACAAGCTGTGACCGTCTCCGGGAGCTGCATGTGTCAGAGGTTTTCACC
GTCATCACCGAAACGCGCGAGGCAGCTGCGGTAAAGCTCATCAGCGTGGTCGTGAAGCGA
TTCACAGATGTCTGCCTGTTCATCCGCGTCCAGCTCGTTGAGTTTCTCCAGAAGCGTTAA
TGTCTGGCTTCTGATAAAGCGGGCCATGTTAAGGGCGGTTTTTTCCTGTTTGGTCACTTG
ATGCCTCCGTGTAAGGGGGAATTTCTGTTCATGGGGGTAATGATACCGATGAAACGAGAG
AGGATGCTCACGATACGGGTTACTGATGATGAACATGCCCGGTTACTGGAACGTTGTGAG
GGTAAACAACTGGCGGTATGGATGCGGCGGGACCAGAGAAAAATCACTCAGGGTCAATGC
CAGCGCTTCGTTAATACAGATGTAGGTGTTCCACAGGGTAGCCAGCAGCATCCTGCGATG
CAGATCCGGAACATAATGGTGCAGGGCGCTGACTTCCGCGTTTCCAGACTTTACGAAACA
CGGAAACCGAAGACCATTCATGTTGTTGCTCAGGTCGCAGACGTTTTGCAGCAGCAGTCG
CTTCACGTTCGCTCGCGTATCGGTGATTCATTCTGCTAACCAGTAAGGCAACCCCGCCAG
CCTAGCCGGGTCCTCAACGACAGGAGCACGATCATGCGCACCCGTGGCCAGGACCCAACG
CTGCCCGAGATGCGCCGCGTGCGGCTGCTGGAGATGGCGGACGCGATGGATATGTTCTGC
CAAGGGTTGGTTTGCGCATTCACAGTTCTCCGCAAGAATTGATTGGCTCCAATTCTTGGA
GTGGTGAATCCGTTAGCGAGGTGCCGCCGGCTTCCATTCAGGTCGAGGTGGCCCGGCTCC
ATGCACCGCGACGCAACGCGGGGAGGCAGACAAGGTATAGGGCGGCGCCTACAATCCATG
CCAACCCGTTCCATGTGCTCGCCGAGGCGGCATAAATCGCCGTGACGATCAGCGGTCCAG
TGATCGAAGTTAGGCTGGTAAGAGCCGCGAGCGATCCTTGAAGCTGTCCCTGATGGTCGT
CATCTACCTGCCTGGACAGCATGGCCTGCAACGCGGGCATCCCGATGCCGCCGGAAGCGA
GAAGAATCATAATGGGGAAGGCCATCCAGCCTCGCGTCGCAACGCCAGCAAGACGTAGC
CCAGCGCGTCGGCCGCCATGCCGGCGATAATGGCCTGCTTCTCGCCGAAACGTTTGGTGG
CGGGACCAGTGACGAAGGCTTGAGCGAGGGCGTGCAAGATTCCGAATACCGCAAGCGACA
GGCCGATCATCGTCGCGCTCCAGCGAAAGCGGTCCTCGCCGAAAATGACCCAGAGCGCTG
CCGGCACCTGTCCTACGAGTTGCATGATAAAGAAGACAGTCATAAGTGCGGCGACGATAG
TCATGCCCCGCGCCCACCGGAAGGAGCTGACTGGGTTGAAGGCTCTCAAGGGCATCGGTC
GACGCTCTCCCTTATGCGACTCCTGCATTAGGAAGCAGCCCAGTAGTAGGTTGAGGCCGT
TGAGCACCGCCGCCGCAAGGAATGGTGCATGCAAGGAGATGGCGCCCAACAGTCCCCGG
CCACGGGGCCTGCCACCATACCCACGCCGAAACAAGCGCTCATGAGCCCGAAGTGGCGAG
CCCGATCTTCCCCATCGGTGATGTCGGCGATATAGGCGCCAGCAACCGCACCTGTGGCGC
CGGTGATGCCGGCCACGATGCGTCCGGCGTAGAGGATCCGGAGCTTATCGACTGCACGGT
GCACCAATGCTTCTGGCGTCAGGCAGCCATCGGAAGCTGTGGTATGGCTGTGCAGGTCGT
AAATCACTGCATAATTCGTGTCGCTCAAGGCGCACTCCCGTTCTGGATAATGTTTTTTGC
GCCGACATCATAACGGTTCTGGCAAATATTCTGAAATGAGCTGTTGACAATTAATCATCG
GCTCGTATAATGTGTGGAATTGTGAGCGGATAACAATTTCACACAGGAAACAGAATTC
```

Figure 3

```
>1c
ATGGTCCGGNGNNAGATNTCCNTGAGGGGAGAGAANTAGGACNTATTAAAGTTAGNCNTA
TATCATAAANCTGTAATAAAAAATCATAAAAACGTGATGCGCATCACATTTGTGGATTTG
TTGTATATTTTATACACTTTAAATGAAGATTCCGCAGAATCAACGGCCTGTTCTTTTTC
TCACTCCAGTTTAAACGAATAAGCATTAATACCCATCTGTAATAATTACTTAATGTTATC
TTAATAAAGGTAAATTACTGTCAGGCCTCCGTAAAAGGAGGTTGATTAATGATTCGTCAT
ATCGCCATTTTTCTTTGTTCTTTATTGATGTGCAGCACCACTTTTGCCGATTCGGTAACG
TCGGTATCGCTTGGCGCGCTCTTAACCGCGCTCAATGAACGCATGTTATTAATGAAAGAT
GTGGCTGCTTATAAAATGAAGCACCATCTGCCGATAGAGGATTTCACACGTGAACAAAAT
GTTTTTGCCGAGGCTGAAGAAGAAGCGAAAAATAACGGTCTGGACCCGCATTCGATAACC
CCTTTTATTCGTTCGCTAATGGATGCCAGTAAAGCGATACAGTACCGCTATTTAGCGCAG
TGGCGAACCGGCTCAGAACCCTCCTTTCCGATACAAACCTTGTCGGTCACCCGGCAACGT
ATTCGACAACTTNATAATCAAATGTTGATC
```

Figure 4

```
>1f
GCCATTCTGACTGCAAAATGCCCCAGGATGCTGTCTTTTCGTGAATTTCACCATCTGATT
TCTTCATTTTGAGCCTCCTCGCAGGTTTTTATAATTTTATCGCCCAACTGGAAACAAAGC
CGTCAGCTAATCGTTACAACAAATATAATTAAGACAAAAACTAAAGAGTAAGATATTTAT
ATCATAAGCACTATCAGTATTGGCCTTCTGCCCTACCGCTAAACATCTCATTGTTGTTAG
CCTAATAATACTTTTAGTTTAACTTCTTATAAGACAATTTCTACACGGTTGAGCAACTAT
TTACTTTCTCTAAAAATAATATAGTGCGTAATTAATCATTACTCATAGTACATGATGATG
TGAGAATTAAGAAACCGTTTTACTTTCATTCGTTTTATCTGACATATTTCATGGCCAGG
AGGCGTGGGCATGACTAAAGCTACGGGTCGATTTGAACAATTGAACAATAATGTTGACGG
TTCAGGACAAAGCAAAATCAGGTGTTTCACCGATAGGCAAACCGATGGGCAACATGGGA
TAATATTTCGAATACCACCTATTC
```

Figure 5

```
>2a
GTAACAGAGCACATACTTTAAAATAATTATTCATACTGTGTTATTACGGAAAGATTTTAA
CCTAATGCGTGTCAGTCAGGCACGTAGATAAAAAATAATCGGGGACAAAAGTTAAACAAA
ATGCTGTTAGCCGGAAGTACCGGTATTGTTCTGTTGTCCGCTGCAGTCAGTCCGGTATGG
ACAGACGATAATGCCAGGGCAGCGTCCTGCTTTTTTACCTGTATGTTGAATAACCATTGC
AATAAATCATTATAGGATTACATCTGTTTATTATTGCCTGATCCGGAGTGAGTCTTTATG
AAAAGTCGTTATTTAGTATTTTTTCTACCACTGATCGTAGCTAAATATACATCAGCAGAA
ACAGTGCAACCCTTTCATTCTCCTGAAGAATCAGTGAACAGTCAGTTCTACTTACCACCA
CCGCCAGGTAATGATGATCCGGCTTACCGCTATGATAAGGAGGCTTATTTTAAGGGCTAT
GCGATAAAGGGTTCCCCGCGATGGAAACAAGCTGCTGAGGATGCAGATGTAAGCGTGGAA
AATATAGCCAGAATATTCTCGCCAGTAG
```

Figure 6

```
>3g
ATGAGCTAAGTGTTTGAATTGTGGCGGAGAGAGGGGGATTTGAACCCCCGGTAGAGTTGC
CCCTACTCCGGNNTTCGAGACCGTCCCAATATTCTTATTTAACATTAACTTATCTAATAA
CACGAGAAAAAAGTAGCATTTTTGTACGCAGTATTTTCAGAAAGTTAGCCTACTTATCAA
AATCATTTTCTCACCATGATAGACTATTTTTAAACAAAACCATCTCCTTTATTGACTTC
CCACAACAACATGCGCCATAACATCTTCGTGGCATCTGGTGGTTTCCGTCCTTAATCAGT
TATGGGATTCCTACAGGTTCACCGGATGCCACAACCTTCCCTCATGCTTCTAGTTAGCGC
GGTAATCCCGTTTTTAACTCCCTTCCGGGTTAGCCGATAACAGAATCCAGTACAGCCCG
TGTATCGACAGCCCCACATCATAAATAATCGCTACCTGCTGTCGCGGTATTCCTGCCCCA
ATCAGACGCCCGGCCTGCGCCCATTGCTCAGGTGATAACTTTGGTCTTCGCCCGCCAATC
TCCCCTGTCCCCCTGCAATACAATAAAAACATATCGTATAAGAAGTATAAAATACTTATT
CAAAAATGTAATTTTAAGCCCCCCTAACCAAGTAAAACTATCGTTTCAGATAGCTATG
GCACGAAAATACGGTAGCAAATCTTCATACAAAAATCTTCCAATTTATTAAACTAAGGTT
AAAACCCGATATCTTATCAATCTCAAATCATGGTATGTTATATTAATAGCGTAAGGGTTG
AAAAATGTTTTCTCGAGTCAGAGGTTTTCTTTCATGCCAGAACTATTCTCATACTGCAAC
TCCAGCTATTACTCTGCCTTCATCAGGTAGTGCAAACTTTGCCGGAGTTGAATATCCTTT
ATTGCCATTAGATC
```

Figure 7

>4a
GAAACTTGACACCGTTCGGCTAAAAACATGTCATTAAGCAAACTCGCCATATAATCAGAA
CATATCGCATTGTGCTTCACAGTCCTCACGTGACGCTCCATCCGCAATACGGTTATATGC
CATCGCAGGCGCTGTAATCATATTCACGATGATGCTTAGCACGCTTTATTCCCGCTCCGA
TTTAATCTTTTAATATATCTATCAGTTACAACATTTCTTGTTATATTATAAGAATAGAAT
CAACACCACAATTCCAACATAAATATCACCTGTGTTTAGAGAGAATTTACATTCCAAAAA
AATAATAACTAACGCAAATATTGAACACGCGATAAAAAAGTCTATTTCGCTATAAACCC
ATTATTATTAAGAGTGGTTAACTCTTCGTTGAATAAAAAATGTCAATGACGTTCCATAAT
TCAGGAGATGAACTTCACAAGTCATTATATATAACAGGAGGTGCTATGAAACA

Figure 8

>10g
TCTCTCTCATTTTGCTCTGTTGCGGNAGCATTTTAGTGGTAAGATTCCNGCTCACCAGGT
TTTACGCCATNTNCGCGCATTTATCNGGATAAGTNAAATCTGCAAAAAATATTGGGCTTA
TTATTTTTTCTTTANGTAAATTTTCGCTCAACAACTTAATTGTTTATTCAATGATGATGA
AGCGTAAGCTATGCTGGAAATGAAGGAAGTCAATAGCAAGGATAATCTTATTATTCGCGG
GTGATATTACTTCTGCTTCACCGTTATGGCAGATATCATCGCCTCTTGTCAGATGCCAGA
CACCTACTCATACTCAACCAAAGCTCTAAATACAAAAATCACCTTATATCTTTTTTATT
ATTCCTTGTATAAATGTGACTTGACTCACACCTATAAGGAGTCGGCTCACTTCCATAAGA
AGGAATCAAAATGCCAATAACTAACGCGTCCCAGAAAATATATTAAGATATTTGCATGC
GGCCGGTACCGGTACGAAAGAAGCAATGAAAGTGCAACTTCACCACGCGGTATACTGGA
ATGGTTTGTCAATTTTTTTACCTGTGGTGGAGTAAGAAGAAGCAATGAAAGATGGTTTCG
GGAGGTAATTGGAAAACTGACCACATCATTATTATATGTAAATAAAAATGCTTTCTTCGA
TGGTAATAAAATATTTCTGGAGGATGTCAACGGGTGTACTATATGTCTGTCATGGGAGCA
GCATCCGAAAATACGGATC

Figure 9

>12b
GGATTGGCCGTTTGGGCGCGGGCTACCAGGCAANNNCGCTNNCCATTGTGATGGGNCTCA
AGGNTGGTGGATTTACTGGCGGGGTTTCCCNGCTTATTAAATAAAGAAAGGTGANGTGAT
ANAAGCGGATTAATTGCGCNTCGCTAACAAAATCCGCACGGCATCCCAGGCATAAAGTTT
ATTCAAGGGGTAAACTTCCATGCNTTCGGGCATAAAAAACGCATGAAAGAAGTTGCCGCC
AGTATTGCAAATCTACAACATCATCCGCGGTAGTCCTTCTTTTATTTTTACCTGTAGCGA
CGCTATCACAGACAGTAATGCGTTTATACGCGAAGCTCTCAGGTTTATACTGATTGCCA
GTCTCTTTTAAAAATTATATTACATCCGATGCGCCCGCAGTTGAGATAAAAGGGTCGAT
TTAATCAATTATGTAGTCATTTTTACTCCAGTATAAGTGAGATTAATATGCCGATTACTA
TAGGGAATGGTTTTTAAAAAGTGAAATCCTTACCAACTCCCCAAGGAATACGAAAGAAG
CATGGTGGAAAGTTTTATGGGAAAAATTAAAGACTTCTTTTTTTCTACTGGCAAAGCAA
AAGCGGACCGTTGTCTACATGAGATGTTCTTTGCCGAACGCGCCCCACACGAGAGCGGC
TTACAGAGATTTTTTTTGAGTTGAAAGAGTTAGCCTGCGCATCGCAAAGAGATAGATTTC
AGGTTCATAATCCTCATGAAAATGATGCCACCATTATTCTTCGCATCAGGATCCTGGGTT
TGAAGGGT

Figure 10

A.2A
TCATAAAACCTGTAATAAAAATTCATAAAAACGTGATGCGCATCACATTTGGTGGATTTG
GTGGTATATTTTAANACACTTTTAAATAAAGATTCCGCAGAATCANCGGCCTGTTCTTTT
TTCTCACTCCCAGTTTAAACGAATAAGCATTAATACCCATCTGTAATAATTACTTAATGT
TATCTTAATAAAGGTAAATTACTGTCCAGCCTCCGTAAAAGGAGGTTGATTAATGATTCG
TCATATCGCCATTTTTCTTTGTTCTTTATTGATGTGCAGCACCACTTTTGCCGATTCGGT
AACGTCGGTATCGCTTGGCGCGCTCTTAACCGCGCTCAATGAACGCATGTTATTAATGAA
AGATGTGGCTGCTTATAAAATGAAGCACCATCTGCCGATAGAGGATTTCACACGTGAACA
AAATGTTTTTGCCGAGGCTGAAGAAGAAGCGAAAAATAACGGTCTGGACCCGCATTCGAT
AACCCCTTTTATTCGTTCGCTAATGGATGCCAGTAAAGCGATNCAGTACCGCTATTTAGC
GCAGTGGCGAACCGGCTCAGAACCCTCCTTTCCGATACAAACCTTGTCGGTCACCCGGCA

Figure 11

A.7A
CAAGTTACAGGATCCGCAGCAATATCAGCAAANCCCCTTATTGCTTGAAGCGATCGAGCA
GGCCGAAAATATCATCAACATTATTTATTATCGTTACCATAACAGCGCACTTGTAGTGAG
TGAGCAAGAGTAAAGTAAAAATATCTTAGAGCCTATCCCACCAGGCGTTAATTGGCGCAG
CCAGTTTGGACACGGATAGCGCGCAAAAACCGCAGCGTACACGTAGTACGTGAGGTTTGA
CTCGCTACGCTCGCCCTTCGGGCCGCCGCTAGCGGCGTTCAAAACGCTAACGCGTTTTGG
CGAGCACTGCCCAGGTTCAAAATGGCAAGTAAAATAGCCCTAATGGGATAGGCTCTTAGT
TAGCACGTTAATTATCTATCGTGTATATGGAGGGGAATGATGATAAAGAAAAAGGCTGCG
TTTAGTGAATATCGTATTTAGAGC

Figure 12

A.8H
TCGAATTATTTAGAGTATATACCATCCTTTNAAAATANTAACCNCGGGCATTGGTTTTAA
TANTACGGTTCTGGACTCATCCCACTCATTAGCAGAAAACNTATTAAAAAGCGTGTTCAG
GCATTTTATTACCGCCATTGATAAACTGTTTAACAACATCGTCTGTACAGACCTTCTTCG
TTGCCTTTACGTTTAACTCAATCAGGCTACCGTCTCGGTTATAAGTCTATCGAGTAGTAG
AGCCGTAGTATGACGATGCAGCAAAGTGATATGGAAAGATATAATCCATTATTAATGTTA
AAAGAAGTCATGGCGCAGACGCCTTATCGCCATAAACGCTGGGGAGAGCGTAAGTTTCGC
TATAAATTTTTATTACGTTGCCTTATTAACCCCGTAACGACAATTAAATACTTCAATGAA
TTATGCCATCTGTCTCAGCCCAGAACGCTGATTATTCATCG

Figure 13

A.9D
ACAGTTTATTTAATAANAATTTTTCAAATTGTAAGTTTTTATGTCAATGCTAAAAATGTA
ATTGTGATTTATCGGAAAANTCCGAATGATAGATTCGCNTGTGNCAAGGGTATATGTAGA
CAGCATCNTGATATTGTNCAAGAAGAGATAGTCGAAATAAATGTGAATCAGGCTTTTTAC
GGATGTGGTTGTGAGCGAATTTGATAGAAACTCCCATTTATGTCTGAGGAGGGATTCATG
CTGGCAGTTTTAAAAGGCATTCCATTAATTCAGGATATCAGGGCCGAAGGTAATAGCCGA
TCCTGGATAATGACTATTGATGGGCATCCTGCCAGAGGAGAAATTTTCTCAGAAGCATTT
TCTATTTCTTTGTTCTTAAATGACCTGGAAAGCTTACCTAAGCCTTGTCTTGCCTATGTG
ACACTACTGCTTGCAGCACACCCGGACGTCCATGATTATGCTATACAGCTCACAGCGGAT
GGGGGATGGTTAAACGGTTATTATACCACAAGTAGTAGCTCTGAGCTTATTGCTATTGAG
ATAGAAAACACCTGGCTTTAACTTGCATTTTAAAAAATGTAATA

Figure 14

A.10F
GCAGNAAGNCGGCAAGCGANNNAATCCCCAGGAGCTTANTAAAGTAAGTGNTGGGGTGAG
GGAACGCGNCCNCAGCACATGCAACTTGAAGTATGCGAGTATAAGCCAATATATTTATTT
GGCTGCTATTGTGTAAGCCAGACAGCAACGCGTCGTGATACGTTATTATGTAACCAGACG
TAAAGGGGGTATTCACCTTATCTCTAAATGCAAATCTATATGATAAATTTTATCATGCAC
TGTGTTGCTGTCTCTGGGAGAAAATATATGGAGCGTTCACTCGATAGTCTGGCTGGTATG
GCTAAATCTGCTTTTGGCGCGGGACTTCTGCTGCTATGCGGCAAGCTACCTCGCCCAAA
ACCATTCTGGAATATATCATTAACTTTTTTACCTGTGGTGGGATACGTCGGAGAAATGAA
ACACAATATCAGGAATTGATAGAGACTATGGCTGAGACATTGAAAAGTACAATGCCTGAC
AGAGGTGCTCCGTTGCCAGAAAACATCATCCTGGATGATATGGATGGGTGTCGTGTCGAA
TTTAATCTTCCTGGTGAGAATAACGAAGCTGGACAAGTTATTGTACGAGTCAGTAAAGGC
GACCATTCT

Figure 15

A.11B
AGATGTAGTTACNCGATAAATGTNGACGTCGATCGGGNTTCATTATTGGCTTTTGCCAGA
TCGGATTGCGCTTTGGCCAACTGCGCNTGCGCGTTAAGTTNTGCAATATGAAGGGCGTTT
TATCAATGACAAAGAGAACGTCCCCGGCGTTGACGAACTGATTATCTTTGATATTGAGTT
GGGTAATGCTGCCAGAAACCTGTGGCGTTACGCTGACCTGTTCCGCGCGGATTTTACCAT
CGCGCGTCCACGGTGACTGCATATAGTAATTCCATAACCACCACGCGGCCAGAACGGCGA
CGACGGCGACAATGAGAGTAGAAAAATATTTTATTGTTTTTAACGACATATTTACCACGC
GATCAGTAAAACGAGGCCCAGACATACGCAAAGCGTAAAGAGGGAGAGATCCATTAACAG
GGGATGCCAGATTTCATCAGAGTATATCCGGTCACGCAGGAGTCGGTGAATAAACAACCA
GATAACGAACCCAAGCGCAAAGGCTTTAAAGAATGGCGGAAAGTAAACAGATGCTCCCAA
CATGAGATCTTGTAAGGGCAATCCTGTGGCGTTGAGTATACACTTCACAAG

Figure 16

A.11H
ACTGCGTTGGGACTATGGTGTACCGCCGGCATTATATGGTTAACGTTGTATAGTCATTTT
TTAATAACCCACGTTCAACCTGTTGTTGTTTTGTGGATATCAGCACTTTTGCTTGGCCTG
GGGTATGGGGCCATTACCTGTCTTTCCCGCTTTGGCACTGTTGTCGCAACGTTGATATAT
ATTGCCATCATTACGCTTACCGGCGTGTCATTAGCTTACCTTTTCTCAGGTGGCGCGACC
ATTTTCGTGATTGTTGGAATCATGTTTAGTCTTAATGCCTTATTTATTTTCTACCTGAAT
ATCAGTTCTGGTCTATTCAGGCCGTTAATTTTTATGGCGGTAAGCGGGATCATCGCTGCG
ATAGTTGTCAATAGCCTGGTGGCCAGTAGCACTCTGGTCTGGATAGTCAGTGTGCTGACG
GTATTGGTATGGACATTGATTACAGCACTAGAAAAATCGACACTTCATGGTTATGCCCGC
ATGTTATACCACAGCGAGTTTTCATCGCTGCCTCGTTGCGCTTTATTTGGCGCGCTGACG
CTTTACCTGGCATTATTAA

Figure 17

A.12A
CTGTACAGCGTCGACAGCCCCGCATCATAAATAATCGTTACCTGCTGTCGCGGTACTCCT
GCCCTAATCAGGCGCCCGGCCTGCGCTCCCAGTGGATGGGAGCCAGTAAGGATTTGAATA
GCACATGAACTCACTCTCATATGAATTAATTTACATTGGAAAGAAAATATAATAGCGCTT
ATCATTTTTATTTAAGTTAAATATTTTATAAATGGTTTTTATTTACTCACCTGATGGTAA
TGAATAACGTTTAATATCTATAGTAAAGGATGCTGTAACCGTAAGGATAGTGTGCCAAAA
TTTAACAGGCAACGTATTATTAAACACGTTAAGAGCGTATTTTTAGCAATCATTTTAATA
TTACCATCTTCACTATATTCTGCTCTTACAATAGCGGCAGACTCTCAAGATCATAAAAAA
GAAGAAACAATTAAGCCAATGCCTCAAAAGTGGTGTAATCTTTGGCCTGCTGGCATACCC
TTCCCTGAAGATTGGTTTAAAATGTGTAGAGGTTATTNAGTATAA

Figure 18

A.12G
ATACGGCAAATTTATGNTGCATAACTCGCCCGCCAGAAATTNTGGCTCATTCATCAGCTG
GTAACGCCTCANCCGCAATACATACTGCAAGTGTATCATCCATAGCGCCCTGGTTTTACT
GTTTATGATCCGCCTCTTTTTTCGAATGGTTGGCGCCGTTTTGTTGTGGTCAGAACGAAA
ATAATTCTCAACATAATTCAGATGTGTCCAAAGAACGTTATGCGCTGTCCAGCGCCTGGC
GTCGCATTCAACGCGCAATCAGGTGTAAATCTGATGTCATTTCTAAACCCAGGCTGATTC
AATCTCTTAAATAGAGTGTGGTTTTAATCAAAAAATGAGAGCAACGGATTGGATCTTGCT
TTCGCGGTAAATAATCAAGGGAGTTATTATGCCAGTTACGTTAAGTTTTGGTAATCGTCA
TAACTATGAAATTAATCATTCACGGCTAGCCCGTTTGATGAGTCCTGATAAAGAAGAAGC
GCTATACATGGGGGTATGGGATAGATTTAAGGACTGCTTCAGAACACACAAAAAACAAGA
GGTGCTGGAGGTATTATATACACTCATCCATGGATGGAACGTGAAAATCAAGCTNAACTT
AATG

Figure 19

CLII.3A
AAGTAATCAGGTAAATGGTGTATATGGAATTACGCTTCTTTAACAGTTTTTCGTCGCCAA
TAAAATACATACAATGTTTATTGTTTTTCAACGAAGTAAATATATCATCAACAACGTGAG
GTTAATGCCTGGTACATATTATCTGACTGCTATCATTATTGAGTGTGCGCCTGGCTAAGG
CAAAGATCTAAAAAAGAAGCCACTCCTGATTTTAGTGTGCTGGCGTGAGTATGAG

Figure 20

CLII.4C
TCCAACNNCNTGATGNGCAGTTTATGNTGATACCCNATANCTGTTTTAACGACGAAGATC
AACGTGAACAAATTCTCGAAACGCTTCGTGAAGTAAAGATAAATCAGGTTTTATTCTGAT
ACCTGGCTTTCAATATTTAGGTAAATTGGCTTTCTGGCTCATCATGAGGCGTCAGGATGG
ATTGGGATCTCATTACTGAACGTAATATTCAGCTTTTTATTCAATTAGCAGGATTAGCTG
AACGGCCTTTAGCAACCAATATGTTCTGGCGGCAAGGACAATATGAAACCTATCTAAACT
ATCATAACGGTCGTATTCACTTATGTCAGATACTCAAGCAAACCTTCTTAGACGAAGAAC
TGCTTTTTAAAGCGTGGCTAACTGGA

Figure 21

CLII.9B
TTTACCGGGGCGGTANAGGTTTTACCTTGAATGCGGCGCATATAATGCGGGGTACATGAC
ACGGGCCTATAACGCATTGAATAAGTATGAANCGGAGCAGCAGTCGTTCAGGGGTTGAAC
AAACGGGCAGGTCTTTTTGTGGATTATACTGCCTCAGGTATTGCTGTCTTCCATTCCAGC
CTTAACGAATCAGGTGATTAATAACCTTAAAGACAGCACCATCGTTTTTCTTATCCAATA
TACTGAGTTTTTCGCGCGAATTCAGGAGGTTGCTGCAACCAGCTTTAAATTCTTCCATGC
TTACCTTTTTGCCGCCATAGTGTATCTTATTGGCGTTACCTTTATCGTCGGTTTGACCCG
GTTTTTAGAGCATAGACTGCTTCGCCATTACGGTCAGGGTTACTGAGTTGTACTGCACTA
TTCTGATTAATTCACCACTGACATTATCAAAGTTATTTTTATTTAGCGTTGATTAAGATT
TTAACCTTCATTATTGCGTTAGATGTCCATTCTGGTCTAAGTCTTACTCCATTGAGGATA
TTA

Figure 22

CLII.11C
TAATNTTTGCTNATTAANNANNNGNTAAAGCGNGNTTAATAAAGTAAGGAGNNCANTATG
CCATGGAGTGTTGGCAGGGTTATTTNACATCATCTATCAGTTCTGAAAAATTTAATGCGA
TAAAAGAAAGCGCACGCCNTCCGGAATTAAGTTTATGGGAGAAAATCAAAGCATATTTCT
TTACCACCCACCATGCAGAGGCGCTCGAATGTATCTTTAATCTTTACCACCATCAGGAAC
TGAATCTAACACCGGTACAGGTTCGCGGAGCCTACATCAAACTTCGAGCCTTAGCGTCTC
AGGGATGTAAAGAACAGTTTATTATAGAATCACAGGAACACGCCGATAAGTTGATTATTA
AAGATGATAATGGTGAAAATATTTTGTCTATTGAGGTTGAATGTCATCCGGAAGCTTTTG
GTCTTGCAAAAGAAATCAATAAATCACATCCCAAGCCCAAAAATATTTCTTTGGGTGATA
TTACCAGACTGGTATTTTTTGGCGACAGC

Figure 23

CLII.12C
GGTCGCTTATCGGGGTNACAGGGNGATCCTTTTTTGCTCCNGTGGNAGNACTNGGCGCAA
GTTNTGTTCACCCGTCCAGTGACGGGTNGCCCCGGGTTTTCAGTGATATATTTATGGATA
AGTGATCGGTTTTGTAAAAACTTTATTTTCCTGTCTTTNTGCTGGGTGCAGTATTTGGCA
AGCTGATTGAACTTGCTGGTTTTTACTACTCAATTGTCAGTGCTGTGACCTGTATGGTGG
GCCAGAACAAAGCCATGCCGATGATTATTCTTGTATGCGCTTTATTGACCTATGGAGGCG
TATCATTGTTTGTGGTGGCGTTTGCCAATCTGTTCTTTACTTGGCTGATTCCACATATTT
ACGGTGATCAGTTTATGATAAATCTGCCGGGGCTGAAAAAACCGCTGTAAACGGGTTAAC
CTGATGACCACGGGGAGCAGGTATTAGCATCTACGTTACAACGGTTCCGACAATATGTCT
GACCTGACCCCCTGTCAGCGGTCACCAGCGTCCTACCAGATCCGCCCCGGATCATGGTAG
GGCGGTGACACCGTCAGCCTACATTTTGTAGTTATCTCGACGTGACAGGAATTCGGATAG
GCCGAAATACTCAGTCTGACTGAGTCTATAAAAAGCAGCNCCACCTGTANTANNCGTTN
AATNNTAANCCCCAACGATGCACTTTGATATAAAAGATTTAAAA

Figure 24

3.2E
ATTATTCCTTTTATATAAATATAAAGGAAAACCCTTCCATAAACGGAAAGCTTGCCCTTGA
ACTTTNCACTGACCTGNATTAATAAACATAATCNTGCGAATATAGATGATCTCAAGAATA
AATTGAGTGAAGCCTTNCAGAAAAGANCAGTAGCACTGGTTGAGCAGATCCCTGAAAAAA
GGAAAAACAGATATCATATGCAGGAAGATGCGTTGATTGAGTTGCCGTCCGGTGAGCGTA
TTGCTATATCGAATCAATGGGGGTTAGGGACTATAGAACTGCTTATTGATTTTGTTCGTC
AGGATAATTTTGTAGTTGAAAAAGTAGGTTGACAGGAAGTAATAATAAAATAGATCCCAT
TCATTAATGGGATCTCACGTTTCATCCGATACGAAGACCATGGTCTCTTTGTCAGTAGCG
TCATAATTACGCAAGCCTCTTTACTTTGCTTATCATTTATATTAATGTAAATATTCACG
CAACACCATTAAAAAATAAGAAAAAATGGCTCACTGTTGAACTGATATTAATACCTGAAC
CACTGAATTAGAGTAATGTGGCGCTATTCATAGCGTAATTTTTTCTGTTGCGGTTACAGG
GGGAGGAATGCACACCTTTAGACCATACTCACTAAGGCATAGCGATCTGTTATATGAA

Figure 25

3.4F
GCGAGAGGATCCGCAGACAATACTGCTTTAGTGGCGCTTTATCGCTTGCCGCAAACCAGT
ACCGAAGAAGAGGCGCTCACTGGTTTTGAATTATTCATTTCAAACGTGAAGCAATTGAAA
GAGCATTATGCATAATTTAATACGTCAACATACTTTCTTAATGAGATAAAACGCGATACG
TATGCCCTTTACAAGAGACAAGACCAGAATCTTTGGTGGAAATGTAAGGGGCAAACGTTC
ATCTCTCTCATTTTGCTCTGTTTGCGGGAGCATTTTAGTGTGTAAGTATTCCTGCTCAT
CAGGTTTTTACGCCATCTACGCGCATTTATTCTGGTATAAGTTGAAATACTGCAAAAAAT
ATTGGTGCTTATTATTTTTTCTTTAAGTAAATTTTCGCTCAACAAACTTAATTGTTTATT
CAATGATGATGAAGCGTAAGCTATGCTGGAAATGAAGGAAGTCAATAGCAAGGATAATCT
TATTATTCACGGGTGATATTACTTCTGCTTCACCGTTATGGCAGATATCATCGCCTCTTG
TCAGATGCCAGACACCTACTCATACTCAACCAAAGCTCTAAATACAAAAATCACCTTATA
TCTTTTTTTATTATTCCTTGTATAAATG

Figure 26

3.6B
TCGACGCTCTCCCTTATGCGACTCCTGCATTAGGAAGCAGCCCAGTAGTAGGTTGAGGCC
GTTGAGCACCGCCGCCGCAAGGAATGGTGCATGCAAGGAGATGGCGCCCAACAGTCCCCC
GGCCACGGGGCCTGCCACCATACCCACGCCGAAACAAGCGCTCATGAGCCCGAAGTGGCG
AGCCCGATCTTCCCCATCGGTGATGTCGGCGATATAGGCGCCAGCAACCGCACCTGTGGC
GCCGGTGATGCCGGCCACGATGCGTCCGGCGTAGAGGATCAAACGTTCATCCGCATCATT
ATTCCATTAACCATGCCGGGCATTGTCGCCGGTTGCCTGCTCGTGATGCTACCGGCAATG
GGCCTGTTCTACGTCTCCGATTTAATGGGTGGCGCGAAAAACCTGCTGATTGGTAACGTC
ATTAAGGTACAGTTCCTGAATATTCGCGATTGGCCGTTTGGCGCGGCTACCAGCATTACG
CTGACCATTGTGATGGGACTCATGCTGTTGATTTACTGGCGGGCTTCCCGCTTATTGAAT
AAGAAGGTGAGTGATATAAGCGATTAATTGCGCAACGCTAACAAATCCACACGCATCCAG
GCATGAAGTTTATTCAAGGGTAAACTTCATGCCTTCGGCATAAAAAACGCATGAAAGAAG
TTGCCGCCAGTATTGCAAATCTACAACATCATCCGCGGTAGTCCTTCTTTTATTTTTACC
TGTAGCGACGCTATCACAGACAGTAATGCGTTTATACGCGAAGCTCTCAGGTTTTATACT
GATTGCCAGTCTCTTTTAAAAATTATATTACATCCGATGCGCCCGCAGTTGAGATAAAAA
GGGTCGATTTAATCAATTATGTAGTCATTTTGATC

Figure 27

3.9A
GTTTAGTCAGAATATCGAACGCGCTAAACGCATGGCCTCCCGGATTGAAACCGGGATGGT
TTATATCAACTGGCTGACCGACACCGCAGCGGAGCTGCCGTTCGGCGGCGTTAAGCGTTC
GGGCTTCGGACGCGAGCTATCGGATCTGGGGATTAAGGAGTTTGTGAACCAGAAGCTGGT
AGTGGTGCGCCGCTAATCCCTGTTGCCCCTCTGAAATCGGGAGGGGCCTGGCTTTTTGCA
GCGAAGGACGCGGATCTTAAATCAGAACGAAATAAGCGAACAAAACCCCCTCAATTGCCC
TCCTTATTTATCCACGTTGCACTAACCGTGCTTTTTATCCCGGTATTGTTTGTACAGACA
TTCATGATGCCCGCATTTTCTGTTCTATGCGGAGGCCGGTAGATC

Figure 28

3.9E
CCAAAGGGTCCGGGGTAAAGGATCGTGGTGAAGGCGCCCCGCTNGTAGCCCTGGCAGGGA
TTGGCCTTGCTATTGCCATCGCGGATGTCGCCTGTCTTATCTACCATCATAAACATCATT
TGCCTATGGCTCACGACAGTATAGGCAATGCCGTTTTTTATATTGCTAATTGTTTCGCCA
ATCAACGCAAAAGTATGGCGATTGCTAAAGCCGTCTCCCTGGGCGGTAGATTAGCCTTAA
CCGCGACGGTAATGACTCATTCATACTGGAGTGGTAGTTTGGGACTACAGCCTCATTTAT
TAGAGCGTCTTAATGATATTACCTATGGACTAATGAGTTTTACTCGCTTCGGTATGGATG
GGATGGCAATGACCGGTATGCAGGTCAGCAGCCCATTATATCGTTTGCTGGCTCAGGTAA
CGCCAGAACAACGTGCGCCGGAGTAATCGTTTTCAGGTATATACCGGATGTTCATTGCTT
TCTAAATTTTGCTATGTTGCCAGTATCCTTACGATGTATTTATTTTAAGGAAAAGCATTA
TGGATATTGCACAATTAGTGGATATGCTCTCCCACATGGCGCACCAGGCAGGCCAGGCCA
TTAATGACAAAATGAATGGTAATGATTTGCTCAACCCAGAATCGATGATTAAAGCGCAAT
TTGCCTTACAGCAGTATTGTACATTTATTAA

Figure 29

4.5G
CGCGGTCTATAAAACACAGGTGNATATTCAGCGCGGCACCATGCAGATAATCTCCATGGT
GAAGCTTGAGGGCTATGNCAAAGCAAAAATAAAGGGCTGGAAGGTACGGCATGGGATGC
GAAAAATGAGAGATTATATGCCGCAAAAGAAAGAAAACCCATTATGATCAAAGAAGTAGA
GATGAGCAAAAATGGTATCACCAGAGCGTTGCCTTCTGCCATCACTGCGAGTGTGAGCGA
TGTCTCCGGACTTGAATACCATGCCCCAACGGATTCGCTGCTGGTGTTGTCGGACGAGTC
AAAAATGATTCTTGAGGTCAGTTCCGAGTGGCGGGTGCGCGATCGATTGTTCCTGACGGC
GGAGTGGTCAGGGCTCAGAGACGATATCCCCAGCCAGAAGGGATTGCCATGGATAATGA
AAATAATTTGTATATTGTGAGTGAACCAAATCTGTTTTATAAATTTTCGTGTGATATACA
GAATGACTAAAATCTATTTTTACTGTCACAGTATGCTAAAACAGAACAAGGTTATTAATA
CCATGATTTGACGATTGTTTGATTCGTTGATTCATTGTTGGGGATATTNATGTT

Figure 30

A.2A (on top) compared with 1c

```
A.2A    1 ...........TCATAAAACCTGTAATAAAAATTCATAAAAACGTGATGC  39
                     |||:||||||||||| ||||||||||||||||||
1c     51 GTTAGNCNTATATCATAAANCTGTAATAAAAAATCATAAAAACGTGATGC 100

40 GCATCACATTTGGTGGATTTGGTGGTATATTTTAANACACTTTTAAATAA  89
          |||||||||||| ||||||||| ||    ||| |:||    ||||||| |
      101 GCATCACATTT.GTGGATTTGTTGTATATTTTATACAC...TTTAAATGA 146

90 AGATTCCGCAGAATCANCGGCCTGTTCTTTTTTCTCACTCCCAGTTTAAA 139
          |||||||||||||||:|||||||||||||||||||||| |||||||||
      147 AGATTCCGCAGAATCAACGGCCTGTTCTTTTTCTCACT.CCAGTTTAAA  195

140 CGAATAAGCATTAATACCCATCTGTAATAATTACTTAATGTTATCTTAAT 189
          ||||||||||||||||||||||||||||||||||||||||||||||||||
      196 CGAATAAGCATTAATACCCATCTGTAATAATTACTTAATGTTATCTTAAT 245

190 AAAGGTAAATTACTGTCCAGCCTCCGTAAAAGGAGGTTGATTAATGATTC 239
          ||||||||||||||||| ||||||||||||||||||||||||| ||||||
      246 AAAGGTAAATTACTGTCAGGCCTCCGTAAAAGGAGGTTGATTAATGATTC 295

240 GTCATATCGCCATTTTTCTTTGTTCTTTATTGATGTGCAGCACCACTTTT 289
          ||||||||||||||||||||||||||||||||||||||||||||||||||
      296 GTCATATCGCCATTTTTCTTTGTTCTTTATTGATGTGCAGCACCACTTTT 345

290 GCCGATTCGGTAACGTCGGTATCGCTTGGCGCGCTCTTAACCGCGCTCAA 339
          ||||||||||||||||||||||||||||||||||||||||||||||||||
      346 GCCGATTCGGTAACGTCGGTATCGCTTGGCGCGCTCTTAACCGCGCTCAA 395

340 TGAACGCATGTTATTAATGAAAGATGTGGCTGCTTATAAAATGAAGCACC 389
          ||||||||||||||||||||||||||||||||||||||||||||||||||
      396 TGAACGCATGTTATTAATGAAAGATGTGGCTGCTTATAAAATGAAGCACC 445

390 ATCTGCCGATAGAGGATTTCACACGTGAACAAAATGTTTTTGCCGAGGCT 439
          ||||||||||||||||||||||||||||||||||||||||||||||||||
      446 ATCTGCCGATAGAGGATTTCACACGTGAACAAAATGTTTTTGCCGAGGCT 495

440 GAAGAAGAAGCGAAAAATAACGGTCTGGACCCGCATTCGATAACCCCTTT 489
          ||||||||||||||||||||||||||||||||||||||||||||||||||
      496 GAAGAAGAAGCGAAAAATAACGGTCTGGACCCGCATTCGATAACCCCTTT 545

490 TATTCGTTCGCTAATGGATGCCAGTAAAGCGATNCAGTACCGCTATTTAG 539
          |||||||||||||||||||||||||||||||||:||||||||||||||||
      546 TATTCGTTCGCTAATGGATGCCAGTAAAGCGATACAGTACCGCTATTTAG 595

540 CGCAGTGGCGAACCGGCTCAGAACCCTCCTTTCCGATACAAACCTTGTCG 589
          ||||||||||||||||||||||||||||||||||||||||||||||||||
      596 CGCAGTGGCGAACCGGCTCAGAACCCTCCTTTCCGATACAAACCTTGTCG 645

590 GTCACCCGGCA.................  ................ 600
          |||||||||||
      646 GTCACCCGGCAACGTATTCGACAACTTNATAATCAAATGTTGATC    690
```

Figure 31

3.4F (on top) compared with 10g

```
201 AGACCAGAATCTTTGGTGGAAATGTAAGGGGCAAACGTTCATCTCTCTCA 250
                                         |||||||||
  1 ..........................................TCTCTCTCA 9

251 TTTTGCTCTGTTTGCGGGAGCATTTTTAGTGTGTAAGTATTCCTGCTCAT 300
    ||||||||| ||||||:|||||||   |||  |  ||||:|||||
 10 TTTTGCTCTG.TTGCGGNAGCATTTT...AGTGGTAAGATTCCNGCTCAC 55

301 CAGGTTTTTACGCCATCTACGCGCATTTATTCTGGTATAAGTTGAAATAC 350
    |||| |||||||||||:|:|||||||||||  : | ||       :|| |
 56 CAGG.TTTTACGCCATNTNCGCGCATTTATCNGGATA....AGTNAAATC 100

351 TGCAAAAAATATTGGTGCTTATTATTTTTTCTTTAAGTAAATTTTCGCTC 400
    ||||||||||||| ||||||||||||||||||||:|||||||||||||||
101 TGCAAAAAATATTGG.GCTTATTATTTTTTCTTTANGTAAATTTTCGCTC 149

401 AACAAACTTAATTGTTTATTCAATGATGATGAAGCGTAAGCTATGCTGGA 450
    ||| ||||||||||||||||||||||||||||||||||||||||||||||
150 AAC.AACTTAATTGTTTATTCAATGATGATGAAGCGTAAGCTATGCTGGA 198

451 AATGAAGGAAGTCAATAGCAAGGATAATCTTATTATTCACGGGTGATATT 500
    |||||||||||||||||||||||||||||||||||||| |||||||||||
199 AATGAAGGAAGTCAATAGCAAGGATAATCTTATTATTCGCGGGTGATATT 248

501 ACTTCTGCTTCACCGTTATGGCAGATATCATCGCCTCTTGTCAGATGCCA 550
    ||||||||||||||||||||||||||||||||||||||||||||||||||
249 ACTTCTGCTTCACCGTTATGGCAGATATCATCGCCTCTTGTCAGATGCCA 298

551 GACACCTACTCATACTCAACCAAAGCTCTAAATACAAAAATCACCTTATA 600
    ||||||||||||||||||||||||||||||||||||||||||||||||||
299 GACACCTACTCATACTCAACCAAAGCTCTAAATACAAAAATCACCTTATA 348

601 TCTTTTTTTATTATTCCTTGTATAAATG..................... 628
    |||||||||||||||||||||||||||||
349 TCTTTTTTTATTATTCCTTGTATAAATGTGACTTGACTCACACCTATAAG 398
```

Figure 32

3.6B (on top) compared with 12b

```
401 ACCTGCTGATTGGTAACGTCATTAAGGTACAGTTCCTGAATATTCGCGAT 450
                                                  |||
  1 ..............................................GGAT   4

451 TGGCCGTTTGG..CGCGGCTACCAG..CATTACGCTGACCATTGTGATGG 496
    ||||||||||    ||||||||    |:::||||::||||||||||||
  5 TGGCCGTTTGGGCGCGGGCTACCAGGCAANNNCGCTNNCCATTGTGATGG  54

497 GACTCATGCT..GTTGATTTACTGGCGGGCTT..CCCGCTTATTGAATA. 541
    |:||||  | :   || ||||||||||||| ||  ||:||||||| ||||
 55 GNCTCAAGGNTGGTGGATTTACTGGCGGGGTTTCCCNGCTTATTAAATAA 104

542 ..AGAAGGTGAGTGATATAAGC.GATTAATTGCGCAACGCTAACAAA... 585
      |||  :||||||:||||  ||||||||||||:  ||||||||||
105 AGAAAGGTGANGTGATANAAGCGGATTAATTGCGCNTCGCTAACAAAATC 154

586 TCCACACGCATCCAGGCATGAAGTTTATTCAAGGG..TAAACTTCATGCC 633
    |||     ||||||||||| ||||||||||||||||  ||  |||||:
155 CGCACGGCATCCCAGGCATAAAGTTTATTCAAGGGGTAAACTTCCATGCN 204

634 TTC.GGCATAAAAAACGCATGAAAGAAGTTGCCGCCAGTATTGCAAATCT 682
    ||| |||||||||||||||||||||||||||||||||||||||||||||
205 TTCGGGCATAAAAAACGCATGAAAGAAGTTGCCGCCAGTATTGCAAATCT 254

683 ACAACATCATCCGCGGTAGTCCTTCTTTTATTTTTACCTGTAGCGACGCT 732
    |||||||||||||||||||||||||||||||||||||||||||||||||
255 ACAACATCATCCGCGGTAGTCCTTCTTTTATTTTTACCTGTAGCGACGCT 304

733 ATCACAGACAGTAATGCGTTTATACGCGAAGCTCTCAGGTTTTATACTGA 782
    |||||||||||||||||||||||||||||||||||||||||||||||||
305 ATCACAGACAGTAATGCGTTTATACGCGAAGCTCTCAGGTTTTATACTGA 354

783 TTGCCAGTCTCTTTTAAAAATTATATTACATCCGATGCGCCCGCAGTTGA 832
    |||||||||||||||||||||||||||||||||||||||||||||||||
355 TTGCCAGTCTCTTTTAAAAATTATATTACATCCGATGCGCCCGCAGTTGA 404

833 GATAAAAAGGGTCGATTTAATCAATTATGTAGTCATTTGATC....... 875
    ||||||||||||||||||||||||||||||||||||||| |
405 GATAAAAAGGGTCGATTTAATCAATTATGTAGTCATTTTTACTCCAGTAT 454
```

Figure 33: A.11A

CGGCGAGATTGCTAAGATTTTCCGGGCGGGCTGTATCATTCGCGCTCAGTTCCTGCAGAAGAT
CACCGATGCTTACGCAGAAAACGCCGATATCGCTAACTTGCTGTTAGCGCCTTACTTCAAGAA
AATTGCTGATGAGTACCAGCAGGCGCTGCGCGATGTCGTGGCTTACGCGGTGCAGAACGGCAT
TCCGGTGCCGACATTCTCTGCGGCAGTGGCCTACTATGACAGCTATCGCGCCGCAGTACTGCC
AGCTAACTTAATTCAGGCGCAGCGTGACTACTTTGGTGCGCACACCTATAAACGTACTGATAA
AGAAGGCATTTTCCATACCGAATGGTTGGAATAATTTCTGCAAAAATGTTTAAGCCCGGTTTA
ATACCGGGCTTTTTTTTATCTCTATTCTTATTGATTTATCGCTTTTGCTTAATATTAACTTAA
TAATCTGTGTTTATCGTAATGAAGATAATCTGAATTGTTTTCGTCTGCGTTGCACTTTATATA
CTCAGGCGTTAAAACTTTAATATCTTATCAGGATGCGAAATACATCA

Figure 34: A.8B

AGGGTATTTATGTATCCTCCGGTTAATGCTTAGTTTAGCATCTTTTAGCTGACAGCGATTGCA
ACGCTAAAAAACATGTGCTAATAATCATCATGTAAAATATGTAATGAAGTAAGTATGGAGCAT
TTAATTGTTATGATCCCACCATTAAATAGATATGTTCCCGCGCTTTCAAAAAATGAATTGGTT
AAAACTGTTACCAACAGGGACATTCAGTTTACAAGTTTTAATGGAAAAGATTATCCCTTGTGC
TTTTTAGATGAGAAAACCCCTCTTCTTTTCCAGTGGTTTGAGCGGAATCCTGCTCGCTTTGGG
AAAAATGATATACCTATAATTAACACAGAGAAAAACCCCTACCTTAACAATATCATTAAAGCA
GCAACAATTGAAAAAGAACGTCTTATAGGTATTTTTGTAGATGGTGATTTTTTTCCGGGACAA
AAGGATGCTTTTTCAAAACTTGAGTATGACTATGAAAACATAAAAGTCATATATAGAAATGAT
ATTGACTTTAGTATGTACGATAAAA

Figure 35: CLI.5A

GCTTGCGAGTGAATAGCGCGGCATTAAACCGTCGCTTTCACTCATGTTATGATCAACATCTTA
ATCTTATTCCCTTCACCATAACGTCATCGATTAGCATGTTAACCATTAAATACAAGCTAAACA
TTTGTCACATTTTTATTTGGTTAAGCAAAAAAATAATACAAAATAGCATTTTCAGTAAGCTAA
GTCAGGAGTTTTGGTGAAAATACAAGAAGTTAAGCGTATATTAACCCGCTGGCAACCGTCTTC
CTTTTCCCTATACCGGGAGGTGTTTACGCAATACGGCGGTAGTATCAATATGCACCCAGATAT
TGTGGATTATTTCATGAAGCGCTATAACTGGCATTTTAAATTCTTCCACTATAAAGAAGATGA
TAAGATTAAAGGCGCCTACTTTATCTGTAATGATCAGAATATTGGTATCCTGACGCGCAGAAC
CTTCCCGC

Figure 36: 4.4G

CGATGGCGGTCATTTTGGATGAGTTTCCGCATATGGCCGGAACGGCGTCTTCGTTGGCGGGCA
CTTTCCGCTTTGGTATTGGCGCTATCGTCGGCGCGTTGCTGTCGCTGGCTACCTTTAACAGTG
CGTGGCCGATGATCTGGTCGATTGCGCTTTGCGCCGCCTGTTCCATTCTGTTTTATCTCTACG
CCAGCCGTCCCAAAAAACGGTGACGGGCGCGCTGTCCCTCAATGGCGCCGAAGAATGCGCAGG
CGGCGTTGGGGGATGCTATCCGCTACACGATGGCAAAGCCAAACGGCTTTCATAGTTGATGTA
TATCAATTACCAATTCATCATTTTCCTCCTTTATGTTTATTTTATGTAAAATCCATTTATGTA
AAAAGTCACATCATTGTAGTTAAAAAGGTTGAGTTAGATCGCAGAAACGGGTACATATAGCCC
GCCGCTATCTCCGTGTCGGTAAAACTATTTTAACTCCCGCTTGCTGTAGAGCCACTGACGGAG
AGAAGGGCGTTAGCAATCTGTTTAAGGACGGGTTGTCAATGATGTGTTAATATAAATGTAAG

Figure 37: A.1A

```
CAGTATTGATTCTGGTAAAATAAGTGACTATTAATATAGTTAACGTTTTGAAAGAATTGAAAA
AAATAAATTGCGTGCACGCGACACCGGAGACAGATTACTGACAGTACTGTACGGTGTAGTGAT
CAGGTAATATTGGCTACAGTTTACGGTAAAAGCAAAGTCCATACTTTAACTATTAATGGGAGT
ATGCTGGCCGGGCGGCTTGCGGGGCCTTCATGCTCCCACATTTACAATGTTGGTATGATTACA
TTCTCTCTATACTTTACTGTGCTAACCTTTTATCTCGTTGAGATAACGTTTAATTAAAATGCT
CTCTTTTTGATGTACATTATAAGAGGAGACATTATTCATATTTTCGAAATCAGGGCAGACGAT
ATGTATACAACCATCAGAAACACAGCGCTAGCAATGGTAGCTTGTTTTTCGTATATCGCACAT
GCCAGTACCCACCCTCCTCTTATTATCACCAGGGGAGCCGGAGGAGACGCCTCCGGAGCCACA
GTCATTCATGATAA
```

SEQUENCE LISTING

```
<160> NUMBER OF SEQ ID NOS: 52

<210> SEQ ID NO 1
<211> LENGTH: 20
<212> TYPE: DNA
<213> ORGANISM: prokaryote

<400> SEQUENCE: 1
tttaagaagg agatatacat                                              20

<210> SEQ ID NO 2
<211> LENGTH: 11
<212> TYPE: PRT
<213> ORGANISM: Artificial sequence
<220> FEATURE:
<223> OTHER INFORMATION: C-terminal sequence of green fluorescent
      protein
```

<400> SEQUENCE: 2

Ala Ala Asn Asp Glu Asn Tyr Ala Leu Ala Ala
1               5                   10

<210> SEQ ID NO 3
<211> LENGTH: 5398
<212> TYPE: DNA
<213> ORGANISM: Artificial sequence
<220> FEATURE:
<223> OTHER INFORMATION: expression vector pGFP_OVA

<400> SEQUENCE: 3

| | | | | | | |
|---|---|---|---|---|---|---|
| ccggggatcc | tctagattta | agaaggagat | atacatatga | gtaaaggaga | agaacttttc | 60 |
| actggagttg | tcccaattct | tgttgaatta | gatggtgatg | ttaatgggca | caaattttct | 120 |
| gtcagtggag | agggtgaagg | tgatgcaaca | tacggaaaac | ttacccttaa | atttatttgc | 180 |
| actactggaa | aactacctgt | tccatggcca | acacttgtca | ctactttcgc | gtatggtctt | 240 |
| caatgctttg | cgagataccc | agatcatatg | aaacagcatg | acttttcaa | gagtgccatg | 300 |
| cccgaaggtt | atgtacagga | agaactata | ttttcaaag | atgacgggaa | ctacaagaca | 360 |
| cgtgctgaag | tcaagtttga | aggtgatacc | cttgttaata | gaatcgagtt | aaaaggtatt | 420 |
| gattttaaag | aagatggaaa | cattcttgga | cacaaattgg | aatacaacta | taactcacac | 480 |
| aatgtataca | tcatggcaga | caaacaaaag | aatggaatca | aagttaactt | caaaattaga | 540 |
| cacaacattg | aagatggaag | cgttcaacta | gcagaccatt | atcaacaaaa | tactccaatt | 600 |
| ggcgatggcc | ctgtcctttt | accagacaac | cattacctgt | ccacacaatc | tgccctttcg | 660 |
| aaagatccca | acgaaaagag | agaccacatg | gtccttcttg | agtttgtaac | agctgctggg | 720 |
| attacacatg | gcatggatga | actatacaaa | gaatctctga | aaatctctca | ggctgttcac | 780 |
| gctgctcacg | ctgaaatcaa | cgaagctggt | cgtgaagtag | taggttaact | gcagccaagc | 840 |
| ttctgttttg | gcggatgaga | gaagattttc | agcctgatac | agattaaatc | agaacgcaga | 900 |
| agcggtctga | taaaacagaa | tttgcctggc | ggcagtagcg | cggtggtccc | acctgacccc | 960 |
| atgccgaact | cagaagtgaa | acgccgtagc | gccgatggta | gtgtggggtc | tccccatgcg | 1020 |
| agagtaggga | actgccaggc | atcaaataaa | acgaaaggct | cagtcgaaag | actgggcctt | 1080 |
| tcgttttatc | tgttgtttgt | cggtgaacgc | tctcctgagt | aggacaaatc | cgccgggagc | 1140 |
| ggatttgaac | gttgcgaagc | aacggcccgg | agggtggcgg | gcaggacgcc | cgccataaac | 1200 |
| tgccaggcat | caaattaagc | agaaggccat | cctgacggat | ggcctttttg | cgtttctaca | 1260 |
| aactctttg | tttattttc | taaatacatt | caaatatgta | tccgctcatg | agacaataac | 1320 |
| cctgataaat | gcttcaataa | tattgaaaaa | ggaagagtat | gagtattcaa | catttccgtg | 1380 |
| tcgcccttat | tcccttttt | gcggcatttt | gccttcctgt | ttttgctcac | ccagaaacgc | 1440 |
| tggtgaaagt | aaaagatgct | gaagatcagt | tgggtgcacg | agtgggttac | atcgaactgg | 1500 |
| atctcaacag | cggtaagatc | cttgagagtt | ttcgccccga | agaacgtttt | ccaatgatga | 1560 |
| gcactttaa | agttctgcta | tgtggcgcgg | tattatcccg | tgttgacgcc | gggcaagagc | 1620 |
| aactcggtcg | ccgcatacac | tattctcaga | atgacttggt | tgagtactca | ccagtcacag | 1680 |
| aaaagcatct | tacggatggc | atgacagtaa | gagaattatg | cagtgctgcc | ataaccatga | 1740 |
| gtgataacac | tgcggccaac | ttacttctga | caacgatcgg | aggaccgaag | gagctaaccg | 1800 |
| cttttttgca | caacatgggg | gatcatgtaa | ctcgccttga | tcgttgggaa | ccggagctga | 1860 |
| atgaagccat | accaaacgac | gagcgtgaca | ccacgatgcc | tgtagcaatg | gcaacaacgt | 1920 |

-continued

```
tgcgcaaact attaactggc gaactactta ctctagcttc ccggcaacaa ttaatagact    1980
ggatggaggc ggataaagtt gcaggaccac ttctgcgctc ggcccttccg gctggctggt    2040
ttattgctga taaatctgga gccggtgagc gtgggtctcg cggtatcatt gcagcactgg    2100
ggccagatgg taagccctcc cgtatcgtag ttatctacac gacggggagt caggcaacta    2160
tggatgaacg aaatagacag atcgctgaga taggtgcctc actgattaag cattggtaac    2220
tgtcagacca agtttactca tatatacttt agattgattt aaaacttcat ttttaattta    2280
aaaggatcta ggtgaagatc cttttttgata atctcatgac caaaatccct taacgtgagt    2340
tttcgttcca ctgagcgtca gaccccgtag aaaagatcaa aggatcttct tgagatcctt    2400 ttttttctgcg cgtaatctgc tgcttgcaaa caaaaaaacc accgctacca gcggtggttt    2460
gtttgccgga tcaagagcta ccaactcttt ttccgaaggt aactggcttc agcagagcgc    2520
agataccaaa tactgtcctt ctagtgtagc cgtagttagg ccaccacttc aagaactctg    2580
tagcaccgcc tacatacctc gctctgctaa tcctgttacc agtggctgct gccagtggcg    2640
ataagtcgtg tcttaccggg ttggactcaa gacgatagtt accggataag gcgcagcggt    2700
cgggctgaac ggggggttcg tgcacacagc ccagcttgga gcgaacgacc tacaccgaac    2760
tgagatacct acagcgtgag ctatgagaaa gcgccacgct tcccgaaggg agaaaggcgg    2820
acaggtatcc ggtaagcggc agggtcggaa caggagagcg cacgagggag cttccagggg    2880
gaaacgcctg gtatctttat agtcctgtcg ggtttcgcca cctctgactt gagcgtcgat    2940
ttttgtgatg ctcgtcaggg gggcggagcc tatggaaaaa cgccagcaac gcggcctttt    3000
tacggttcct ggccttttgc tggccttttg ctcacatgtt ctttcctgcg ttatcccctg    3060
attctgtgga taaccgtatt accgcctttg agtgagctga taccgctcgc cgcagccgaa    3120
cgaccgagcg cagcgagtca gtgagcgagg aagcggaaga gcgcctgatg cggtattttc    3180
tccttacgca tctgtgcggt atttcacacc gcatatggtg cactctcagt acaatctgct    3240
ctgatgccgc atagttaagc cagtatacac tccgctatcg ctacgtgact gggtcatggc    3300
tgcgccccga cacccgccaa cacccgctga cgcgccctga cgggcttgtc tgctcccggc    3360
atccgcttac agacaagctg tgaccgtctc cgggagctgc atgtgtcaga ggttttcacc    3420
gtcatcaccg aaacgcgcga ggcagctgcg gtaaagctca tcagcgtggt cgtgaagcga    3480
ttcacagatg tctgcctgtt catccgcgtc cagctcgttg agtttctcca gaagcgttaa    3540
tgtctggctt ctgataaagc gggccatgtt aagggcggtt ttttcctgtt tggtcacttg    3600
atgcctccgt gtaaggggga atttctgttc atgggggtaa tgataccgat gaaacgagag    3660
aggatgctca cgatacgggt tactgatgat gaacatgccc ggttactgga acgttgtgag    3720
ggtaaacaac tggcggtatg gatgcggcgg gaccagagaa aaatcactca gggtcaatgc    3780
cagcgcttcg ttaatacaga tgtaggtgtt ccacagggta gccagcagca tcctgcgatg    3840
cagatccgga acataatggt gcagggcgct gacttccgcg tttccagact ttacgaaaca    3900
cggaaaccga agaccattca tgttgttgct caggtcgcag acgttttgca gcagcagtcg    3960
cttcacgttc gctcgcgtat cggtgattca ttctgctaac cagtaaggca accccgccag    4020
cctagccggg tcctcaacga caggagcacg atcatgcgca cccgtggcca gacccaacg    4080 ctgcccgaga tgcgccgcgt gcggctgctg gagatggcgg acgcgatgga tatgttctgc    4140
caagggttgg tttgcgcatt cacagttctc cgcaagaatt gattggctcc aattcttgga    4200
gtggtgaatc cgttagcgag gtgccgccgg cttccattca ggtcgaggtg gcccggctcc    4260
atgcaccgcg acgcaacgcg gggaggcaga caaggtatag ggcggcgcct acaatccatg    4320
```

-continued

```
ccaacccgtt ccatgtgctc gccgaggcgg cataaatcgc cgtgacgatc agcggtccag    4380
tgatcgaagt taggctggta agagccgcga gcgatccttg aagctgtccc tgatggtcgt    4440
catctacctg cctggacagc atggcctgca acgcgggcat cccgatgccg ccggaagcga    4500
gaagaatcat aatggggaag gccatccagc ctcgcgtcgc gaacgccagc aagacgtagc    4560
ccagcgcgtc ggccgccatg ccggcgataa tggcctgctt ctcgccgaaa cgtttggtgg    4620
cgggaccagt gacgaaggct tgagcgaggg cgtgcaagat tccgaatacc gcaagcgaca    4680
ggccgatcat cgtcgcgctc cagcgaaagc ggtcctcgcc gaaaatgacc cagagcgctg    4740
ccggcacctg tcctacgagt tgcatgataa agaagacagt cataagtgcg gcgacgatag    4800
tcatgccccg cgcccaccgg aaggagctga ctgggttgaa ggctctcaag ggcatcggtc    4860
gacgctctcc cttatgcgac tcctgcatta ggaagcagcc cagtagtagg ttgaggccgt    4920
tgagcaccgc cgccgcaagg aatggtgcat gcaaggagat ggcgcccaac agtccccggg    4980
ccacggggcc tgccaccata cccacgccga aacaagcgct catgagcccg aagtggcgag    5040
cccgatcttc cccatcggtg atgtcggcga tataggcgcc agcaaccgca cctgtggcgc    5100
cggtgatgcc ggccacgatg cgtccggcgt agaggatccg gagcttatcg actgcacggt    5160
gcaccaatgc ttctggcgtc aggcagccat cggaagctgt ggtatggctg tgcaggtcgt    5220
aaatcactgc ataattcgtg tcgctcaagg cgcactcccg ttctggataa tgttttttgc    5280
gccgacatca taacggttct ggcaaatatt ctgaaatgag ctgttgacaa ttaatcatcg    5340
gctcgtataa tgtgtggaat tgtgagcgga taacaatttc acacaggaaa cagaattc      5398
```

<210> SEQ ID NO 4
<211> LENGTH: 690
<212> TYPE: DNA
<213> ORGANISM: Salmonella typhimurium, Salmonella typhi, Salmonella paratyphi A, Salmonella paratyphi B, Salmonella arizonae, Salmonella bongori
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

```
<220> FEATURE:
<221> NAME/KEY: misc_feature
<222> LOCATION: (673)..(673)
<223> OTHER INFORMATION: n is a, c, g, or t

<400> SEQUENCE: 4
atggtccggn gnnagatntc cntgagggga gagaantagg acntattaaa gttagncnta      60
tatcataaan ctgtaataaa aaatcataaa aacgtgatgc gcatcacatt tgtggatttg     120
ttgtatattt tatacacttt aaatgaagat tccgcagaat caacggcctg ttcttttttc     180
tcactccagt ttaaacgaat aagcattaat acccatctgt ataaattact taatgttatc     240
ttaataaagg taaattactg tcaggcctcc gtaaaaggag gttgattaat gattcgtcat     300
atcgccattt ttctttgttc tttattgatg tgcagcacca cttttgccga ttcggtaacg     360
tcggtatcgc ttggcgcgct cttaaccgcg ctcaatgaac gcatgttatt aatgaaagat     420
gtggctgctt ataaaatgaa gcaccatctg ccgatagagg atttcacacg tgaacaaaat     480 gttttgccg aggctgaaga agaagcgaaa ataacggtc tggacccgca ttcgataacc     540
ccttttattc gttcgctaat ggatgccagt aaagcgatac agtaccgcta tttagcgcag     600
tggcgaaccg gctcagaacc ctcctttccg atacaaacct tgtcggtcac ccggcaacgt     660
attcgacaac ttnataatca aatgttgatc                                       690

<210> SEQ ID NO 5
<211> LENGTH: 564
<212> TYPE: DNA
<213> ORGANISM: Salmonella typhimurium, Salmonella typhi, Salmonella
      paratyphi A, Salmonella paratyphi B

<400> SEQUENCE: 5
gccattctga ctgcaaaatg ccccaggatg ctgtcttttc gtgaatttca ccatctgatt      60
tcttcatttt gagcctcctc gcaggttttt ataatttat cgcccaactg gaaacaaagc     120
cgtcagctaa tcgttacaac aaatataatt aagacaaaaa ctaagagta agatatttat     180 atcataagca ctatcagtat tggccttctg ccctaccgct aaacatctca ttgttgttag     240
cctaataata cttttagttt aacttcttat aagcaatt ctacacggtt gagcaactat     300
ttactttctc taaaaataat atagtgcgta attaatcatt actcatagta catgatgatg     360
tgagaattaa gaaaaccgtt ttactttcat tcgttttatc tgacatattt catggccagg     420
aggcgtgggc atgactaaag ctacgggtcg atttgaacaa ttgaacaata atgttgacgg     480
ttcaggacaa agcaaaaatc aggtgtttca ccgataggca aaccgatggg caacatggga     540
taatatttcg aataccacct attc                                             564

<210> SEQ ID NO 6
<211> LENGTH: 568
<212> TYPE: DNA
<213> ORGANISM: Salmonella typhimurium, Salmonella typhi, Salmonella
      paratyphi A, Salmonella paratyphi B

<400> SEQUENCE: 6
gtaacagagc acatacttta aaataattat tcatactgtg ttattacgga aagattttaa      60
cctaatgcgt gtcagtcagg cacgtagata aaaataatc ggggacaaaa gttaaacaaa     120
atgctgttag ccggaagtac cggtattgtt ctgttgtccg ctgcagtcag tccggtatgg     180
acagacgata atgccaggc agcgtcctgc ttttttacct gtatgttgaa taaccattgc     240
aataaatcat tataggatta catctgttta ttattgcctg atccggagtg agtctttatg     300
```

| | |
|---|---|
| aaaagtcgtt atttagtatt ttttctacca ctgatcgtag ctaaatatac atcagcagaa | 360 |
| acagtgcaac cctttcattc tcctgaagaa tcagtgaaca gtcagttcta cttaccacca | 420 |
| ccgccaggta atgatgatcc ggcttaccgc tatgataagg aggcttattt taagggctat | 480 |
| gcgataaagg gttccccgcg atggaaacaa gctgctgagg atgcagatgt aagcgtggaa | 540 |
| aatatagcca gaatattctc gccagtag | 568 |

<210> SEQ ID NO 7
<211> LENGTH: 914
<212> TYPE: DNA
<213> ORGANISM: Salmonella enterica serovar Dublin
<220> FEATURE:
<221> NAME/KEY: misc_feature
<222> LOCATION: (72)..(73)
<223> OTHER INFORMATION: n is a, c, g, or t

<400> SEQUENCE: 7

| | |
|---|---|
| atgagctaag tgtttgaatt gtggcggaga gagggggatt tgaaccccccg gtagagttgc | 60 |
| ccctactccg gnnttcgaga ccgtcccaat attcttattt aacattaact tatctaataa | 120 |
| cacgagaaaa aagtagcatt tttgtacgca gtattttcag aaagttagcc tacttatcaa | 180 |
| aatcattttc tcaccatgat agactatttt ttaaacaaaa ccatctcctt tattgacttc | 240 |
| ccacaacaac atgcgccata acatcttcgt ggcatctggt ggtttccgtc cttaatcagt | 300 |
| tatgggattc ctacaggttc accggatgcc acaaccttcc ctcatgcttc tagttagcgc | 360 |
| ggtaatcccg ttttttaact cccttccggg ttagccgata acagaatcca gtacagcccg | 420 |
| tgtatcgaca gccccacatc ataaataatc gctacctgct gtcgcggtat tcctgcccca | 480 |
| atcagacgcc cggcctgcgc ccattgctca ggtgataact ttggtcttcg cccgccaatc | 540 |
| tccccctgtcc ccctgcaata caataaaaac atatcgtata agaagtataa aatacttatt | 600 |
| caaaaatgta attttaagcc cccctaacc aagtaaaaac tatcgtttca gatagctatg | 660 |
| gcacgaaaat acggtagcaa atcttcatac aaaaatcttc caatttatta aactaaggtt | 720 |
| aaaacccgat atcttatcaa tctcaaatca tggtatgtta tattaatagc gtaagggttg | 780 |
| aaaaatgttt tctcgagtca gaggttttct ttcatgccag aactattctc atactgcaac | 840 |
| tccagctatt actctgcctt catcaggtag tgcaaacttt gccggagttg aatatccttt | 900 |
| attgccatta gatc | 914 |

<210> SEQ ID NO 8
<211> LENGTH: 473
<212> TYPE: DNA
<213> ORGANISM: Salmonella typhimurium, Salmonella typhi, Salmonella
    paratyphi A, Salmonella paratyphi B, Salmonella arizonae,
    Salmonella bongori

<400> SEQUENCE: 8

| | |
|---|---|
| gaaacttgac accgttcggc taaaaacatg tcattaagca aactcgccat ataatcagaa | 60 |
| catatcgcat tgtgcttcac agtcctcacg tgacgctcca tccgcaatac ggttatatgc | 120 |
| catcgcaggc gctgtaatca tattcacgat gatgcttagc acgctttatt cccgctccga | 180 |
| tttaatctttt taatatatct atcagttaca acatttcttg ttatattata agaatagaat | 240 |
| caacaccaca attccaacat aaatatcacc tgtgtttaga gagaatttac attccaaaaa | 300 |
| aataataact aacgcaaata ttgaacacgc gataaaaaag tctatttcgc tataaaaccc | 360 |
| attattatta agagtggtta actcttcgtt gaataaaaaa tgtcaatgac gttccataat | 420 |
| tcaggagatg aacttcacaa gtcattatat ataacaggag gtgctatgaa aca | 473 |

<210> SEQ ID NO 9
<211> LENGTH: 739
<212> TYPE: DNA
<213> ORGANISM: Salmonella typhimurium, Salmonella typhi, Salmonella paratyphi A, Salmonella paratyphi B, Salmonella arizonae, Salmonella bongori
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t

<400> SEQUENCE: 9

```
tctctctcat tttgctctgt tgcggnagca ttttagtggt aagattccng ctcaccaggt      60
tttacgccat ntncgcgcat ttatcnggat aagtnaaatc tgcaaaaaat attgggctta    120
ttatttttc  tttangtaaa ttttcgctca acaacttaat tgtttattca atgatgatga    180
agcgtaagct atgctggaaa tgaaggaagt caatagcaag gataatctta ttattcgcgg    240
gtgatattac ttctgcttca ccgttatggc agatatcatc gcctcttgtc agatgccaga    300
cacctactca tactcaacca aagctctaaa tacaaaaatc accttatatc tttttttatt    360
attccttgta taaatgtgac ttgactcaca cctataagga gtcggctcac ttccataaga    420
aggaatcaaa atgccaataa ctaacgcgtc cccagaaaat atattaagat atttgcatgc    480
ggccggtacc ggtacgaaag aagcaatgaa aagtgcaact tcaccacgcg gtatactgga    540
atggtttgtc aatttttta cctgtggtgg agtaagaaga agcaatgaaa gatggtttcg    600
ggaggtaatt ggaaaactga ccacatcatt attatatgta aataaaaatg ctttcttcga    660
tggtaataaa atatttctgg aggatgtcaa cgggtgtact atatgtctgt catgggagca    720
gcatccgaaa atacggatc                                                 739
```

<210> SEQ ID NO 10
<211> LENGTH: 788
<212> TYPE: DNA
<213> ORGANISM: Salmonella typhimurium, Salmonella typhi, Salmonella paratyphi A, Salmonella paratyphi B
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t

```
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t

<400> SEQUENCE: 10
ggattggccg tttgggcgcg ggctaccagg caannncgct nnccattgtg atgggnctca      60
aggntggtgg atttactggc ggggtttccc ngcttattaa ataaagaaag gtgangtgat     120
anaagcggat taattgcgcn tcgctaacaa atccgcacg gcatcccagg cataaagttt      180
attcaagggg taaacttcca tgcnttcggg cataaaaaac gcatgaaaga agttgccgcc     240
agtattgcaa atctacaaca tcatccgcgg tagtccttct tttattttta cctgtagcga     300
cgctatcaca gacagtaatg cgtttatacg cgaagctctc aggttttata ctgattgcca     360
gtctctttta aaattatat tacatccgat gcgcccgcag ttgagataaa aagggtcgat      420
ttaatcaatt atgtagtcat ttttactcca gtataagtga gattaatatg ccgattacta     480
tagggaatgg ttttttaaaa agtgaaatcc ttaccaactc cccaaggaat acgaaagaag     540
catggtggaa agttttatgg gaaaaaatta aagacttctt tttttctact ggcaaagcaa     600
aagcggaccg ttgtctacat gagatgttgt ttgccgaacg cgcccccaca cgagagcggc     660
ttacagagat ttttttgag ttgaaagagt tagcctgcgc atcgcaaaga gatagatttc      720
aggttcataa tcctcatgaa aatgatgcca ccattattct tcgcatcagg atcctgggtt     780
tgaagggt                                                              788

<210> SEQ ID NO 11
<211> LENGTH: 600
<212> TYPE: DNA
<213> ORGANISM: Salmonella typhimurium, Salmonella typhi, Salmonella
      paratyphi A, Salmonella paratyphi B
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t
```

```
<400> SEQUENCE: 11
tcataaaacc tgtaataaaa attcataaaa acgtgatgcg catcacattt ggtggatttg      60
gtggtatatt ttaanacact tttaaataaa gattccgcag aatcancggc ctgttctttt     120
ttctcactcc cagtttaaac gaataagcat taatacccat ctgtaataat tacttaatgt     180
tatcttaata aaggtaaatt actgtccagc ctccgtaaaa ggaggttgat taatgattcg     240
tcatatcgcc atttttcttt gttctttatt gatgtgcagc accacttttg ccgattcggt     300
aacgtcggta tcgcttggcg cgctcttaac cgcgctcaat gaacgcatgt tattaatgaa     360
agatgtggct gcttataaaa tgaagcacca tctgccgata gaggatttca cacgtgaaca     420
aaatgttttt gccgaggctg aagaagaagc gaaaaataac ggtctggacc cgcattcgat     480 aaccccttt attcgttcgc taatggatgc cagtaaagcg atncagtacc gctatttagc     540
gcagtggcga accggctcag aaccctcctt tccgatacaa accttgtcgg tcacccggca     600

<210> SEQ ID NO 12
<211> LENGTH: 444
<212> TYPE: DNA
<213> ORGANISM: Salmonella typhimurium, Salmonella typhi, Salmonella
      paratyphi A, Salmonella paratyphi B
<220> FEATURE:
<221> NAME/KEY: misc_feature
<222> LOCATION: (33)..(33)
<223> OTHER INFORMATION: n is a, c, g, or t

<400> SEQUENCE: 12
caagttacag gatccgcagc aatatcagca aanccccta ttgcttgaag cgatcgagca      60
ggccgaaaat atcatcaaca ttatttatta tcgttaccat aacagcgcac ttgtagtgag     120
tgagcaagag taaagtaaaa atatcttaga gcctatccca ccaggcgtta attggcgcag     180
ccagtttgga cacggatagc gcgcaaaaac cgcagcgtac acgtagtacg tgaggtttga     240
ctcgctacgc tcgcccttcg ggccgccgct agcggcgttc aaaacgctaa cgcgttttgg     300
cgagcactgc ccaggttcaa aatggcaagt aaaatagccc taatgggata ggctcttagt     360
tagcacgtta attatctatc gtgtatatgg aggggaatga tgataaagaa aaaggctgcg     420
tttagtgaat atcgtattta gagc                                           444

<210> SEQ ID NO 13
<211> LENGTH: 461
<212> TYPE: DNA
<213> ORGANISM: Salmonella typhimurium, Salmonella typhi, Salmonella
      paratyphi A, Salmonella paratyphi B, Salmonella arizonae,
      Salmonella bongori
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
```

```
<400> SEQUENCE: 13
tcgaattatt tagagtatat accatcctt naaaatanta accncgggca ttggttttaa      60
tantacggtt ctggactcat cccactcatt agcagaaaac ntattaaaaa gcgtgttcag    120 gcatttatt accgccattg ataaactgtt taacaacatc gtctgtacag accttcttcg    180
ttgcctttac gtttaactca atcaggctac cgtctcggtt ataagtctat cgagtagtag    240
agccgtagta tgacgatgca gcaaagtgat atggaaagat ataatccatt attaatgtta    300
aaagaagtca tggcgcagac gccttatcgc cataaacgct ggggagagcg taagtttcgc    360 tataaattt tattacgttg ccttattaac cccgtaacga caattaaata cttcaatgaa    420
ttatgccatc tgtctcagcc cagaacgctg attattcatc g                        461
```

```
<210> SEQ ID NO 14
<211> LENGTH: 585
<212> TYPE: DNA
<213> ORGANISM: Salmonella typhimurium, Salmonella typhi, Salmonella
      paratyphi A, Salmonella paratyphi B, Salmonella arizonae,
      Salmonella bongori
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
```

```
<400> SEQUENCE: 14
acagtttatt taataanaat ttttcaaatt gtaagttttt atgtcaatgc taaaaatgta      60
attgtgattt atcggaaaan tccgaatgat agattcgcnt gtgncaaggg tatatgtaga    120
cagcatcntg atattgtnca agaagagata gtcgaaataa atgtgaatca ggcttttac    180 ggatgtggtt gtgagcgaat ttgatagaaa ctcccattta tgtctgagga gggattcatg    240
ctggcagttt taaaaggcat tccattaatt caggatatca gggccgaagg taatagccga    300
tcctggataa tgactattga tgggcatcct gccagaggag aaattttctc agaagcattt    360
tctatttctt tgttcttaaa tgacctggaa agcttaccta agcctgtct tgcctatgtg    420 acactactgc ttgcagcaca cccggacgtc catgattatg ctatacagct cacagcggat    480
gggggatggt taaacggtta ttataccaca agtagtagct ctgagcttat tgctattgag    540
atagaaaaac acctggctt aacttgcatt ttaaaaaatg taata                     585
```

```
<210> SEQ ID NO 15
<211> LENGTH: 609
<212> TYPE: DNA
<213> ORGANISM: Salmonella typhimurium, Salmonella typhi, Salmonella
      paratyphi A, Salmonella paratyphi B
```

```
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t

<400> SEQUENCE: 15
gcagnaagnc ggcaagcgan nnaatcccca ggagcttant aaagtaagtg ntgggtgag     60 ggaacgcgnc cncagcacat gcaacttgaa gtatgcgagt ataagccaat atatttattt    120
ggctgctatt gtgtaagcca gacagcaacg cgtcgtgata cgttattatg taaccagacg    180
taaagggggt attcacccta tctctaaatg caaatctata tgataaattt tatcatgcac    240
tgtgttgctg tctctgggag aaaatatatg gagcgttcac tcgatagtct ggctggtatg    300
gctaaatctg cttttggcgc ggggacttct gctgctatgc ggcaagctac ctcgcccaaa    360
accattctgg aatatatcat taactttttt acctgtggtg ggatacgtcg gagaaatgaa    420
acacaatatc aggaattgat agagactatg gctgagacat tgaaaagtac aatgcctgac    480
agaggtgctc cgttgccaga aaacatcatc ctggatgata tggatgggtg tcgtgtcgaa    540
tttaatcttc ctggtgagaa taacgaagct ggacaagtta ttgtacgagt cagtaaaggc    600
gaccattct                                                            609

<210> SEQ ID NO 16
<211> LENGTH: 591
<212> TYPE: DNA
<213> ORGANISM: Salmonella typhimurium, Salmonella typhi, Salmonella
      paratyphi A, Salmonella paratyphi B, Salmonella arizonae,
      Salmonella bongori, E. coli K12, E. coli O157:H7, Klebsiella
      pneumoniae
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
```

```
<220> FEATURE:
<221> NAME/KEY: misc_feature
<222> LOCATION: (101)..(101)
<223> OTHER INFORMATION: n is a, c, g, or t

<400> SEQUENCE: 16
agatgtagtt acncgataaa tgtngacgtc gatcgggntt cattattggc ttttgccaga      60
tcggattgcg ctttggccaa ctgcgcntgc gcgttaagtt ntgcaatatg aagggcgttt     120
tatcaatgac aaagagaacg tccccggcgt tgacgaactg attatctttg atattgagtt     180
gggtaatgct gccagaaacc tgtggcgtta cgctgacctg ttccgcgcgg attttaccat     240
cgcgcgtcca cggtgactgc atatagtaat tccataacca ccacgcggcc agaacggcga     300
cgacggcgac aatgagagta gaaaaatatt ttattgtttt taacgacata tttaccacgc     360
gatcagtaaa acgaggccca gacatacgca aagcgtaaag agggagagat ccattaacag     420
gggatgccag atttcatcag agtatatccg gtcacgcagg agtcggtgaa taaacaacca     480
gataacgaac ccaagcgcaa aggctttaaa gaatggcgga aagtaaacag atgctcccaa     540
catgagatct tgtaagggca atcctgtggc gttgagtata cacttcacaa g              591

<210> SEQ ID NO 17
<211> LENGTH: 559
<212> TYPE: DNA
<213> ORGANISM: Salmonella typhimurium, Salmonella paratyphi B

<400> SEQUENCE: 17
actgcgttgg gactatggtg taccgccggc attatatggt taacgttgta tagtcatttt      60
ttaataaccc acgttcaacc tgttgttgtt ttgtggatat cagcactttt gcttggcctg     120
gggtatgggg ccattacctg tctttcccgc tttggcactg ttgtcgcaac gttgatatat     180
attgccatca ttacgcttac cggcgtgtca ttagcttacc ttttctcagg tggcgcgacc     240
attttcgtga ttgttggaat catgtttagt cttaatgcct tatttatttt ctacctgaat     300
atcagttctg gtctattcag gccgttaatt tttatggcgg taagcgggat catcgctgcg     360
atagttgtca atagcctggt ggccagtagc actctggtct ggatagtcag tgtgctgacg     420
gtattggtat ggacattgat tacagcacta gaaaaatcga cacttcatgg ttatgcccgc     480
atgttatacc acagcgagtt ttcatcgctg cctcgttgcg cttatttgg cgcgctgacg      540
ctttacctgg cattattaa                                                   559

<210> SEQ ID NO 18
<211> LENGTH: 525
<212> TYPE: DNA
<213> ORGANISM: Salmonella typhimurium, Salmonella paratyphi B,
      Salmonella arizonae
<220> FEATURE:
<221> NAME/KEY: misc_feature
<222> LOCATION: (518)..(518)
<223> OTHER INFORMATION: n is a, c, g, or t

<400> SEQUENCE: 18
ctgtacagcg tcgacagccc cgcatcataa ataatcgtta cctgctgtcg cggtactcct      60
gccctaatca ggcgcccggc ctgcgctccc agtggatggg agccagtaag gatttgaata     120
gcacatgaac tcactctcat atgaattaat ttacattgga aagaaatat aatagcgctt     180
atcattttta tttaagttaa atattttata aatggttttt atttactcac ctgatggtaa     240
tgaataacgt ttaatatcta tagtaaagga tgctgtaacc gtaaggatag tgtgccaaaa     300
tttaacaggc aacgtattat taaacacgtt aagagcgtat ttttagcaat gattttaata     360
```

```
ttaccatctt cactatattc tgctcttaca atagcggcag actctcaaga tcataaaaaa    420
gaagaaacaa ttaagccaat gcctcaaaag tggtgtaatc tttggcctgc tggcataccc    480
ttccctgaag attggtttaa aatgtgtaga ggttattnag tataa                   525
```

<210> SEQ ID NO 19
<211> LENGTH: 604
<212> TYPE: DNA
<213> ORGANISM: Salmonella typhimurium, Salmonella typhi, Salmonella
      paratyphi A, Salmonella paratyphi B
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t

<400> SEQUENCE: 19

```
atacggcaaa tttatgntgc ataactcgcc cgccagaaat tntggctcat tcatcagctg     60
gtaacgcctc anccgcaata catactgcaa gtgtatcatc catagcgccc tggttttact    120
gtttatgatc cgcctctttt ttcgaatggt tggcgccgtt ttgttgtggt cagaacgaaa    180
ataattctca acataattca gatgtgtcca agaacgttta tgcgctgtcc agcgcctggc    240
gtcgcattca acgcgcaatc aggtgtaaat ctgatgtcat ttctaaaccc aggctgattc    300
aatctcttaa atagagtgtg gttttaatca aaaatgaga gcaacggatt ggatcttgct    360
ttcgcggtaa ataatcaagg gagttattat gccagttacg ttaagttttg gtaatcgtca    420
taactatgaa attaatcatt cacggctagc ccgtttgatg agtcctgata agaagaagc     480 gctatacatg ggggtatggg atagatttaa ggactgcttc agaacacaca aaaaacaaga    540
ggtgctggag gtattatata cactcatcca tggatggaac gtgaaaatca agctnaactt    600
aatg                                                                604
```

<210> SEQ ID NO 20
<211> LENGTH: 235
<212> TYPE: DNA
<213> ORGANISM: Salmonella typhimurium, Salmonella paratyphi B,
      Salmonella arizonae

<400> SEQUENCE: 20

```
aagtaatcag gtaaatggtg tatatggaat tacgcttctt taacagtttt tcgtcgccaa     60
taaaatacat acaatgttta ttgtttttca acgaagtaaa tatatcatca acaacgtgag    120
gttaatgcct ggtacatatt atctgactgc tatcattatt gagtgtgcgc ctggctaagg    180
caaagatcta aaaagaagc cactcctgat tttagtgtgc tggcgtgagt atgag          235
```

<210> SEQ ID NO 21
<211> LENGTH: 386
<212> TYPE: DNA
<213> ORGANISM: Salmonella typhimurium, Salmonella typhi, Salmonella
      paratyphi A, Salmonella paratyphi B, Salmonella arizonae,
      Salmonella bongori

```
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 21
tccaacnncn tgatgngcag tttatgntga tacccnatan ctgttttaac gacgaagatc    60
aacgtgaaca aattctcgaa acgcttcgtg aagtaaagat aaatcaggtt ttattctgat   120
acctggcttt caatatttag gtaaattggc tttctggctc atcatgaggc gtcaggatgg   180
attgggatct cattactgaa cgtaatattc agctttttat tcaattagca ggattagctg   240
aacggccttt agcaaccaat atgttctggc ggcaaggaca atatgaaacc tatctaaact   300
atcataacgg tcgtattcac ttatgtcaga tactcaagca aaccttctta gacgaagaac   360 tgcttttaa agcgtggcta actgga                                         386

<210> SEQ ID NO 22
<211> LENGTH: 543
<212> TYPE: DNA
<213> ORGANISM: Salmonella typhimurium, Salmonella typhi, Salmonella
      paratyphi B
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t

<400> SEQUENCE: 22
tttaccgggg cggtanaggt tttaccttga atgcggcgca tataatgcgg ggtacatgac    60
acgggcctat aacgcattga ataagtatga ancggagcag cagtcgttca ggggttgaac   120
aaacgggcag gtcttttgt ggattatact gcctcaggta ttgctgtctt ccattccagc   180
cttaacgaat caggtgatta ataaccttaa agacagcacc atcgttttc ttatccaata   240 tactgagttt ttcgcgcgaa ttcaggaggt tgctgcaacc agctttaaat tcttccatgc   300 ttacctttt gccgccatag tgtatcttat tggcgttacc tttatcgtcg gtttgacccg   360 gttttagag catagactgc ttcgccatta cggtcagggt tactgagttg tactgcacta   420
ttctgattaa ttcaccactg acattatcaa agttattttt atttagcgtt gattaagatt   480
ttaaccttca ttattgcgtt agatgtccat tctggtctaa gtcttactcc attgaggata   540
tta                                                                 543
```

<210> SEQ ID NO 23
<211> LENGTH: 509
<212> TYPE: DNA
<213> ORGANISM: Salmonella typhimurium, Salmonella paratyphi B,
      Salmonella arizonae
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t

<400> SEQUENCE: 23

```
taatntttgc tnattaanna nnngntaaag cgngnttaat aaagtaagga gnncantatg    60
ccatggagtg ttggcagggt tatttnacat catctatcag ttctgaaaaa tttaatgcga   120
taaaagaaag cgcacgccnt ccggaattaa gtttatggga gaaaatcaaa gcatatttct   180
ttaccaccca ccatgcagag gcgctcgaat gtatctttaa tctttaccac catcaggaac   240
tgaatctaac accggtacag gttcgcggag cctacatcaa acttcgagcc ttagcgtctc   300
agggatgtaa agaacagttt attatagaat cacaggaaca cgccgataag ttgattatta   360
aagatgataa tggtgaaaat attttgtcta ttgaggttga atgtcatccg gaagcttttg   420
gtcttgcaaa agaaatcaat aaatcacatc ccaagcccaa aaatatttct ttgggtgata   480
ttaccagact ggtattttttt ggcgacagc                                    509
```

<210> SEQ ID NO 24
<211> LENGTH: 704
<212> TYPE: DNA
<213> ORGANISM: Salmonella typhimurium, Salmonella paratyphi B,
      Salmonella arizonae

```
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (654)..(655)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (664)..(665)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t

<400> SEQUENCE: 24
ggtcgcttat cggggtnaca gggngatcct tttttgctcc ngtggnagna ctnggcgcaa      60
gttntgttca cccgtccagt gacgggtngc cccgggtttt cagtgatata tttatggata     120
agtgatcggt tttgtaaaaa ctttattttc ctgtctttnt gctgggtgca gtatttggca     180
agctgattga acttgctggt ttttactact caattgtcag tgctgtgacc tgtatggtgg     240
gccagaacaa agccatgccg atgattattc ttgtatgcgc tttattgacc tatggaggcg     300
tatcattgtt tgtggtggcg tttgccaatc tgttctttac ttggctgatt ccacatattt     360
acggtgatca gtttatgata aatctgccgg ggctgaaaaa accgctgtaa acgggttaac     420
ctgatgacca cggggagcag gtattagcat ctacgttaca acggttccga caatatgtct     480
```

-continued

| | |
|---|---|
| gacctgaccc cctgtcagcg gtcaccagcg tcctaccaga tccgcccgg atcatggtag | 540 |
| ggcggtgaca ccgtcagcct acattttgta gttatctcga cgtgacagga attcggatag | 600 |
| gccgaaatac tcagtctgac tgagtctata aaaaagcagc nccacctgta ntanncgttn | 660 |
| aatnntaanc cccaacgatg cactttgata taaaagattt aaaa | 704 |

<210> SEQ ID NO 25
<211> LENGTH: 658
<212> TYPE: DNA
<213> ORGANISM: Salmonella typhimurium, Salmonella typhi, Salmonella paratyphi A, Salmonella paratyphi B, Salmonella arizonae, Salmonella bongori
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t

<400> SEQUENCE: 25

| | |
|---|---|
| attattcctt tatataaata taaaggaaaa cccttccata aacggaaagc ttgcccttga | 60 |
| actttncact gacctgnatt aataaacata atcntgcgaa tatagatgat ctcaagaata | 120 |
| aattgagtga agccttncag aaaagancag tagcactggt tgagcagatc cctgaaaaaa | 180 |
| ggaaaaacag atatcatatg caggaagatg cgttgattga gttgccgtcc ggtgagcgta | 240 |
| ttgctatatc gaatcaatgg gggttaggga ctatagaact gcttattgat tttgttcgtc | 300 |
| aggataattt tgtagttgaa aaagtaggtt gacaggaagt aataataaaa tagatcccat | 360 |
| tcattaatgg gatctcacgt ttcatccgat acgaagacca tggtctcttt gtcagtagcg | 420 |
| tcataattac gcaagcctct ttactttgct tatcatttat atttaatgta aatattcacg | 480 |
| caacaccatt aaaaaataag aaaaaatggc tcactgttga actgatatta atacctgaac | 540 |
| cactgaatta gagtaatgtg gcgctattca tagcgtaatt ttttctgttg cggttacagg | 600 |
| gggaggaatg cacaccttta gaccatactc actaaggcat agcgatctgt tatatgaa | 658 |

<210> SEQ ID NO 26
<211> LENGTH: 628
<212> TYPE: DNA
<213> ORGANISM: Salmonella typhimurium, Salmonella typhi, Salmonella paratyphi A, Salmonella paratyphi B, Salmonella arizonae, Salmonella bongori

<400> SEQUENCE: 26

| | |
|---|---|
| gcgagaggat ccgcagacaa tactgcttta gtggcgcttt atcgcttgcc gcaaaccagt | 60 |
| accgaagaag aggcgctcac tggttttgaa ttattcattt caaacgtgaa gcaattgaaa | 120 |
| gagcattatg cataatttaa tacgtcaaca tactttctta atgagataaa acgcgatacg | 180 |
| tatgcccttt acaagagaca agaccagaat ctttggtgga aatgtaaggg gcaaacgttc | 240 |
| atctctctca ttttgctctg tttgcgggag cattttagt gtgtaagtat tcctgctcat | 300 |

```
caggttttta cgccatctac gcgcatttat tctggtataa gttgaaatac tgcaaaaaat    360
attggtgctt attattttt ctttaagtaa attttcgctc aacaaactta attgtttatt    420
caatgatgat gaagcgtaag ctatgctgga aatgaaggaa gtcaatagca aggataatct    480
tattattcac gggtgatatt acttctgctt caccgttatg gcagatatca tcgcctcttg    540
tcagatgcca gacacctact catactcaac caaagctcta aatacaaaaa tcaccttata    600 tctttttta ttattccttg tataaatg                                        628
```

```
<210> SEQ ID NO 27
<211> LENGTH: 875
<212> TYPE: DNA
<213> ORGANISM: Salmonella typhimurium, Salmonella typhi, Salmonella
      paratyphi A, Salmonella paratyphi B

<400> SEQUENCE: 27
tcgacgctct cccttatgcg actcctgcat taggaagcag cccagtagta ggttgaggcc    60
gttgagcacc gccgccgcaa ggaatggtgc atgcaaggag atggcgccca acagtccccc   120
ggccacgggg cctgccacca tacccacgcc gaaacaagcg ctcatgagcc cgaagtggcg   180
agcccgatct tccccatcgg tgatgtcggc gatataggcg ccagcaaccg cacctgtggc   240
gccggtgatg ccggccacga tgcgtccggc gtagaggatc aaacgttcat ccgcatcatt   300
attccattaa ccatgccggg cattgtcgcc ggttgcctgc tcgtgatgct accggcaatg   360
ggcctgttct acgtctccga tttaatgggt ggcgcgaaaa acctgctgat tggtaacgtc   420
attaaggtac agttcctgaa tattcgcgat tggccgtttg gcgcggctac cagcattacg   480
ctgaccattg tgatgggact catgctgttg atttactggc gggcttcccg cttattgaat   540
aagaaggtga gtgatataag cgattaattg cgcaacgcta caaatccac acgcatccag   600 gcatgaagtt tattcaaggg taaacttcat gccttcggca taaaaaacgc atgaaagaag   660
ttgccgccag tattgcaaat ctacaacatc atccgcggta gtccttcttt tattttacc    720 tgtagcgacg ctatcacaga cagtaatgcg tttatacgcg aagctctcag gttttatact   780
gattgccagt ctcttttaaa aattatatta catccgatgc gcccgcagtt gagataaaaa   840
gggtcgattt aatcaattat gtagtcattt tgatc                               875
```

```
<210> SEQ ID NO 28
<211> LENGTH: 405
<212> TYPE: DNA
<213> ORGANISM: Salmonella typhimurium, Salmonella typhi, Salmonella
      paratyphi A, Salmonella paratyphi B, Salmonella arizonae,
      Salmonella bongori

<400> SEQUENCE: 28
gtttagtcag aatatcgaac gcgctaaacg catggcctcc cggattgaaa ccgggatggt    60
ttatatcaac tggctgaccg acaccgcagc ggagctgccg ttcggcggcg ttaagcgttc   120
gggcttcgga cgcgagctat cggatctggg gattaaggag tttgtgaacc agaagctggt   180
agtggtgcgc cgctaatccc tgttgcccct ctgaaatcgg gagggcctg gcttttgca    240 gcgaaggacg cggatcttaa atcagaacga aataagcgaa caaaaccccc tcaattgccc   300
tccttattta tccacgttgc actaaccgtg ctttttatcc cggtattgtt tgtacagaca   360
ttcatgatgc ccgcatttc tgttctatgc ggaggccggt agatc                    405
```

<210> SEQ ID NO 29
<211> LENGTH: 691
<212> TYPE: DNA
<213> ORGANISM: Salmonella typhimurium, Salmonella typhi, Salmonella
      paratyphi A, Salmonella paratyphi B, Salmonella arizonae,
      Salmonella bongori
<220> FEATURE:
<221> NAME/KEY: misc_feature
<222> LOCATION: (44)..(44)
<223> OTHER INFORMATION: n is a, c, g, or t

<400> SEQUENCE: 29

```
ccaaagggtc cggggtaaag gatcgtggtg aaggcgcccc gctngtagcc ctggcaggga      60
ttggccttgc tattgccatc gcggatgtcg cctgtcttat ctaccatcat aaacatcatt     120
tgcctatggc tcacgacagt ataggcaatg ccgttttttta tattgctaat tgtttcgcca    180
atcaacgcaa aagtatggcg attgctaaag ccgtctccct gggcggtaga ttagccttaa     240
ccgcgacggt aatgactcat tcatactgga gtggtagttt gggactacag cctcatttat    300
tagagcgtct taatgatatt acctatggac taatgagttt tactcgcttc ggtatggatg     360
ggatggcaat gaccggtatg caggtcagca gcccattata tcgtttgctg gctcaggtaa     420
cgccagaaca acgtgcgccg gagtaatcgt tttcaggtat ataccggatg ttcattgctt     480
tctaaatttt gctatgttgc cagtatcctt acgatgtatt tattttaagg aaaagcatta     540
tggatattgc acaattagtg gatatgctct cccacatggc gcaccaggca ggccaggcca     600
ttaatgacaa aatgaatggt aatgatttgc tcaacccaga atcgatgatt aaagcgcaat     660
ttgccttaca gcagtattgt acatttatta a                                    691
```

<210> SEQ ID NO 30
<211> LENGTH: 594
<212> TYPE: DNA
<213> ORGANISM: Salmonella typhimurium
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t

<400> SEQUENCE: 30

```
cgcggtctat aaaacacagg tgnatattca gcgcggcacc atgcagataa tctccatggt      60
gaagcttgag ggctatgnca aagcaaaaaa taaagggctg gaaggtacgg catgggatgc     120
gaaaaatgag agattatatg ccgcaaaaga aagaaaaccc attatgatca aagaagtaga     180
gatgagcaaa aatggtatca ccagagcgtt gccttctgcc atcactgcga gtgtgagcga     240
tgtctccgga cttgaatacc atgccccaac ggattcgctg ctggtgttgt cggacgagtc     300
aaaaatgatt cttgaggtca gttccgagtg gcggtgcgc gatcgattgt tcctgacggc     360
ggagtggtca gggctcagag acgatatccc ccagccagaa gggattgcca tggataatga     420
aaataatttg tatattgtga gtgaaccaaa tctgttttat aaattttcgt gtgatataca     480
gaatgactaa aatctatttt tactgtcaca gtatgctaaa acagaacaag gttattaata     540
ccatgatttg acgattgttt gattcgttga ttcattgttg gggatattna tgtt            594
```

<210> SEQ ID NO 31
<211> LENGTH: 551
<212> TYPE: DNA
<213> ORGANISM: Salmonella typhimurium, Salmonella typhi, Salmonella paratyphi A, Salmonella paratyphi B, Salmonella arizonae, Salmonella bongori, E. coli K12, E. coli O157:H7, Klebsiella pneumoniae

<400> SEQUENCE: 31

```
cggcgagatt gctaagattt tccgggcggg ctgtatcatt cgcgctcagt tcctgcagaa    60
gatcaccgat gcttacgcag aaaacgccga tatcgctaac ttgctgttag cgccttactt   120
caagaaaatt gctgatgagt accagcaggc gctgcgcgat gtcgtggctt acgcggtgca   180
gaacggcatt ccggtgccga cattctctgc ggcagtggcc tactatgaca gctatcgcgc   240
cgcagtactg ccagctaact taattcaggc gcagcgtgac tactttggtg cgcacaccta   300
taaacgtact gataaagaag gcatttttcca taccgaatgg ttggaataat ttctgcaaaa   360
atgtttaagc ccggtttaat accgggcttt tttttatctc tattcttatt gatttatcgc   420
ttttgcttaa tattaactta ataatctgtg tttatcgtaa tgaagataat ctgaattgtt   480
tcgtctgcg ttgcacttta tatactcagg cgttaaaact taatatctt atcaggatgc     540
gaaatacatc a                                                        551
```

<210> SEQ ID NO 32
<211> LENGTH: 529
<212> TYPE: DNA
<213> ORGANISM: Salmonella typhimurium, Salmonella paratyphi B, Salmonella arizonae

<400> SEQUENCE: 32

```
agggtattta tgtatcctcc ggttaatgct tagtttagca tcttttagct gacagcgatt    60
gcaacgctaa aaacatgtg ctaataatca tcatgtaaaa tatgtaatga agtaagtatg    120
gagcatttaa ttgttatgat cccaccatta aatagatatg ttcccgcgct tcaaaaaat   180
gaattggtta aaactgttac caacagggac attcagttta caagttttaa tggaaaagat   240
tatcccttgt gcttttaga tgagaaaacc cctcttcttt tccagtggtt tgagcggaat    300
cctgctcgct ttgggaaaaa tgatatacct ataattaaca cagagaaaaa cccctaccttt   360
aacaatatca ttaaagcagc aacaattgaa aagaacgtc ttataggtat ttttgtagat    420
ggtgatttt ttccgggaca aaaggatgct ttttcaaaac ttgagtatga ctatgaaaac    480
ataaaagtca tatatagaaa tgatattgac tttagtatgt acgataaaa                529
```

<210> SEQ ID NO 33
<211> LENGTH: 449
<212> TYPE: DNA
<213> ORGANISM: Salmonella typhimurium, Salmonella typhi, Salmonella paratyphi A, Salmonella paratyphi B, Salmonella arizonae

<400> SEQUENCE: 33

```
gcttgcgagt gaatagcgcg gcattaaacc gtcgctttca ctcatgttat gatcaacatc    60
ttaatcttat tcccttcacc ataacgtcat cgattagcat gttaaccatt aaatacaagc   120
taaacatttg tcacattttt atttggttaa gcaaaaaaat aatacaaaat agcattttca   180
gtaagctaag tcaggagttt tggtgaaaat acaagaagtt aagcgtatat taacccgctg   240
gcaaccgtct tcctttccc tataccggga ggtgttacg caatacgcg gtagtatcaa      300
tatgcaccca gatattgtgg attatttcat gaagcgctat aactggcatt ttaaattctt   360
```

```
ccactataaa gaagatgata agattaaagg cgcctacttt atctgtaatg atcagaatat        420
tggtatcctg acgcgcagaa ccttcccgc                                         449

<210> SEQ ID NO 34
<211> LENGTH: 566
<212> TYPE: DNA
<213> ORGANISM: Salmonella typhimurium, Salmonella typhi, Salmonella
      paratyphi A, Salmonella paratyphi B, Salmonella arizonae,
      Salmonella bongori, E. coli K12, E. coli O157:H7, Klebsiella
      pneumoniae

<400> SEQUENCE: 34
cgatggcggt cattttggat gagtttccgc atatggccgg aacggcgtct tcgttggcgg        60
gcactttccg ctttggtatt ggcgctatcg tcggcgcgtt gctgtcgctg gctacccttta     120 acagtgcgtg gccgatgatc tggtcgattg cgctttgcgc cgcctgttcc attctgtttt     180
atctctacgc cagccgtccc aaaaaacggt gacgggcgcg ctgtccctca atggcgccga     240
agaatgcgca ggcggcgttg ggggatgcta tccgctacac gatggcaaag ccaaacggct     300
ttcatagttg atgtatatca attaccaatt catcattttc ctcctttatg tttattttat     360
gtaaaatcca tttatgtaaa aagtcacatc attgtagtta aaaaggttga gttagatcgc     420
agaaacgggt acatatagcc cgccgctatc tccgtgtcgg taaaactatt ttaactcccg     480
cttgctgtag agccactgac ggagagaagg gcgttagcaa tctgtttaag gacgggttgt     540
caatgatgtg ttaatataaa tgtaag                                           566

<210> SEQ ID NO 35
<211> LENGTH: 518
<212> TYPE: DNA
<213> ORGANISM: Salmonella typhimurium, Salmonella typhi, Salmonella
      paratyphi A, Salmonella paratyphi B

<400> SEQUENCE: 35
cagtattgat tctggtaaaa taagtgacta ttaatatagt taacgttttg aaagaattga        60
aaaaaataaa ttgcgtgcac gcgacaccgg agacagatta ctgacagtac tgtacggtgt     120
agtgatcagg taatattggc tacagtttac ggtaaaagca agtccatac tttaactatt      180 aatgggagta tgctggccgg gcggcttgcg gggccttcat gctcccacat ttacaatgtt     240
ggtatgatta cattctctct atactttact gtgctaacct tttatctcgt tgagataacg     300
tttaattaaa atgctctctt tttgatgtac attataagag gagacattat tcatattttc     360
gaaatcaggg cagacgatat gtatacaacc atcagaaaca cagcgctagc aatggtagct     420 tgttttttcgt atatcgcaca tgccagtacc cacccctcctc ttattatcac caggggagcc    480
ggaggagacg cctccggagc cacagtcatt catgataa                              518

<210> SEQ ID NO 36
<211> LENGTH: 31
<212> TYPE: DNA
<213> ORGANISM: prokaryote

<400> SEQUENCE: 36
gctctagatt taagaaggag atatacatat g                                       31

<210> SEQ ID NO 37
<211> LENGTH: 31
<212> TYPE: DNA
<213> ORGANISM: Artificial sequence
```

```
<220> FEATURE:
<223> OTHER INFORMATION: oligonucleotide primer with mutated version of
      prokaryotic Shine-Dalgarno sequence

<400> SEQUENCE: 37
gctctagatt taagaaagag atatacatat g                                  31

<210> SEQ ID NO 38
<211> LENGTH: 31
<212> TYPE: DNA
<213> ORGANISM: Artificial sequence
<220> FEATURE:
<223> OTHER INFORMATION: oligonucleotide primer with mutated version of
      prokaryotic Shine-Dalgarno sequence

<400> SEQUENCE: 38
gctctagatt taagaagcag atatacatat g                                  31

<210> SEQ ID NO 39
<211> LENGTH: 31
<212> TYPE: DNA
<213> ORGANISM: Artificial sequence
<220> FEATURE:
<223> OTHER INFORMATION: oligonucleotide primer with mutated version of
      prokaryotic Shine-Dalgarno sequence

<400> SEQUENCE: 39
gctctagatt taagagggag atatacatat g                                  31

<210> SEQ ID NO 40
<211> LENGTH: 31
<212> TYPE: DNA
<213> ORGANISM: Artificial sequence
<220> FEATURE:
<223> OTHER INFORMATION: oligonucleotide primer with mutated version of
      prokaryotic Shine-Dalgarno sequence

<400> SEQUENCE: 40
gctctagatt taagaagggg atatacatat g                                  31

<210> SEQ ID NO 41
<211> LENGTH: 31
<212> TYPE: DNA
<213> ORGANISM: Artificial sequence
<220> FEATURE:
<223> OTHER INFORMATION: oligonucleotide primer with mutated version of
      prokaryotic Shine-Dalgarno sequence

<400> SEQUENCE: 41
gctctagatt taagaaggaa atatacatat g                                  31

<210> SEQ ID NO 42
<211> LENGTH: 14
<212> TYPE: DNA
<213> ORGANISM: Artificial sequence
<220> FEATURE:
<223> OTHER INFORMATION: oligonucleotide primer with homology to GFP_OVA
      vector

<400> SEQUENCE: 42
ggccacgatg cgtc                                                     14

<210> SEQ ID NO 43
<211> LENGTH: 25
<212> TYPE: DNA
<213> ORGANISM: Artificial sequence
```

-continued

<220> FEATURE:
<223> OTHER INFORMATION: oligonucleotide primer with homology to GFP_OVA
      vector

<400> SEQUENCE: 43
tactcatatg tatatctcct tctta                                              25

<210> SEQ ID NO 44
<211> LENGTH: 20
<212> TYPE: DNA
<213> ORGANISM: prokaryote

<400> SEQUENCE: 44
tttaagaagg agatatacat                                                    20

<210> SEQ ID NO 45
<211> LENGTH: 17
<212> TYPE: DNA
<213> ORGANISM: Artificial sequence
<220> FEATURE:
<223> OTHER INFORMATION: oligonucleotide primer with homology to pGO WT

<400> SEQUENCE: 45
agtgacaagt gttggcc                                                       17

<210> SEQ ID NO 46
<211> LENGTH: 14
<212> TYPE: DNA
<213> ORGANISM: Artificial sequence
<220> FEATURE:
<223> OTHER INFORMATION: oligonucleotide primer with homology to GFP_OVA
      vector

<400> SEQUENCE: 46
ggccacgatg cgtc                                                          14

<210> SEQ ID NO 47
<211> LENGTH: 25
<212> TYPE: DNA
<213> ORGANISM: Artificial sequence
<220> FEATURE:
<223> OTHER INFORMATION: oligonucleotide primer with homology to GFP_OVA
      vector

<400> SEQUENCE: 47
tactcatatg tatatctcct tctta                                              25

<210> SEQ ID NO 48
<211> LENGTH: 640
<212> TYPE: DNA
<213> ORGANISM: Salmonella typhimurium, Salmonella typhi, Salmonella
      paratyphi A, Salmonella paratyphi B, Salmonella arizonae,
      Salmonella bongori
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t

```
<400> SEQUENCE: 48
gttagncnta tatcataaan ctgtaataaa aaatcataaa aacgtgatgc gcatcacatt      60
tgtggatttg ttgtatattt tatacacttt aaatgaagat tccgcagaat caacggcctg     120 ttctttttc tcactccagt ttaaacgaat aagcattaat acccatctgt aataattact      180
taatgttatc ttaataaagg taaattactg tcaggcctcc gtaaaaggag gttgattaat     240
gattcgtcat atcgccattt ttctttgttc tttattgatg tgcagcacca cttttgccga     300
ttcggtaacg tcggtatcgc ttggcgcgct cttaaccgcg ctcaatgaac gcatgttatt     360
aatgaaagat gtggctgctt ataaaatgaa gcaccatctg ccgatagagg atttcacacg     420
tgaacaaaat gttttgccg aggctgaaga agaagcgaaa aataacggtc tggacccgca     480
ttcgataacc cctttattc gttcgctaat ggatgccagt aaagcgatac agtaccgcta     540
tttagcgcag tggcgaaccg gctcagaacc ctcctttccg atacaaacct tgtcggtcac     600
ccggcaacgt attcgacaac ttnataatca aatgttgatc                            640

<210> SEQ ID NO 49
<211> LENGTH: 428
<212> TYPE: DNA
<213> ORGANISM: Salmonella typhimurium, Salmonella typhi, Salmonella
      paratyphi A, Salmonella paratyphi B, Salmonella arizonae,
      Salmonella bongori

<400> SEQUENCE: 49
agaccagaat ctttggtgga aatgtaaggg gcaaacgttc atctctctca ttttgctctg      60
tttgcgggag cattttagt gtgtaagtat tcctgctcat caggttttta cgccatctac     120
gcgcatttat tctggtataa gttgaaatac tgcaaaaaat attggtgctt attattttt     180 ctttaagtaa atttcgctc aacaaactta attgtttatt caatgatgat gaagcgtaag     240
ctatgctgga aatgaaggaa gtcaatagca aggataatct tattattcac gggtgatatt     300
acttctgctt caccgttatg gcagatatca tcgcctcttg tcagatgcca gacacctact     360
catactcaac caaagctcta aatacaaaaa tcaccttata tcttttttta ttattccttg     420
tataaatg                                                               428

<210> SEQ ID NO 50
<211> LENGTH: 398
<212> TYPE: DNA
<213> ORGANISM: Salmonella typhimurium, Salmonella typhi, Salmonella
      paratyphi A, Salmonella paratyphi B, Salmonella arizonae,
      Salmonella bongori
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
```

```
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t

<400> SEQUENCE: 50
tctctctcat tttgctctgt tgcggnagca ttttagtggt aagattccng ctcaccaggt    60
tttacgccat ntncgcgcat ttatcnggat aagtnaaatc tgcaaaaaat attgggctta   120 ttatttttc  tttangtaaa ttttcgctca acaacttaat tgtttattca atgatgatga   180
agcgtaagct atgctggaaa tgaaggaagt caatagcaag gataatctta ttattcgcgg   240
gtgatattac ttctgcttca ccgttatggc agatatcatc gcctcttgtc agatgccaga   300
cacctactca tactcaacca aagctctaaa tacaaaaatc accttatatc ttttttatt    360 attccttgta taaatgtgac ttgactcaca cctataag                            398

<210> SEQ ID NO 51
<211> LENGTH: 475
<212> TYPE: DNA
<213> ORGANISM: Salmonella typhimurium, Salmonella typhi, Salmonella
      paratyphi A, Salmonella paratyphi B

<400> SEQUENCE: 51
acctgctgat tggtaacgtc attaaggtac agttcctgaa tattcgcgat tggccgtttg    60
gcgcggctac cagcattacg ctgaccattg tgatgggact catgctgttg atttactggc   120
gggcttcccg cttattgaat aagaaggtga gtgatataag cgattaattg cgcaacgcta   180
acaaatccac acgcatccag gcatgaagtt tattcaaggg taaacttcat gccttcggca   240 taaaaacgc  atgaaagaag ttgccgccag tattgcaaat ctacaacatc atccgcggta   300
gtccttcttt tattttacc  tgtagcgacg ctatcacaga cagtaatgcg tttatacgcg   360
aagctctcag gttttatact gattgccagt ctcttttaaa aattatatta catccgatgc   420
gcccgcagtt gagataaaaa gggtcgattt aatcaattat gtagtcattt tgatc        475

<210> SEQ ID NO 52
<211> LENGTH: 454
<212> TYPE: DNA
<213> ORGANISM: Salmonella typhimurium, Salmonella typhi, Salmonella
      paratyphi A, Salmonella paratyphi B
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
```

-continued

```
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t

<400> SEQUENCE: 52
ggattggccg tttgggcgcg ggctaccagg caannncgct nnccattgtg atgggnctca        60
aggntggtgg atttactggc ggggtttccc ngcttattaa ataaagaaag gtgangtgat       120
anaagcggat taattgcgcn tcgctaacaa aatccgcacg gcatcccagg cataaagttt       180
attcaagggg taaacttcca tgcnttcggg cataaaaaac gcatgaaaga agttgccgcc       240
agtattgcaa atctacaaca tcatccgcgg tagtccttct tttatttta  cctgtagcga       300 cgctatcaca gacagtaatg cgtttatacg cgaagctctc aggttttata ctgattgcca       360
gtctctttta aaaattatat tacatccgat gcgcccgcag ttgagataaa aagggtcgat       420
ttaatcaatt atgtagtcat ttttactcca gtat                                  454
```

US 7,425,429 B2

METHOD FOR THE IDENTIFICATION OF TISSUE-SPECIFIC REGULATORY SEQUENCES

CROSS REFERENCE TO RELATED APPLICATION

This application is a 35 USC § 371 National Phase Entry Application from PCT/EP03/01676, filed Feb. 19, 2003, and designating the U.S., which claims the benefit of Provisional Application Nos. 60/357,103 filed Feb. 19, 2002 and 60/394,777 filed Jul. 5, 2002.

DESCRIPTION

The present invention relates to a method for identifying regulatory sequences in the genome of microorganisms which are isolated from infected tissue ex vivo. The invention furthermore relates to promoters which are identified in *salmonellas* using this method.

DEFINITIONS

"Regulatory sequences" are understood as being those sequences which influence the expression strength of a gene product (protein). Examples of such regulatory sequences are sequences, such as promoters and binding sites for regulatory proteins, which are arranged 5'-primed of the structural gene encoding the gene product or sequences, such as terminators, which are arranged 3'-primed of the structural gene.

"Strong expression" is understood as meaning expression at a strength of more than 25 000 copies of a protein which are simultaneously present per cell (bacterium). "Weak expression" is understood as meaning expression at a strength of fewer than 4500 copies of the protein which are present simultaneously per cell (bacterium). Expression of from 4500 to 25 000 copies is described as being moderate expression.

Examples of factors which exert an influence on the strength of expression are the properties of the promoter, in particular the strength of the promoter, the properties of the Shine-Dalgarno sequence and the half-life of the protein inside the cell.

A promoter is described as being weak (medium-strength, strong) if, under given physiological conditions, it is able to bring about a weak (moderate, strong) expression of a protein.

The Shine-Dalgarno sequence in prokaryotes is a sequence which is located 1 to 20 nucleotides upstream of the start codon and is essential for initiating translation. The sequence TTTAAGAAGGAGATATACAT [SEQ ID NO: 1] originates from gene 10 of phage T7 (NCBI Database gi: 9627425) and generally brings about maximal translation in bacteria. Yarchuk et al. (1992) and Lee et al. (1999), for example, provide a review of the effects of mutated Shine-Dalgarno sequences.

The half-life of bacterial proteins is from a few minutes up to more than 48 hours.

"Differential gene expression" is understood as meaning the specific expression of individual genes or gene groups which is dependent on the developmental state of a cell, with this expression depending, in particular, on the external conditions and/or the host milieu in which the cell is present.

Gene Expression in *Salmonella*, in Vitro and in vivo

In the case of host-adapted *salmonella* strains (e.g. *serovar typhimurium* in the mouse and *serovar typhi* in humans), *salmonellas* which are ingested orally penetrate, principally through the M cells of the Peyer's patches, into the intestinal wall and are taken up by phagocytes, such as dendritic cells, macrophages and neutrophils. Probably in these phagocytes, the *salmonellas* also reach the draining mesenteric lymph nodes and, from there, reach the liver, spleen, bone marrow, brain and other tissues by way of the blood stream. In all infected tissues, the *salmonellas* multiply intracellularly. If the host is unable to control the infection, multiorgan failure and death ensue.

In the case of strains which are not host-adapted, all that normally occurs is a self-healing diarrhea-associated enteritis. While the intestinal mucosa is partially damaged reversibly in this connection, more deeply lying tissues are not affected.

Both the infected host and the *salmonellas* have at their disposal extensive regulatory networks which are able to adapt the expression of numerous genes to the changing microenvironment (Hensel, 1998). In vitro studies using cell culture models show that *salmonellas* are able to express several hundred proteins, most of which have not yet been identified, differentially in dependence on the host cell line (Burns-Keliher et al., 1998). These in vitro data suggest that *salmonellas* may possibly be able to react, in each case in an adapted manner, to the large number of different microenvironments during the course of the infection (intestinal lumen, Peyer's patches, mesenteric lymph nodes, spleen, liver and bone marrow) (Yrlid et al., 2001; Salcedo et al., 2001). However, the few data which are available for other pathogens, such as *Vibrio cholerae* (Lee, Butler and Camilli, 2001) and *Staphylococcus aureus* (Goerke et al., 2000), show that regulatory mechanisms which are in some cases completely different from those in vitro are active in vivo. It can be assumed, therefore, that the cell culture data can only make a small contribution to understanding gene regulation during the *salmonella*/host interaction during an infection.

Qualitative investigations, which were not tissue-specific, into gene expression in *salmonella* in vivo have demonstrated that up to 100 genes are induced in infected mice (Burns-Keliher, Nickerson, Morrow and Curtiss, 1998). It has not thus far been possible to demonstrate a functional connection between particular regulatory sequences and differential gene expression in various host tissues, and such a connection is not otherwise evident from the prior art, either. It is primarily the difficulties of measuring gene expression in bacteria in infected tissue which are responsible for this deficiency.

Consequently, important aspects of the pathogen/host interaction in the complex course of salmonellosis are not yet understood. Both the pathogenesis of virulent *salmonellas* and the activity of recombinant live *salmonella* vaccines depend on the *salmonella*/host interactions during colonization. For this reason, there is a need for a method for identifying those genes, or groups of genes, which are expressed differentially in different host tissues. Thus, for example, the question which is of importance for the activity of a live vaccine is whether *salmonellas* express genes during the extracellular, early phase in the intestinal lumen which are different from those which they express during the later, intracellular phase in liver macrophages. In laboratory practice, it is not possible, for reasons of expense and time, to use known methods to examine all the approx. 4600 genes of *Salmonella enterica serovar typhimurium* (McClelland et al., 2001) for differential in-vivo expression since no known method can be used as a method for screening for quantitative, tissue-specific expression.

*Salmonella*-based live vaccines consist of an attenuated *salmonella* strain which induces a limited infection, without disease symptoms, and an expression cassette having the foreign antigen whose expression is driven by an upstream located promoter. During the course of a limited infection, following oral administration of the live vaccine, an immune response is induced against the *salmonella* carrier and also against the antigen which is expressed heterologously. However, it has been found, in practice, that the expression of a foreign antigen can overburden the *salmonellas* to such an extent that they only induce a very slight infection during which no adequate immune response develops. It is therefore advantageous to express as little foreign antigen as possible until the *salmonellas* have not reached immunocompetent host tissue and only to induce the expression after that. Such expression systems which are inducible in vivo are as a rule based on differentially regulated promoters. Although there is some qualitative information about promoters which are induced differentially in vivo, quantitative expression data, which would make it possible to select an in-vivo inducible promoter which was optimal for a live vaccine, have not thus far been published.

Known Methods for Analyzing Gene Expression in Vitro and in vivo, and for Screening Modern methods for the global analysis of transcriptomes, using DNA microarrays, and proteomes, using two-dimensional gel electrophoresis or ICAT, offer optimum possibilities for investigating gene regulation in vitro. In the case of *salmonellas*, the complete sequencing of the genomes of several *salmonella serovars* forms a suitable database for these methods. However, under in-vivo conditions, these methods can only be applied in the case of extremely heavily infected tissues since it is only then that the number of bacteria is large enough to be able to separate bacterial RNA and/or bacterial proteins from the large quantities of host RNA and host proteins. These methods are not suitable for investigating tissues which are infected in the normal course of a salmonellosis or experimentally (mice, inoculum of up to $10^{10}$ CFU orally or $10^7$ CFU i.v.) (Diehn and Relman, 2001), since the number of bacteria in the tissue is too small (in the case of *salmonellas*, for example, $10^2$-$10^5$ in the Peyer's patches).

Thus far, the only possibility of obtaining quantitative information with regard to the expression of genes by pathogens in vivo is that of using the recently developed real-time RT-PCR for amplifying bacterial transcripts directly from infected tissue samples (Goerke, Bayer and Wolz, 2001; Rokbi et al., 2001). While the methodology is very sensitive, it requires specific primers as well as adapted temperature cycles for each gene. It is therefore not suitable for being used in screening for genes and/or promoters having defined properties.

Attenuating mutations suggest that the affected genes are at least expressed in vivo at one particular time. An elegant screening method, signature-tagged mutagenesis (Hensel, 1998), makes it possible to rapidly identify functionally important mutations in *salmonellas* and many other pathogens. The method is based on individual genes being irreversibly inactivated by means of transposon mutagenesis. If genes which are essential in vivo are affected, the corresponding clones do not then multiply in the infected animal. The clones are missing in ex vivo isolates (negative selection). The clones are identified unambiguously by means of an individual tag which the transposons carry. The disadvantages of this method are that the only mutations which are found are those which already have a strongly attenuating effect individually even though many relevant genes, which are expressed in vivo, are only important for the infection when interacting with other genes (Mahan et al., 2000). In addition, the negative selection can only detect (only qualitatively) the first tissue-specific activation but not a transient activity or a repression during the course of the infection. It is not possible to perform a positive selection. It is not possible to obtain quantitative information with regard to gene expression or selection in accordance with the strength of the expression.

Differentially regulated promoters can also be analyzed by means of reporter gene assays. The reporter genes β-galactosidase (Slauch, Mahan and Mekalanos, 1994) and luciferase (Contag et al., 1995; Jacobi et al., 1998; Dunstan, Simmons and Strugnell, 1999) enable a sensitive detection to be performed in vivo. The expression is detected by means of a color reaction which is catalyzed by these enzymes in tissue homogenate and is consequently semiquantitative. Reporter genes are therefore mainly used for investigating individual gene assays which are already known. There has not thus far been any description of ex-vivo screening methods which use these reporters.

The IVET method (Mahan, Heithoff, Sinsheimer and Low, 2000), which is frequently used for investigating pathogenic microorganisms, is a special form of the reporter gene assay. The IVET method uses reporter genes which complement a lethal metabolic defect or mediate resistance to an antibiotic. Only those clones in which the reporter gene is inserted downstream of promoters which are active in vivo are able to survive in vivo (complementation of the metabolic defect or resistance to treatment with antibiotics). Resistance markers and complementation markers make it possible to perform a positive selection. Using this method, a variety of promoters which are inducible in vivo, some of which have an important role in the infection, has been found in various pathogens, including *salmonellas* as well. The method is based on a qualitative comparison of expression in vitro and expression in vivo. In practice, therefore, the reporter gene is frequently coupled to another marker which, for example, mediates a color reaction. The method is used, in particular, to identify promoters which give very low background expression in vitro, which is a disadvantage since many important genes are also expressed in vitro. It is not possible to obtain quantitative information with regard to gene expression in vivo (Gort and Miller, 2000).

It is only the new IVET variant RIVET (Lee et al., 1999) which makes it possible to analyze promoter activation kinetically during the infection. RIVET uses resolvase as the reporter gene, with the resolvase, on expression, selectively removing a resistance cassette from the genome. The ratio of resistant and sensitive clones is determined by plating out and used as a qualitative measure of the expression. This approach makes it necessary to use reporter constructs which are specially adapted in dependence on the in-vitro activity of the promoters employed, such that it is impossible to screen for previously unknown promoters. Because the resistance cassette is irreversibly removed, it is only activation, and not a transient activity or a repression, which can be detected. It is not possible to obtain quantitative data, either.

Furthermore, the green fluorescent protein GFP can be used in reporter gene assays. GFP does not require any cofactors and GFP-mediated fluorescence can be measured quantitatively on live samples using fluorescence microscopy and flow cytometry. Cell populations which fluoresce differently can be separated by means of fluorescence-activated cell sorting (FACS). In cell culture models, GFP has been used, for example, to identify some *salmonella* promoters which are activated selectively in infected host cells (Valdivia and Falkow, 1997). Thus far, this screening method has been used in vitro in cell culture infection models with a high MOI (multiplicity of infection). In contrast to cell cultures, infected tissue homogenates contain very many host cell fragments having bacterium-like scattering behavior and GFP-like autofluorescence, which it has not thus far been possible to distinguish from GFP-expressing bacteria when using FACS. This background of interfering particles has made it impossible to use GFP as a quantitative in-vivo reporter for pathogens, such as *salmonellas*, which are principally present intracellularly (Lee and Camilli, 2000). This method can also be used to a restricted extent in vivo under the special conditions of a highly infected tissue. The frog pathogen *Mycobacterium marinum* was, for example, investigated qualitatively in highly infected frog granulomas. It was not possible to determine the expression of the GFP quantitatively.

A ratiometric method which can be used to unambiguously differentiate the tissue autofluorescence from the GFP emission in individual bacteria, by measuring the fluorescence at two wavelengths, has recently been published (Bumann, 2001a). This thereby makes available a method for measuring protein expression (promoter strength) quantitatively even in such bacteria which have been isolated ex vivo and which are to be examined, without previously being cultivated, immediately after they have been isolated. This method has been used to track the activity of a few known promoters on the infection route taken by *salmonellas*, from the intestinal lumen, via the Peyer's patches and mesenteric lymph nodes, to the liver and the spleen. The individual promoters (e.g. psicA, pssaH, pphoP-1, pbgP and ppagC) were cloned, as transcriptional fusions, before the infection, homogenates of the lymph nodes, of the liver and of the spleen were treated with detergent and analyzed by means of 2-wavelength FACS. This made it possible, for the first time, to quantitatively track the activation and repression of some known *salmonella* promoters in specific tissues during the infection.

Description of the Method

A first aspect of the present invention relates to a method for screening bacterial genomes for new regulatory sequences and/or already known regulatory sequences having a previously unknown function.

The method makes it possible to identify and quantitatively characterize, as was not previously possible, new or known regulatory sequences which possess tissue-specific activity. All the regulatory sequences (in particular promoters) which are present in the investigated bacterium are tested collectively without any prior information about the sequences in question being required. In particular, the method is suitable for identifying regulatory sequences which effect differential expression in vivo and in vitro and preferably exhibit a ratio of in vivo expression to in vitro expression of at least about 8. These regulatory sequences can be used, for example, for producing live vaccines.

Another embodiment of the invention relates to the identification of regulatory sequences which, in addition to effecting strong expression in vivo also effect strong expression in vitro. On account of their strong in-vivo expression, these regulatory sequences are suitable for producing live vaccines. In addition, the strong in-vitro expression can improve the immune response to recombinant proteins since, in this case, the immune response can proceed in two phases. In the case of these regulatory sequences, the ratio of in-vivo/in-vitro expression is preferably from at least about 2 to at most about 6.

The method according to the invention comprises the steps of:

(a) introducing partial sequences, which are in each case different, from the genome of a bacterial target organism into a multiplicity of vectors, with the bacterial sequences being inserted in operative linkage to a reporter gene, in particular upstream of a reporter gene but also downstream of a reporter gene, (b) transforming host bacteria with the vectors from (a), with a genome library of the bacterial target organism being obtained in a host bacterium, (c) comparing the strength of the expression of the reporter gene in individual bacterial cells in vivo and in vitro, (d) identifying bacterial cells which exhibit a predetermined first expression strength in vivo and a predetermined second expression strength in vitro, and (e) where appropriate, isolating individual bacterial cells from step (d).

This thereby makes available, after step (d) and/or after step (e), individual clones which contain the promoters, and/or other regulatory elements, having the desired expression properties on an expression vector. Step (c) of the method preferably comprises one or more of the following partial steps:

(ci) administering aliquots of the genome library to at least one experimental animal, (cii) isolating bacterial cells from the at least one experimental animal after a predetermined period of infection, (ciii) determining the strength of the expression of the reporter gene in vivo in the bacterial cells obtained in (cii), (civ) cultivating in vitro bacterial cells which, in step (ciii), exhibit a predetermined first strength of expression of the reporter gene in vivo, and (cv) determining the strength of the expression of the reporter gene in vitro in the bacterial cells cultivated in (civ).

In addition, these clones can be enriched in the genome library if the following procedural steps are also carried out:

(f) jointly cultivating in vitro at least a part of the bacteria identified in step (d).

(g) administering the bacteria cultivated in (f), or an aliquot thereof, to at least one experimental animal.

(h) repeating steps (c) to (d) or (c) to (e) using the experimental animals infected in step (g).

After steps (d), (e) or (h), individual clones can be subjected to further investigation by carrying out the following procedural steps:

(i) propagating the clone in vitro.

(j) administering the bacteria cultivated in (i), or an aliquot thereof, to at least one experimental animal.

(k) repeating step (c), or steps (c) to (d) or (c) to (e), using the experimental animals infected in step (i).

Steps (i) to (k) are used, for example, for generating a profile of the expression of a regulatory sequence in different tissues.

Steps (a) and (b)

The genome library of a target bacterium to be investigated is prepared, in accordance with steps (a) and (b), in a host bacterium which is able to survive and propagate in vitro and in vivo under suitable conditions. In this connection, fragments of the genome of, for example, about 0.1-2 kb in length are inserted into a suitable vector, preferably upstream of the coding sequence of a reporter gene. In one embodiment, all the regulatory elements which are required for initiating transcription are removed from the sequence upstream of the reporter gene beforehand. An efficient Shine-Dalgarno sequence (e.g. TTTAAGAAGGAGATATACAT; SEQ ID No. 1) for initiating translation can be present at a distance of 4-14 nucleotides before the reporter gene. If the inserted fragments contain regulatory sequences, in particular promoters, the reporter gene can then be expressed when the regulatory sequences are activated provided the regulatory sequences are present in the correct orientation in relation to the coding sequence of the reporter gene (promoter-trap vector).

If, in an alternative embodiment, a constitutive promoter and a Shine-Dalgarno sequence are located before the reporter gene, other regulatory sequences which influence the activity of the promoter can be identified by inserting them upstream of the promoter.

The genome library can be prepared from the genomes of any arbitrary target bacteria. Any arbitrary bacteria can likewise be used as the host. Consequently, the target bacterium and the host bacterium can be the same or different. Gram-positive and Gram-negative bacteria are suitable for both purposes. It is possible to use bacteria of the Enterobacteriacae family, belonging to the genera *Salmonella*, *Escherichia* or *Yersinia*, and/or the species/serovars *Salmonella enterica serovar typhimurium*, *Salmonella enterica serovar enteritidis*, *Salmonella enterica serovar typhi*, *Salmonella enterica serovar Dublin*, or *Salmonella enterica serovar cholerasuis*. The *Salmonella enterica serovar typhimurium* strain SL 1344 is particularly suitable. In addition to this, bacteria which have a response-augmenting effect on the human immune system and which are licensed as foodstuff additives (probiotic bacteria), and which therefore come into consideration as (e.g. orally administerable) live vaccine carriers, e.g. the family Lactobacillae (Gram-positive), Lactococcae (Gram-positive) and the (Gram-negative) *E. coli* strain Nissle (1917) are suitable.

Where appropriate, the genome library can be constructed in an intermediate host. In this case, the plasmid DNA having the inserts is isolated from the intermediate host and used to transform the final host bacterium. *E. coli* is particularly well suited for being used as the intermediate host.

The genome library preferably comprises more than 90%, particularly preferably more than 99%, of the bacterial genome. With the size of the *Salmonella* genome being about 5 Mb (McClelland et al., 2001) and the size of the DNA insert being 0.5 kb, the *Salmonella* genome can be represented by about 20 000 clones (without redundancy but with both orientations). Using the method according to the invention, it is possible to generate libraries, in the intermediate host *E. coli*, which contain more than $2 \times 10^5$ independent clones having insert-carrying plasmids. The plasmids can be isolated from this library and transformed into the final host, e.g. *Salmonella enterica serovar typhimurium* SL 1344. In total, it is possible to generate $10^6$ transformants in order to obtain coverage of the genome which is as complete as possible.

Preference is given to embodiments in which the library is prepared from the genome of the host in the host itself. Inserts having a length of from 500 to 1500 bp are well suited for identifying regulatory sequences. A length of from 500 to 700 bp is particularly suitable.

The vector for preparing the genome library essentially consists of elements for replication in the host (and, where appropriate, in intermediate hosts), one or more marker genes and/or reporter genes for the selection, and sequences for the cloning. Preferably, at least one of the reporter genes encodes a fluorescent protein, e.g. GFP (green fluorescent protein) or GFP variants (e.g. giving a superior fluorescence yield: enhanced GFP or EGFP, or providing UV excitation: GFPuv; see, for example, Sullivan and Kay, 1999, in particular p. 24) or red-fluorescent DsRed, and improved variants. The use of GFP as a fluorescent reporter protein has been described in detail (Sullivan and Kay, 1999). Expression vectors (in particular promoter-trap vectors) for GFP have been described in Valdivia and Ramakrishnan (2000).

GFP is generally very stable in living cells, with a half-life of more than 24 h. GFP variants having a clearly much shorter lifetime in vivo can be obtained by modifying the C terminus, resulting in the GFP being degraded more rapidly. The C terminal sequence AANDENYALAA (SEQ ID No. 2) is specifically recognized by proteases which degrade proteins specifically from the C terminus (Andersen et al., 1998). The degradation rate can be modulated by altering the last three amino acids in this sequence (Keiler and Sauer, 1996).

It is furthermore possible to use the GFP variant GFP_OVA (Bumann, 2001b) as the reporter protein, with this variant making it possible to obtain constructs which are stable even at a high expression (Example 1). There are thus far no known variants of GFP_OVA whose lifetime has been modulated. In order to detect weak promoters, GFP_OVA must be replaced by very stable GFP.mut3, because of the higher concentration which can be reached (Example 1).

Step (c)

Step (c) preferably comprises one or more of the partial steps (ci) to (cv). It is possible to use the customary methods for administering the genome library corresponding to step (ci) to an experimental animal: injection (max. $2 \times 10^7$ CFU intravenously, $2 \times 10^9$ CFU intramuscularly, $2 \times 10^9$ CFU subcutaneously or $2 \times 10^7$ CFU intraperitoneally), oral administration of $5 \times 10^{10}$ CFU (pretreatment with 5 g of streptomycin/l in the drinking water) or nasal administration ($5 \times 10^6$ CFU). The customary auxiliary substances and carrier substances, which are known to the skilled person, are added where appropriate. The administration is preferably carried out intravenously (e.g. into the tail vein) since the highest colonization rates in the target organs (e.g. lymph nodes, spleen and liver) can be achieved in this way. Any mammals, in particular the mouse, the rabbit, the rat, anthropoid apes or calves, are suitable for use as experimental animals. It is possible, for example, to use BALB/c mice, immunodeficient mice, immunized mice or immunosuppressed IFN(R (−/−) mice.

The method can be used for developing live vaccines for humans provided use is made of bacteria which do not exhibit any pathogenicity, or only very slight pathogenicity, and which can be administered orally or nasally.

The period of infection in accordance with step (cii) is measured on the basis of the course of the infection and the target organs which are to be investigated. When using mice as the experimental animals and *salmonellas* as the host for the gene library, it is possible to use infection times of between 1 h and 120 h for tracking the course of the infection from the colonization of the Peyer's patches through to the colonization of the liver and spleen. In order to be able to conform to the animal protection provisions, the early and middle phase of the infection should be investigated. Terminally sick animals should not be investigated. Customary methods are used to homogenize and lyze the tissue samples corresponding to step (cii) under mild conditions such that the bacteria in the resulting single cell suspension very largely remain viable and able to propagate. The tissues which can be used are any infected tissues, in particular the intestinal lumen (i.e. the intestinal content is investigated), intestinal tissue, Peyer's patches, spleen, liver, lymph nodes, kidney, bone marrow, brain, blood, intraperitoneum, uterus, oviduct and connective tissue. The method is also suitable for identifying regulatory sequences which are active in a tissue-specific manner.

The identification in accordance with step (ciii) is effected using methods which are suitable for the respective reporter protein. It is important that the expression strength of the bacteria is measured immediately after they have been isolated ex vivo, without any significant protein degradation or significant protein neosynthesis, or growth and/or propagation having taken place. Furthermore, it is necessary to use methods which do not limit the viability of the bacteria and their ability to propagate. Methods which are able to determine the fluorescent proteins quantitatively in the live bacterium are therefore preferred. FACS makes it possible to identify and isolate individual bacteria which meet a predetermined criterion for fluorescence strength (as threshold or as a range with an upper and lower limit). This makes it possible to readily identify and isolate bacteria which are expressing a fluorescent protein. Because of the autofluorescence of the residues of the host tissue, the use of standard FACS, with, as is customarily the case, only one emission wavelength being measured, leads to unusable sorting results in the case of the bacterial suspensions according to the invention. A ratiometric method, with the measurement of two emission wavelengths (details of the method, see Bumann, 2001a), is therefore used, with this method enabling bacteria having a predetermined expression of the marker protein to be isolated cleanly. The strength of the fluorescence is the measure of the quantity of expressed protein and can be calibrated to copies of the protein per cell. The calibration can be effected by way of the extinction coefficient of the fluorescent protein or by way of a densitometric protein determination using reference samples of differing concentration, e.g. in an SDS gel.

The expression strength in step (ciii) is preferably provided as a threshold for implementing a positive selection (for clones which are expressing the gene). The individual bacterium then has to exceed the threshold in order to be selected. The individual bacteria which are isolated in accordance with step (ciii) are consequently clones which, under the chosen conditions, are expressing the reporter protein at a given minimum strength. This thereby isolates such clones in which the insertion sequence before the reporter gene contains a promoter which is active in the tissue under investigation.

The threshold for identifying strong promoters (positive selection) is understood as being at least 25 000 copies of the protein per bacterium. Other suitable thresholds can be selected between 25 000 and 250 000 copies/cell. If step (ciii) is passed through more than once (step (h) and/or step (k), see below), a threshold of 4500 copies is also suitable for the first passage.

Alternatively, the selection criterion can be a range, with a lower and upper limit, within which the expression must lie. It would be possible, for example, to use such a range to identify moderately strong promoters. Preference is given to using a range having a lower limit of 4500 and an upper limit of 25 000 copies.

If particular selection conditions are chosen from the range of possible limits, it is then additionally possible to achieve the situation where the selected bacterial clones are able to pass through the natural course of infection just as well as the host strain on its own. Under these conditions, therefore, the infectivity of these clones is no less than that of the host strain on its own. A reduction in colonization of up to 25% does not significantly restrict infectivity. A clone which is expressing about 4500-250 000 copies/cell of a recombinant protein in step (ciii) therefore meets these conditions since a decrease in colonization of more than 25% is not measured in this case. Preference is given to selecting clones which express between 25 000 and 250 000 copies/cell. Particular preference is given to clones which express between 50 000 and 250 000 copies/cell. The limits have to be lowered in the case of toxic recombinant proteins if the toxicity restricts the infectivity.

The clones which are obtained in step (ciii) are cultivated, in accordance with step (civ), under suitable conditions in vitro, preferably jointly or in aliquots. The skilled person is familiar with these suitable conditions. The strength of expression is determined, in accordance with step (cv), as previously described.

Step (d)

In accordance with step (d), the bacteria obtained from step (ciii) are subjected to a second selection step using the methods which are suitable in accordance with steps (civ) and (cv). A threshold for implementing a negative selection (clones which express the reporter gene below the threshold under the chosen conditions) is preferably determined. The threshold for negative selection is understood as being fewer than 2000 or 4500 copies/cell (in the 2-wavelength FACS). This threshold can be lowered still further where appropriate. Steps (c) and (d) consequently constitute a two-step selection.

Step (e)

In accordance with step (e), standard microbiological methods, which are known to the skilled person, can be used to readily isolate individual clones from the bacterial suspension derived from step (d).

Step (f)

The bacteria are cultivated in step (f) as in step (civ) using a method known to the skilled person.

Step (g)

The bacteria which are cultivated in (f) are administered, in accordance with step (g), as described for step (ci). Preference is given to using the same administration route and the same experimental animal species as in step (ci).

Step (h)

The repetition of the selection steps, in accordance with step (h), serves to enrich clones which possess the desired expression properties. The selection thresholds for the in-vivo and/or in-vitro expression strength(s) are modified where appropriate (see that step). In addition, it is possible to use the same parameters and methods as in the case of the preceding implementation(s) of the procedural steps.

Step (i)

The conditions under which the individual clones from steps (d) and (e) or (h) can be cultivated are known to the skilled person. Preference is given to using the conditions which were already employed in step (c).

Step (j)

The bacteria cultivated in (i) are administered, in accordance with step (j), as previously described. Preference is given to using the same administration route and the same experimental animal species as in step (ci) and/or step (g)

Step (k)

The repetition of the procedural steps, in accordance with step (k), is used to further investigate the expression properties of previously identified clones. In particular, it is possible to generate a profile of the strength of expression in different host tissues (e.g. Peyer's patches, spleen or liver) or host cell types (macrophages, neutrophiles or dendritic cells). Individual host cell types can be obtained by means of purification using standard methods, e.g. magnetic cell sorting, MACS or FACS (Yrlid, Svensson, Hakansson, Chambers, Ljunggren and Wick, 2001; Salcedo, Noursadeghi, Cohen and Holden, 2001).

Localization of the Regulatory Sequences

Another aspect of the invention relates to the regulatory sequences which are present in the inserts in the clones which are identified using the method. Standard methods known to the skilled person can readily be used to examine these clones for the insert which is present in the vector. The insert can readily be sequenced using standard methods. This makes it possible to further localize the regulatory sequences in the inserts which have been obtained. For this, steps (i), (j) and (k) are carried out using clones which contain the partial sequences. If it is assumed that the regulatory sequences do not, all in all, constitute more than between 50 and 200 consecutive bases, it is then possible to identify such a sequence in a few steps by bisecting the insert and subjecting the clone which is in each case functional to further investigation. If both subclones are no longer active, it is then assumed that the regulatory sequence is located in the middle and has been cut and further work is conducted with a construct of equal length which contains the cut sequence. In this way, a functional sequence of about 60 (200) bases would have been identified after at least three and at most six steps if the length of the insert is assumed to be 500 bp (1500 bp).

Another possibility for precisely locating the regulatory sequences consists in using the computer to make predictions. Any reading frames (i.e. sequences composed of a start codon and as many subsequent triplets as possible without a stop codon) which may possibly be present can be identified within the insert sequences. These predictions can be confirmed by comparison with the GENBANK sequences. The regulatory sequences in the inserts consequently as a rule end at the very latest at the proximal start codon. The sequences before the start codon (the intergenic regions) can be investigated further for the presence of putative promoters (transcription starts). The algorithms of Reese (1994), Reese and Eeckman (1995) and Reese et al. (1996) are suitable for this purpose. An implementation of the algorithms is available on the Internet under http://www.fruitfly.org/seq_tools/promoter.html. The results of the computer analysis in the case of the sequences according to the invention are presented in Tables 2 and 5. It is consequently possible to localize regulatory sequences, in the insertion, to the sequence between the putative transcription start and the proximal ORF. In order to avoid inaccuracies in predicting the transcription start, the sequence should be extended upstream by, e.g., 10, 20, 30, 40 or 50 bp.

Preference is given to adding a further sequence of 50, 100, 150 or 200 nucleotides upstream of the transcription start in order to reliably detect the parts of the regulatory sequences which are located within this sequence (e.g. the −10 and the −35 regions). Components of the regulatory sequences upstream of the −35 region can be offhand determined readily (e.g. as described above).

Live Vaccines

Another aspect of the invention relates to the use of regulatory sequences according to the invention for developing a live vaccine. Demonstrating expression in a tissue and a lack of expression in vitro simultaneously shows that the insert, or a partial sequence thereof, as the method according to the invention has identified it, contains at least one regulatory sequence from a bacterial genome and is sufficient for controlling the tissue-specific expression of recombinant proteins. As a consequence, the insert, or a partial sequence thereof, is at the same time suitable for effecting the tissue-specific expression of a recombinant antigen. For this, the insert, or a partial sequence thereof, is placed before the gene to be expressed. This construct is either integrated into the genome of a suitable vaccine strain or introduced into a vector which can be replicated in the vaccine strain, which is transformed into the vaccine strain. The construct can be inserted into the genome of the host cell, for example as a tandem, i.e. it is inserted close to the natural gene locus which is expressed by the regulatory sequence according to the invention. Examples of suitable antigens would be the Helicobacter antigen urease or AIDA fusions.

The regulatory sequences according to the invention can also be used by integrating a heterologous nucleotide sequence, which encodes a recombinant antigen or another heterologous protein, at the corresponding site in the genome of the host cell, e.g. of a bacterium, such that the regulatory sequence is able to bring about the expression of the heterologous nucleotide sequences in its natural functional context.

The gene which is expressed naturally by the regulatory sequence according to the invention can be inactivated by the insertion provided the gene is not essential (e.g. virK, ugd, sifB, pSLT046, phoN, iicA and stm2585A, see Table 4). In addition, the heterologous sequence can be inserted into an available operon without the expression of this sequence disturbing the expression of the sequences which are naturally present. Another possibility is to express the heterologous sequence as a fusion with the natural gene. The advantage of these different configurations is that inheritance is more stable in the chromosome than on expression vectors. The stability of the genetic configuration is an important criterion for the licensing of a recombinant live vaccine.

Because of their strong expression (in vivo, a maximum of 841 000 copies/cell when using expression vectors), the regulatory sequences according to the invention are particularly well suited for being integrated into the genome. Since generally only one, or a few, copy(ies) of the heterologous sequence is/are present in the chromosome, it has to be expected that the expression will be lower than when using expression vectors, which as a rule exhibit a relatively high copy number. Since 75 000 copies/cell are sufficient for achieving a saturating immune reaction (see Example 3), a reduction in expression of up to 90% can be accepted when using the regulatory sequences according to the invention in chromosomally integrated form. The regulatory sequences 4.5G, A.8H, 2.1F and 1.3G are therefore particularly preferred. A.8H and 2.1F contain regulatory sequences which express nonessential genes. These genes can therefore be replaced with heterologous sequences without impairing the colonizing ability of the *salmonellas*. While 4.5G and 1.3G have not thus far been characterized with regard to their virulence function, both are phage-associated. Since phages as a rule only have slight effects on *salmonella* virulence, it can be assumed that the genes which are regulated by 4.5G and 1.3G can also be replaced with heterologous sequences without this being to the detriment of the colonizing ability.

Those regulatory sequences according to the invention, for expressing recombinant proteins, which are naturally present in the human-pathogenic strains *Salmonella typhimurium, S. typhi, S. paratyphi* A or *S. paratyphi* B are of particular interest for developing a live vaccine. It is therefore advantageous to use Table 4 to select, from the group of regulatory sequences according to the invention, those sequences which are at least present in *Salmonella typhimurium, S. typhi, S. paratyphi* A or *S. paratyphi* B or in two or more thereof. The advantage is that, when an attenuated strain of *Salmonella typhimurium, S. typhi, S. paratyphi* A or *S. paratyphi* B is used as the vaccine strain, the recombinant protein is expressed under the control of the autologous regulatory sequence within the natural regulatory network. Consequently, the expression of the recombinant protein follows the activity of the regulatory sequence during the course of the infection and is easier to control and predict.

Another aspect of the invention relates to the graduated modulation of the expression. The expression strength, which, in the case of a live vaccine, should be chosen to have maximum effect, depends on antigen-specific factors, in particular toxicity, degradation rate and immunogenicity. An efficient method of selectively optimizing the activity of a recombinant live vaccine is to use an identified regulatory sequence which can bring about strong expression in vivo and to selectively attenuate the expression by means of selectively modifying the Shine-Dalgarno sequence. This makes it possible to optimize the activity of a recombinant live vaccine in a selective manner. It is sufficient to use, in addition to the wild-type pGO WT, one of five mutations, which are described here, of the phage T7 gene 10 Shine-Dalgarno sequence in the 16S RNA-complementary tetranucleotide GGAG and/or the adjacent nucleotides (see plasmids pGO WT, pGO_mut1, pGO_mut2, pGO_mut3, pGO_mut4 and pGO_mut5) in order to lower the strength of the expression predictably, and in a graduated manner, down to about 2% of the initial value. In this way, it is possible to cover the entire range which is reasonable for protein expression and/or antigen expression. Mutating the Shine-Dalgarno sequence makes it possible to selectively attenuate the strength at which any promoters are expressed.

Description of New Promoters which Have been Identified Using the Method According to the Invention The invention also relates to *salmonella* promoters which are active in vivo and which are contained in the insertions 4.5G, 1c, A.8H, 1f, 3g, 2a, 4a, 10g, 12b, A.2A, A.7A, A.9D, A.10F, A.11B, A.11H, A.12A, A.12G, CLII.3A, CLII.4C, CLII.9B, CLII.11C, CLII.12C, 3.2E, 3.4F, 3.6B, 3.9A, 3.9E, A.11A, A8.B, CLI.5A, 4.4G and A1.A (see FIGS. 3-29 and 33-37) as well as to promoters which are derived therefrom by means of mutations, e.g. by means of insertions, deletions and/or substitutions of single bases or short sequence segments, for example of up to 3 bases in length, and to their use for producing live vaccines, in particular for the expression of recombinant, preferably heterologous antigens, in live vaccines.

All the promoters which are described below are described here for the first time as regards their in-vivo expression strength. While data with regard to induction in macrophages in cell culture were already available in regard to plasmids 2a, 4a, 10g and 12b, these data did not enable any reliable prediction to be made in regard to in-vivo conditions (Beuzon, Unsworth and Holden, 2001). In the case of the particularly attractive promoters 1f and 3g as well as and in the case of promoter 1c, there have not previously been any data available at all in regard to expression in host cells, either in the case of cell culture infection models or in the case of in-vivo models. All the sequences apart from 3g are homologous with the known genome sequence of *S. enterica serovar typhimurium* LT2 (McClelland et al., 2001).

All of the promoters mentioned in Example 4 are likewise described here for the first time as regards their in-vivo expression strength. Those promoters which show an in-vivo/in-vitro expression ratio of at least about 8 are particularly suitable for differentially expressing recombinant proteins. These are described below in more detail. Data with regard to expression in cell culture are available for the promoters in the sequences A.11B, 2.2A, CLII.4C, 2.4A, A.9D, A.7A, 3.4F, 3.2E, 3.6B and 3.9E. Qualitative data in regard to in-vivo expression are additionally available in the case of the promoter in sequence 3.9E (Valdivia and Falkow, 1997). All of the sequences apart from 1.3G are homologous with the known genome sequence of *S. enterica serovar typhimurium* LT2 (McClelland et al., 2001). The promoters in sequences A.11B, CLII.9B, CLII.12C, A.2A, 2.1F and 1.3G approximately fulfill the selection criteria which are specified in Example 4 as being preferred. While the in-vitro threshold was in some cases markedly exceeded in clones A.10F, CLII.3A, 2.2A, 4.5G and A.8H, the ratio of the expression strengths was greater than 8. Consequently, in addition to the 13 sequences which fully satisfy the preferred selection criteria, these 11 regulatory sequences are also suitable for differentially expressing recombinant proteins (cf. Table 4).

In addition to the in-vivo/in-vitro ratio of the expression, the absolute strength of the in-vivo expression is also an important criterion for suitability for producing a live vaccine. The regulatory sequences which are present in the sequences A.11A, A.8B, CLI.5A, 4.4G and A.1A are particularly advantageous for producing a live vaccine since, in some cases, they show an in-vivo expression (from 95 000 to 222 000 copies/cell, see Table 4) in the target tissue which is greater than that of the regulatory sequences which fully or approximately satisfy the selection criteria. The expression ratio is at least 2 and at most 6. This is due to an in-vitro expression of from 36 000 to 59 000 copies/cell, which is greater than that of the above-described regulatory sequences apart from 4.5G. Aside from the T cell response, for which a delayed antigen expression, as is brought about by the regulatory sequences having a very low in-vitro expression, is optimal, the regulatory sequences A.11A, A.8B, CLI.5A, 4.4G and A1.A have the additional advantage that, because of the higher in-vitro expression, an initial quantity of antigen is provided in a live vaccine, with this initial quantity being crucial for forming antibodies. The strong in-vitro expression can consequently be used to induce a biphasic immune response. The sequences of these promoters are shown in FIGS. 33-37.

Plasmid 1c contains a transcriptional fusion of gfp_ova with aroQ, which encodes periplasmic chorismate mutase (Calhoun et al., 2001). Previously, nothing was known about the in-vitro and in-vivo expression of aroQ. Chorismate mutase is involved in the biosynthesis of the aromatic amino acids tyrosine and phenylalanine. Several powerfully attenuating mutations (aroA, aroC and aroD) are located in genes which are involved in the same metabolic pathway (Groisman and Ochman, 1997). It is possible that aroQ is likewise required for full virulence. On the other hand, the *salmonella* genome contains several chorismate mutase genes (aroQ, pheA and tyrA), for which reason the importance of aroQ is thus far unclear.

Plasmid 1f contains a genome fragment which is located immediately upstream of sifB. SifB is induced under a variety of in-vitro conditions; nothing has previously been known about its expression in host cells in vitro or in vivo (Miao and Miller, 2000). SifB is 30% identical with the known virulence factor SifA (see also below, plasmid 12b) and is presumably translocated into the host cell cytosol by means of a type III secretion system; however, the importance of SifB for infection is thus far unclear. The low expression strength of $P_{sifB}$ in vitro, and the dynamics of its induction in vivo, are superior, for heterologously expressing foreign antigens, to those of all the other promoters which have previously been characterized quantitatively (previous best promoter $P_{pagC}$: in-vitro activity in different *salmonella* strains 10 000-50 000 copies of GFP_OVA per cell, in vivo 150 000 to 230 000 copies per cell, Bumann, 2001b). In particular, the promoter contained in plasmid 1f has comparably low activity (fewer than 2500 copies per cell) in the logarithmic growth phase in vitro in a variety of strains of the *typhimurium serovar*, and also in the typhi strain Ty21a *serovar*, which is licensed as a live vaccine, and can be induced in late-stationary cultures, which means that constructs which contain this promoter can be used widely and can be readily tested in vitro.

The plasmid 2a contains a transcriptional fusion of gfp_ova with phoN, which encodes a PhoP-regulated acid phosphatase. While PhoN is induced in macrophages in cell culture, data on its in-vivo expression have thus far been lacking. PhoN is not required for *salmonella* virulence in the mouse model (Miller, Kukral and Mekalanos, 1989).

Plasmid 3g contains a transcriptional fusion of gfp_ova with a reading frame which is not present in *Salmonella enterica serovar typhimurium* LT2 but which possesses low homology with reading frame stm2137 (in this regard, compare McCleland et al., 2001). A high degree of homology exists with a sequence segment, which has not been further characterized, from *Salmonella enterica serovar Dublin*. The sequence of the genome is to be found in the National Center for Biotechnology Information (Taxonomy ID 98360, ref=NC_002961, Contig UIUC_98360). Nothing has previously been known about its expression in vitro and in vivo. The low expression strength in vitro, and the dynamics of the induction in vivo, are superior, for heterologously expressing foreign antigens, to those of all the other promoters which have previously been characterized quantitatively and are comparable to those of the promoter $P_{sifB}$ (see above, plasmid 1f). This promoter also has a background expression which is generally low and high induction dynamics in vivo. Its ability to be induced in the stationary phase makes it easy to test new vaccine constructs in vitro. The importance of insert 3g for *salmonella* virulence is thus far unknown. The LT2 isolate, which lacks corresponding sequences has only low virulence in the mouse model (Wilmes-Riesenberg, Foster and Curtiss, III, 1997). In addition to a mutated rpoS gene, sequences, such as the 3g insert, which are present in the wild type are possibly also responsible for this. A reading frame (bp 572-375) having homology with phage invertases is located upstream of the transcriptional fusion. Insert 3g may therefore possibly be a mobile element which could be unstable in the *salmonella* genome. Further support for this is provided by the fact that a part of the tRNA 2 for serine (serU) (bp 22-83), with a high degree of congruence with the genome sequence, is located further upstream. tRNA genes are frequently insertion sites for mobile elements such as pathogenicity islands, for example. The high pathogenicity island (Schubert et al., 1999) which is rapidly lost during laboratory passages is, for example, inserted in the vicinity of serU in pathogenic *E. coli* bacteria.

Plasmid 4a contains a transcriptional fusion of gfp_ova with pagD, which encodes a cell envelope protein (Gunn et al., 1995). While PagD is induced in macrophages in cell culture, nothing has been previously known about its expression in vivo. PagD is not itself required for *salmonella* virulence in the mouse model since a deletion has no effect on the $LD_{50}$. On the other hand, transposon mutagenesis of this gene results in intense attenuation, which can presumably be explained by the fact that the interfering transposon reduces the expression of a gene (stm1243), which is possibly essential and which is located downstream of the $P_{pagD}$ promoter.

Plasmid 10g contains a transcriptional fusion of gfp_ova with pipB from *salmonella* pathogenicity island V (Pfeifer et al., 1999). In an in-vitro cell culture infection model, *salmonellas* upregulate the expression of pipB in macrophage-like cells. There have not previously been any in-vivo data on its expression. PipB is required for *Salmonella enterica serovar typhimurium* to be fully virulent in the mouse model when small doses are inoculated orally.

Plasmid 12b contains a transcriptional fusion of gfp_ova with sifA. While SifA is induced in macrophages in cell culture, there have not previously been any data on its in vivo expression (Beuzon, et al., 2000). Since, however, the phenotype of SifA mutants (see below) can be detected in the spleen, it can be assumed that sifA is expressed in there (Salcedo, Noursadeghi, Cohen and Holden, 2001). SifA is secreted by the type III secretion system of *Salmonella* pathogenicity island II and is required for preserving the phagosomal membrane (Beuzon, et al., 2000). SifA mutants are greatly attenuated in the mouse model.

The properties of the promoters which are contained in the sequences 10.9B, 4.1A, 10.1B, 10.1A, 10.6A, A.7D, 4.4A, 4.7C, 4.8H, 10.7A, 4.1B, CLII.5C, A.2G, A.8D, CLII.2B, 10.12A, A.3H, A.1A, A.8B, 4.4G, A.11C, CLII.8C, A.4H, CLII.1B, A.7H, CLII.7B, A.3D, A.11A, CLI.5A, A.8C, CLII.5A, CLII.4A, CLII.9C, A.9E, A.11B, A.10F, CLII.3A, CLII.9B, CLII.12C, 2.2A, CLII.4C, CLII.11C, A.11H, 4.5G, A.12A, A.2A, 2.4A, A.12G, A.8H, A.9D, A.7A, 3.4F, 3.2E, 3.9A, 2.1F, 1.3G, 3.9E and 3.6B, in particular their function, the genes which they express, and their occurrence in different *salmonella* species or *serovars*, and other bacterial species, are described in Tables 4 and 5.

Three regulatory sequences from Example 2 (1c, 10g and 12b) were found once again in Example 4 (in this case, A.2A, 3.4F and 3.6B, see FIGS. 30-32). Homologous regions of the sequences exhibit slight differences from each other. Stronger expression was found in Example 4. This affects the upper threshold for the in-vivo selection rather than the lower threshold for the in-vitro selection and therefore leads to an increase in the in-vivo/in-vitro expression ratio (cf. Tab. 4 and Tab. 2). The reason for this is that residues (or relatively long residues) of the autologous gene impeded the expression of a GFP fusion protein in the clones from Example 2. It is therefore advantageous, when using the regulatory sequences according to the invention to express a recombinant protein differentially, to connect the sequence encoding this protein directly to the proximal start codon (see Table 2 and Table 5). Regulatory sequences which are present in clones listed in Table 4 and whose expression ratio is less than 8 according to the experimental results given in Table 4 could then also be suitable for eliciting differential expression.

The regulatory sequence in the insert 3.6B gives an in-vivo/in-vitro expression ratio of more than 400. This regulatory sequence is therefore particularly suitable for differentially expressing a recombinant protein. The insertion 12b regulatory sequence, which is homologous thereto and which shows an expression ratio of about 19 is also particularly suitable (cf. Table 2). This ratio can be improved by truncating at the proximal start codon.

The regulatory sequence in insert A.11A contains the promoter for UDP-glucose/GDP-mannose dehydrogenase, which is not essential for virulence. The functions of the genes which are expressed by the regulatory sequences of inserts A.8B, 4.4G and A.1A are unknown. The corresponding genes encode putative cytoplasmic proteins. The regulatory sequence of insert CLI.5A controls the expression of the Pho-P-dependent regulator mig-14, which is essential for virulence.

The invention will be further elucidated by means of the following figures and examples.

EXAMPLES

Example 1

Comparison of Different GFP Variants as Reporters of *Salmonella* Gene Expression in Infected Tissues; Test of their Suitability for being used in the Screening Method According to the Invention Green fluorescent protein (GFP) is a frequently employed reporter of gene expression in a large number of organisms. A long GFP lifetime leads to high concentrations, which can be measured readily but which may possibly also be a great burden to the expressing cells, at steady-state equilibrium. While GFP variants which have a short lifetime are less of a burden on the expressing cells, because of the smaller quantities of GFP at steady-state equilibrium, the correspondingly weaker fluorescence signal simultaneously impairs measurability. An important prerequisite is therefore the choice of a GFP variant which, in interaction with the expression strength of attractive promoter candidates, brings about optimal expression of GFP.

In order to select optimal GFP variants for investigations into *salmonella* gene expression during an infection, long-lifetime GFP (GFP.mut3, Cormack, Valdivia and Falkow, 1996) and different variants (GFP_OVA, GFP_ASV and GFP_LVA, Andersen, Sternberg, Poulsen, Bjorn, Givskov and Molin, 1998) were compared as in-vivo reporters for a strong promoter ($P_{pagC}$) or a weak promoter ($P_{spvA}$).

Plasmids pJBA27 (GFP.mut3), pJBA113 (GFP_ASV) and pJBA111 (pGFP_LVA) were digested with XbaI and HindIII. The 1 kb fragments were substituted for corresponding fragments in pMW57 ($P_{pagC}$-GFP_OVA) or pMW74 ($P_{spvA}$-GFP_OVA).

The resulting constructs were transformed into *Salmonella enterica serovar Typhimurium* SL1344 (a streptomycin-resistant calf-derived wild-type isolate which is virulent in the mouse model, see Hoiseth and Stocker, 1981). Female BALB/c mice, which were 8-12 weeks of age, were infected orally with approx. $3 \times 10^8$ CFU. After 4 days, the colonization of the Peyer's patches was determined by plating out. The GFP fluorescence (copies per cell) was measured by means of 2-wavelength FACS.

The results are summarized in Table 1. The controls show that, under the given experimental conditions, a colonization rate of from 100 000 to 120 000 CFU can be anticipated. The data furthermore show that the expression of <4000 copies of GFP per cell does not impede colonization.

An expression of GFP of between 50 000 and 250 000 copies is accompanied by a reduction in colonization down to 75-85% of the control. Expression of 400 000 copies of GFP reduces colonization down to about 25% ($P_{pagC}$-GFP_ASV). 2 000 000 copies of GFP per cell massively impede colonization of the host tissue (<1%).

Using the strong promoter $P_{pagC}$, a GFP expression of 237 000 and, respectively, 179 000 copies per cell, associated with a number of 90 000 and, respectively, 80 000 CFU isolated ex vivo, were measured when employing the GFP variants GFP_OVA and GFP_LVA. Since the colonization achieves at least 75% of that of the control strain, these GFP variants are consequently suitable for identifying strong and medium-strong promoters. The variant GFP.mut3 is not suitable since the number of CFU was too greatly reduced by the high expression. In order to search for medium-strong and strong promoters, it is consequently necessary to choose a GFP variant which has a shorter half-life than GFP.mut3 so as to ensure that 250 000 copies per cell is not exceeded.

The variants GFP_OVA and GFP_ASV are not suitable for identifying weak promoters since, when the weak promoter $P_{spvA}$ was used, the numbers of copies per cell were too low (<4000) for detection. The variant GFP.mut3 achieved adequate expression under these conditions. It is consequently necessary, in order to search for weak and medium-strong promoters, such as $P_{spvA}$, to choose a GFP variant which has a longer half-life than does GFP_OVA (e.g. GFP.mut3, which carries the wild-type C terminus, see Cormack et al., 1996), such that at least 10 000 copies/cell can be achieved. This value is higher than the detection threshold by a factor of 2.

Other GFP variants and other fluorescent proteins can be tested for their suitability for being used in the method according to the invention by reworking the example. To do this, it is only necessary to replace the sequence encoding the GFP or GFP_OVA in the given expression vectors with the sequence encoding the desired protein. In order to implement the method, it is necessary to achieve a copy number of between 10 000 and 250 000. Lower expression levels would also be adequate if more strongly fluorescing GFP variants, which might possibly become available in the future, were to be used. The promoters which are employed here, $P_{pagC}$, as an example of a strong promoter, and $P_{spvA}$, as an example of a weak promoter, can be used as promoters which cover this range.

Any other *salmonella* strains, or other bacterial species, can be used if they achieve at least a colonization rate of 75% of that of a plasmid-free control strain which is otherwise identical.

Example 2

Construction of a *Salmonella* Genome Library and Sorting in Accordance with GFP Expression in vivo; Selection Methods for Identifying Promoters which are Regulated in a Tissue-specific Manner A genome library was produced in *Salmonella enterica serovar typhimurium* for the purpose of obtaining information with regard to *salmonella* promoters which are active during the course of an infection. Mice were infected with aliquots of this library. The clones were isolated from infected mice and sorted by means of FACS.

The plasmid pGFP_OVA (Bumann, 2001a) was digested with BamHI. This digestion removed a 269 bp fragment, containing the $P_{tac}$ promoter, from pGFP_OVA. The remaining 5.1 kb fragment was purified by gel electrophoresis and recircularized, giving rise to plasmid pMW82, having a promoterless GFP variant for detecting strong and medium-strong promoters. Plasmid pMW82 was digested with BamHI and dephosphorylated.

Genomic DNA was isolated from a 5 ml liquid culture of *Salmonella enterica serovar Typhimurium* SL1344. The genomic DNA was partially digested with Sau3a such that the fragments which were formed were in the main in a size range of from 0.5 to 1.5 kb. In addition, genomic fragments in a size range of 500-700 bp were also produced by shearing genomic DNA by ultrasonic. These fragments were treated with DNA polymerase in order to obtain smooth ends.

The genomic fragments and the promoter-free plasmid fragment were ligated under optimal quantity ratios (high number of transformants with few transformants at the same time having double inserts). The ligation preparations were transformed into highly competent *E. coli* (strain XL10, Stratagene) without a restriction system (in order to prevent restriction barriers in regard to the *salmonella*-specific DNA methylation pattern), with this making it possible to achieve a high diversity in the library (>$10^6$). In all, libraries were produced which comprised more than $2 \times 10^5$ independent clones having insert-containing plasmids and which consequently covered more than 99% of the *salmonella* genome. The plasmids were isolated from this library and transformed into *Salmonella enterica serovar Typhimurium* SL1344. In total, $10^6$ transformants were produced in order to keep the diversity of the plasmid library as extensive as possible.

An aliquot of the *salmonella* library having $10^8$ CFU was washed in endotoxin-free PBS and resuspended in PBS to a cell density of $2 \times 10^8$ CFU/ml. 100 µl of this suspension (i.e.

$2\times10^7$ CFU) were injected into the tail veins of 8-12-week-old female BALB/c mice. 16 h after the infection, the mice were anesthetized and killed. The spleen was removed under sterile conditions and comminuted mechanically. The resulting suspension was lyzed with 0.1% Triton x-100 in PBS in order to release intracellular *salmonellas*.

*Salmonellas* having more than 4500 GFP_OVA copies per cell were purified by FACS (FacsSort, B&D or Vantage, B&D) using their typical green and orange emission (2-wavelength method). The detection threshold for this FACS equipment is 500 copies per cell. The detection threshold with the 2-wavelength method when using tissue samples is about 4500 copies/cell, determined by detecting against background. About 0.1-0.3% of all the clones were selected, with this corresponding to expectation (Valdivia and Ramakrishnan, 2000). The fluorescence signal was calibrated with reference samples of differing concentrations by means of a densitometric protein determination in an SDS gel (Coomassie staining).

The 60 000 clones which were obtained were cultivated as a collective in vitro. In a further step, *salmonellas* which expressed fewer than 2000 copies of GFP_OVA during exponential in-vitro growth in LB were isolated. The 75 000 clones which were obtained were highly redundant. They were recultivated as a collective and used for a fresh intravenous infection of mice (identical procedure to that in the first selection round). *Salmonellas* which contained more than 25 000 copies of GFP_OVA per cell after 24 h in the spleen were sorted and recultivated.

Single clones were examined individually for the desired expression properties (in this case: induction in the spleen). Of the 27 clones which have thus far been tested, 17 had a correct GFP_OVA expression. The genomic plasmid insert from correct clones was amplified by means of PCR using the primers "up" 5'-GGCCACGATGCGTC (SEQ ID No. 42) and "down" 5'-TACTCATATGTATATCTCCTTCTTA (SEQ ID No. 43) and typed by being digested with AluI and HpaI.

7 nonredundant inserts (designated 1c, 1f, 2a, 3g, 4a, 10g and 12b, see FIG. 1 and Table 2) were found in these 17 clones. They were partially sequenced using the "down" primer (sequence, see above). The screening method had thus found 7 regulatory sequences which act as strong promoters in the spleen but which show no activity, or only weak activity, in vitro.

Any possible reading frames (i.e. sequences composed of a start codon together with as many subsequent triplets as possible without a stop codon) which might possibly be present within the 7 sequences obtained were identified. This prediction was confirmed by comparison with the sequences from the publicly available NCBI GENBANK database, which is installed on a local blast server. In particular, use was made of the complete *Salmonella enterica serovar typhimurium* LT2 genome sequence (McClelland et al., 2001).

The example could be reworked with the following modifications: instead of AluI and HpaI, it is also possible to use other restriction enzymes which can be employed in the PCR buffer and whose cleavage sites usually occur frequently in the genome, e.g. MspI. If rebuffering is carried out, any restriction enzymes can be used.

Example 3

Optimizing Antigen Expression in *Salmonellas* by Mutating the Shine-Dalgarno Sequence In order to determine the optimal strength of the expression of a foreign antigen in recombinant *salmonella* vaccines, which is on the one hand high enough for a potent immune reaction and on the other hand low enough to be of scarcely any impediment to colonization by the *salmonellas*, the antigen expression achieved by a strong, in-vivo induced promoter was attenuated by using mutated, suboptimal Shine-Dalgarno sequences. These mutants were synthesized by PCR using appropriately selected oligoprimers. The different Shine-Dalgarno sequences were cloned behind the strong in-vivo inducible $P_{pagC}$ promoter and directly upstream of the model antigen GFP_OVA, which carries an ovalbumin T-cell epitope. We tracked, in vivo, the activation of, and blast formation by, the ovalbumin-specific T cells as a measure of the immune reaction in dependence on the expression strength.

Mutated versions of the efficient phage T7 gene 10 Shine-Dalgarno sequence (sequence 5'-TTTAAGAAGGAGATATACAT; SEQ ID No. 44), which, as one of the most efficient sequences known, is most frequently used, were generated by PCR using the primers "mut1, mut2, mut3, mut4 and mut5" (see Table 3) and "mut_down" AGTGACAAGTGTTGGCC (SEQ ID No. 45) and pGO WT (corresponds to $pP_{pagC}$GO, Bumann, 2001b) as the template. Respectively, one base in the 16S RNA-complementary tetranucleotide GGAG, including the adjacent bases, was altered in the mutants. The resulting 214 bp-long fragments were digested with XbaI (cleavage site T|CTAGA) and NcoI (cleavage site C|CATGG) (yields a 191 bp-long fragment) and exchanged for the corresponding fragment in pGO WT. The corresponding plasmids pGO_mut1, pGO_mut2, pGO_mut3, pGO_mut4 and pGO_mut5 were transformed into attenuated *Salmonella enterica serovar typhimurium* aroA SL3261. Female, 8-12-week-old BALB/c mice were transgenically given $4\times10^6$ T cells from Do11.10 mice (Murphy et al., 1990), which are transgenic for a T cell receptor which recognizes a dominant ovalbumin epitope. One day later (=day 0), the mice were immunized orally with $5\times10^8$ CFU of the different *salmonella* strains. The in-vivo expression of GFP_OVA of the individual strains was determined on day 5 by means of 2-wavelength-FACS and using Peyer's patch homogenates. The immunogenicity of the individual strains was determined on day 7 on the basis of the ovalbumin-specific T cell blasts.

Using the six selected sequences as Shine-Dalgarno sequences makes it possible to lower the level of expression from 225 000 copies per cell (under the given conditions, in particular when using the given promoter) down to 3500 copies per cell (approx. 2%) (Table 3). It is consequently possible to cover the entire range which is meaningful for antigen expression. Modifying the Shine-Dalgarno sequences in order to increase expression does not result in any further advantage since the immune response is already saturating in this case.

Selecting from these six sequences is sufficient for reducing the level of expression in a graduated manner over a range of almost 2 powers of ten. Table 3 can be extended by reworking the example with other sequences. In this way, it would be possible to refine the gradation.

The data show that, in the case of GFP_OVA, an expression strength of approx. 75 000 copies per cell (see pGO_mut4) is sufficient to achieve a saturating immune reaction (approx. 40% of the transgenic T cells form blasts on day 7). Since 225 000 copies per cell scarcely cause any impairment of *salmonella* colonization when compared with a strain without plasmid (see Example 1), the concentration which is required for a saturating immune response is in a range which is very well tolerated.

If the properties of the promoter in a given target tissue are known, the GFP_OVA can then be replaced with any other antigen. A selection from the set of the original Shine-Dalgarno sequence and the five mutated sequences (e.g. original sequence, mut1, mut4 and mut5) can be used to rapidly determine, in the case of any arbitrary antigens, the relative level of expression which just elicits a maximum immune reaction by determining the colonization and immune reaction in parallel for corresponding constructs, as described in this example. For this purpose, it is no longer necessary to obtain an absolute determination of the antigen as copies/cell, which means that there is no need for the reporter gene.

Example 4

Other Differentially Regulated Promoters from *Salmonella Enterica Serovar Typhimurium* SL 1344

An aliquot having $10^8$ CFU from a *salmonella* library which was prepared as described in Example 2 was washed in endotoxin-free PBS and resuspended in PBS to a cell density of $2 \times 10^8$ CFU/ml. 100 µl of this suspension (i.e. $2 \times 10^7$ CFU) were injected into the tail veins of 8-12-week-old, female BALB/c mice. 16 h after the infection, the mice were anesthetized and killed. The spleen was removed under sterile conditions and comminuted mechanically. The resulting suspension was lyzed with 0.1% Triton x-100 in PBS in order to release intracellular *salmonellas*.

*Salmonellas* containing more than 4500 GFP_OVA copies per cell were purified by FACS (FacsSort, B&D or Vantage, B&D) using their typical green and orange emission (2-wavelength method). The detection threshold for this FACS equipment is 500 copies per cell. The detection threshold with the 2-wavelength method when using tissue samples is about 4500 copies/cell, determined by detecting against background. About 0.1-0.3% of all the clones were selected, with this corresponding to expectation (Valdivia and Ramakrishnan, 2000).

The 60 000 clones which were obtained were cultivated as a collective in vitro (plate culture in LB medium having an NaCl content which was reduced to 4 g, instead of 10 g, per 1). In a further step, *salmonellas* which expressed fewer than 2000 copies of GFP_OVA during exponential in-vitro growth in LB were isolated. The 75 000 clones which were obtained were highly redundant. They were recultivated as a collective and used for a fresh intravenous infection of mice (identical procedure to that in the first selection round). *Salmonellas* which contained more than 25 000 copies of GFP_OVA per cell after 24 h in the spleen were sorted and recultivated.

In 95 individual clones, the genomic plasmid insert was amplified by PCR using the primers "up" 5'-GGCCACGAT-GCGTC (SEQ ID No. 46) and "down" 5'-TACTCATATG-TATATCTCCTTCTTA (SEQ ID No. 47) and typed by digesting with AluI and HpaI. The 61 nonredundant clones which were identified in this way were examined individually for the desired expression properties (in this case: induction in the spleen), with 58 having a correct GFP_OVA expression (see Table 4).

The inserts in the 58 clones were partially sequenced using the "down" primer (sequence, see above). In this way, the screening method found regulatory sequences which act as strong promoters in the spleen but which exhibit no activity, or only weak activity, in vitro.

Any possible reading frames (i.e. sequences composed of a start codon together with as many subsequent triplets as possible without a stop codon) which might possibly be present within the sequences obtained were identified. This prediction was confirmed by comparison with the sequences from the publicly available NCBI GENBANK database, which is installed on a local blast server. In particular, use was made of the complete *Salmonella enterica serovar typhimurium* LT2 genome sequence (McClelland et al., 2001). The sequences before the start codon (the intergenic regions) were investigated for the presence of putative promoters (transcription starts). The algorithms of Reese (1994), Reese and Eeckman (1995) and Reese et al. (1996) were used for this purpose.

The results for the 58 clones which were obtained are summarized in Table 4 and Table 5. The data are sorted in accordance with the in-vivo/in-vitro expression strength ratio. 13 of the 58 clones satisfy the preferred selection criteria precisely (CLII.4C, CLII.11C, A.11H, A.12A, 2.4A, A.12G, A.9D, A.7A, 3.4F, 3.2E, 3.9A, 3.9E, 3.6B), with the expression strength ratio being at least 12.5, as specified by the selection criteria (25 000/2000); a further six very nearly satisfy the criteria (differences in regard to the in-vitro threshold: A.11B, CLII.9B, CLII.12C, A.2A, 2.1F and 1.3G). In these cases, the expression strength ratio is at least about 8. While the in-vitro threshold was in some cases markedly exceeded in a further five clones (clones A.10F, CLII.3A, 2.2A, 4.5G and A.8H), the expression strength ratio was likewise greater than 8 because the in-vivo expression was correspondingly stronger.

Consequently, a total of 24 of the 58 clones contain *salmonella*-derived regulatory sequences which are able to bring about differential expression of protein in vivo and in vitro with the expression in vivo being at least eight-fold stronger than in vitro. The finding that only five of these 24 clones do not satisfy the preferred selection criteria shows that the method can be carried out successfully with great reliability. Incidentally, clones having strong in-vitro and in-vivo expression are also suitable for producing live vaccines because they are able to induce an improved two-phase immune response.

The regulatory sequences of the genes sifA (clone 3.6B), pipB (clone 3.4F) and aroQ (clone A.2A) were already identified in Example 2 (there, clones 12b, 10g and 1c) but with sequences which differ slightly. The three clones in this example give expression strengths which are markedly greater than those in Example 2. FIGS. 30-32 contain comparisons of the respective sequences. To a large extent, the positions of the intergenic regions, of the putative promoters (insofar as predicted in the two cases) and of the start codons concur. The only difference is that the intergenic region of clone 3.4F and/or of 10g, respectively, appears to contain two putative promoters (in each case, one predicted in each clone). Clones 10g and 12b differ from their homologs 3.4F and 3.6B, which express GFP more strongly, by the presence of a fragment of the autologous gene which is missing in 3.4F and 3.6B. As a result, a fusion protein, which may be folded in a different manner and could consequently be degraded more rapidly, is formed in 10g and 12b. In addition, rare codons may be formed at the fusion site, with these codons in some cases being substantially less well translated, and the residues of the autologous gene may impair translation of the GFP if the two genes are not in the same reading frame since GFP has its own start codon.

A fusion protein is also formed when expression takes place in clones 1c and A.2A, with, however, in the case of 1c containing a markedly larger proportion of the autologous protein, thereby explaining the weaker expression of 1c. For optimal expression, the regulatory sequences should therefore be truncated before the start codon.

The regulatory sequences of the genes pagD (clone 2.4A), phoN (2.2A) and sifB (clone 2.1F), and the sequence of the clone 3G (1.3G), have already been described in Example 2 (there, designated clones 4a, 2a, 1f and 3g).

The other 20 sequences are depicted in FIGS. 10-29.

The 24 regulatory sequences (Table 5, Nos. 35-58) are consequently also suitable for expressing heterologous proteins other than GFP, in particular heterologous antigens, selectively in the spleen. Consequently, these sequences are suitable for producing a live vaccine. The clone which is most suitable is clone 3.6B (sifA), which firstly exhibits very low in-vitro activity and secondly has the highest in-vivo activity.

In a further 5 clones (A.11A, A.8B, CLI.5A, 4.4G and A.1A, depicted in FIGS. 33-37, Table 4, Nos. 18, 19, 20, 28 and 29), the regulatory sequence brings about strong expression in vivo (from 95 000 to 222 000 copies/cell), with this being associated with what is likewise strong expression in vitro (36 000 to 59 000 copies/cell). The in vivo/in vitro expression ratio is at least 2 and at most 6. On account of their strong expression in vivo, these sequences are also suitable for expressing heterologous proteins other than GFP, in particular heterologous antigens, in large quantities in tissues, for example in the spleen. They are consequently likewise suitable for being used in live vaccines.

LEGENDS

FIG. 1:
Diagram of the 7 inserts which were obtained using the method according to the invention and which contain *salmonella*-derived regulatory sequences.

FIG. 2:
Nucleotide sequence of the expression vector pGFP_OVA (SEQ ID No. 3)

FIGS. 3-9:
Nucleotide sequences of the insertions 1c [SEQ ID NO: 4], 1f [SEQ ID NO: 5], 2a [SEQ ID NO: 6], 3g [SEQ ID NO: 7], 4a [SEQ ID NO: 8], 10g [SEQ ID NO: 9] and 12b [SEQ ID NO: 10].

FIGS. 10-29:
Nucleotide sequences of the insertions A.2A [SEQ ID NO: 11], A.7A [SEQ ID NO: 12], A.8H [SEQ ID NO: 13], A.9 [SEQ ID NO: 14], A.10F [SEQ ID NO: 15], A.11B [SEQ ID NO: 16], A.11H [SEQ ID NO: 17], A.12A [SEQ ID NO: 18], A.12G [SEQ ID NO: 19], CLII.3A [SEQ ID NO: 20], CLII.4C [SEQ ID NO: 21], CLII.9B [SEQ ID NO: 22], CLII.11C [SEQ ID NO: 23], CLII.12C [SEQ ID NO: 24], 3.2E [SEQ ID NO: 25], 3.4F [SEQ ID NO: 26], 3.6B [SEQ ID NO: 27], 3.9A [SEQ ID NO: 28], 3.9E [SEQ ID NO: 29] and 4.5G [SEQ ID NO: 30].

FIGS. 30-32:
FIG. 30 shows the comparison of sequence A.2A [upper strand: SEQ ID NO: 11] with sequence 1c [lower strand: SEQ ID NO: 48]. FIG. 31 shows the comparison of sequence 3.4F [upper strand: SEQ ID NO: 49] with sequence 10g [lower strand: SEQ ID NO: 50]. FIG. 32 shows the comparison of sequence 3.6B [upper strand: SEQ ID NO: 51] with sequence 12b [lower strand: SEQ ID NO: 52]. The underlinings mark the intergenic regions while the first base pairs of putative promoters are identified in bold and start codons are marked by a box.

FIGS. 33-37:
Nucleotide sequences of the insertions A.11A [SEQ ID NO: 31], A.8B [SEQ ID NO: 32], CLI.5A [SEQ ID NO: 33], 4.4G [SEQ ID NO: 34] and A1.A [SEQ ID NO: 35].

Table 1

Overview of the expression of reporter proteins (GFP) in *salmonellas* isolated ex vivo (from the Peyer's patches) and the numbers of CFUs isolated.

Table 2

Overview of the regulatory sequences isolated from *salmonella*.

Table 3

Overview of the Shine-Dalgarno sequence mutants [mut1: SEQ ID NO: 37; mut2: SEQ ID NO: 38; mut3: SEQ ID NO: 39; mut4: SEQ ID NO: 40; mut5: SEQ ID NO: 41] employed. Mutations as compared with pGO WT [SEQ ID NO: 36] are identified in bold.

Table 4

The table summarizes the data for 58 clones from Example 4, sorted in accordance with the ratio of in-vivo expression to in-vitro expression.
Column 1: Name of the clone/insert
Column 2: Symbol in accordance with the nomenclature of McClelland et al. (2001)
Column 3: Gene locus corresponding to the nomenclature of McClelland et al. (2001) or www.TIGR.org
Column 4: Function in accordance with the annotation from the nomenclature of McClelland et al. (2001)
Column 5: Species/strain in which the sequence was discovered: STM (*S. typhimurium*), STY (*S. typhi*), SPA (*S. paratyphi* A), SPB (*S. paratyphi* B), SAR (*S. arizonae*), SBO (*S. bongori*), ECO (*E. coli* K12), ECH (*E. coli* O157: H7), KPN (*Klebsiella pneumoniae*)
Column 6: in-vitro expression, given as copies per cell
Column 7: in-vivo expression in the spleen, given as copies per cell
Column 8: in-vivo/in-vitro expression ratio
Column 9: Notes: 1) satisfies the selection criteria precisely; 2) very nearly satisfies the selection criteria.

Table 5

Overview of the properties of the regulatory sequences from Table 4 (see also Table 2) which are most suitable for differential expression.

REFERENCES

1. Andersen, J. B., Sternberg, C., Poulsen, L. K., Bjorn, S. P., Givskov, M. and Molin, S. (1998) New unstable variants of green fluorescent protein for studies of transient gene expression in bacteria Appl. Environ. Microbiol. 64: 2240-2246.
2. Bellamy, R. (1999) The natural resistance-associated macrophage protein and susceptibility to intracellular pathogens Microbes. Infect. 1: 23-27.
3. Beuzon, C. R., Meresse, S., Unsworth, K. E., Ruiz-Albert, J., Garvis, S., Waterman, S. R., Ryder, T. A., Boucrot, E. and Holden, D. W. (2000) *Salmonella* maintains the integrity of its intracellular vacuole through the action of SifA EMBO J. 19: 3235-3249.
4. Beuzon, C. R., Unsworth, K. E. and Holden, D. W. (2001) In vivo Genetic Analysis Indicates that PhoP-PhoQ and the *Salmonella* Pathogenicity Island 2 Type III Secretion System Contribute Independently to *Salmonella enterica* Serovar *Typhimurium* Virulence Infect. Immun. 69: 7254-7261.
5. Bumann, D. (2001a) In vivo visualization of bacterial colonization, antigen expression, and specific T-cell induction following oral administration of live recombinant *Salmonella enterica* serovar *Typhimurium* Infect. Immun. 69: 4618-4626.
6. Bumann, D. (2001b) Regulated Antigen Expression in Live Recombinant *Salmonella enterica Serovar Typhimurium* Strongly Affects Colonization Capabilities and Specific CD4(+)-T-Cell Responses Infect. Immun. 69: 7493-7500.
7. Burns-Keliher, L., Nickerson, C. A., Morrow, B. J. and Curtiss, R. (1998) Cell-specific proteins synthesized by *Salmonella typhimurium* Infect. Immun. 66: 856-861.
8. Calhoun, D. H., Bonner, C. A., Gu, W., Xie, G. and Jensen, R. A. (2001) The emerging periplasm-localized subclass of AroQ chorismate mutases, exemplified by those from *Salmonella typhimurium* and *Pseudomonas aeruginosa* Genome Biol. 2: 1-16.
9. Contag, C. H., Contag, P. R., Mullins, J. I., Spilman, S. D., Stevenson, D. K. and Benaron, D. A. (1995) Photonic detection of bacterial pathogens in living hosts Mol Microbiol 18: 593-603.
10. Cormack, B. P., Valdivia, R. H. and Falkow, S. (1996) FACS-optimized mutants of the green fluorescent protein (GFP) Gene 173: 33-38.
11. Cotter, P. A., DiRita, V. J. (2000) BACTERIAL VIRULENCE GENE REGULATION: An evolutionary perspective Annu. Rev. Microbiol. 54: 519-565.
12. Diehn, M., Relman D. A. (2001) Comparing functional genomic datasets: lessons from DNA microarray analyses of host-pathogen interactions. Curr. Opin Microbiol. 4: 95-101)
13. Dunstan, S. J., Simmons, C. P. and Strugnell, R. A. (1999) Use of in vivo regulated promoters to deliver antigens from attenuated *Salmonella enterica* var. *Typhimurium* Infect. Immun. 67: 5133-5141.
14. Goerke, C., Bayer, M. G. and Wolz, C. (2001) Quantification of bacterial transcripts during infection using competitive reverse transcription-PCR (RT-PCR) and LightCycler RT-PCR Clin. Diagn. Lab Immunol. 8: 279-282.
15. Goerke, C., Campana, S., Bayer, M. G., Doring, G., Botzenhart, K. and Wolz, C. (2000) Direct quantitative transcript analysis of the agr regulon of *Staphylococcus aureus* during human infection in comparison to the expression profile in vitro. Infect. Immun. 68: 1304-1311.
16. Gort, A. S., Miller, V. L. (2000) Identification and characterization of *Yersinia enterocolitica* genes induced during systemic infection Infect. Immun. 68: 6633-6642.
17. Groisman, E. A., Ochman, H. (1997) How *Salmonella* became a pathogen Trends Microbiol. 5: 343-349.
18. Gunn, J. S., Alpuche-Aranda, C. M., Loomis, W. P., Belden, W. J. and Miller, S. I. (1995) Characterization of the *Salmonella typhimurium* pagC/pagD chromosomal region J. Bacteriol. 177: 5040-5047.
19. Hensel, M. (1998) Whole genome scan for habitat-specific genes by signature-tagged mutagenesis Electrophoresis 19: 608-612.
20. Hopkins, S. A., Niedergang, F., Corthesy-Theulaz, I. E. and Kraehenbuhl, J. P. (2000) A recombinant *Salmonella typhimurium* vaccine strain is taken up and survives within murine Peyer's patch dendritic cells. Cell. Microbiol. 2: 59-68
21. Hoiseth and Stocker (1981) Nature 291: 238-239
22. Jacobi, C. A., Roggenkamp, A., Rakin, A., Zumbihl, R., Leitritz, L. and Heesemann, J. (1998) In vitro and in vivo expression studies of yopE from *Yersinia enterocolitica* using the gfp reporter gene Mol. Microbiol. 30: 865-882.
23. Jouanguy, E., Doffinger, R., Dupuis, S., Pallier, A., Altare, F. and Casanova, J. L. (1999) IL-12 and IFN-gamma in host defense against mycobacteria and *Salmonella* in mice and men Curr. Opin. Immunol. 11: 346-351.
24. Keiler, K. C., Sauer, R. T. (1996) Sequence determinants of C-terminal substrate recognition by the Tsp protease. J. Biol. Chem. 271: 2589-93.
25. Lee, S. H., Butler, S. M. and Camilli, A. (2001) Selection for in vivo regulators of bacterial virulence Proc. Natl. Acad. Sci. USA 98: 6889-6894.
26. Lee, S. H., Camilli, A. (2000) Novel approaches to monitor bacterial gene expression in infected tissue and host Curr. Opin. Microbiol 3: 97-101.
27. Lee, S. H., Hava, D. L., Waldor, M. K. and Camilli, A. (1999) Regulation and temporal expression patterns of *Vibrio cholerae virulence* genes during infection Cell 99: 625-634.
28. Mahan, M. J., Heithoff, D. M., Sinsheimer, R. L. and Low, D. A. (2000) ASSESSMENT OF BACTERIAL PATHOGENESIS BY ANALYSIS OF GENE EXPRESSION IN THE HOST Annu. Rev. Genet. 34: 139-164.
29. McClelland, M., Sanderson, K. E., Spieth, J., Clifton, S. W., Latreille, P., Courtney, L., Porwollik, S., Ali, J., Dante, M., Du, F., Hou, S., Layman, D., Leonard, S., Nguyen, C., Scott, K., Holmes, A., Grewal, N., Mulvaney, E., Ryan, E., Sun, H., Florea, L., Miller, W., Stoneking, T., Nhan, M., Waterston, R. and Wilson, R. K. (2001) Complete genome sequence of *Salmonella enterica serovar Typhimurium* LT2 Nature 413: 852-856.
30. Miao, E. A., Miller, S. I. (2000) A conserved amino acid sequence directing intracellular type III secretion by *Salmonella typhimurium* Proc. Natl. Acad. Sci. USA 97: 7539-7544.
31. Miller, S. I., Kukral, A. M. and Mekalanos, J. J. (1989) A two-component regulatory system (phoP phoQ) controls *Salmonella typhimurium* virulence Proc. Natl. Acad. Sci. USA 86: 5054-5058.
32. Pfeifer, C. G., Marcus, S. L., Steele-Mortimer, O., Knodler, L. A. and Finlay, B. B. (1999) *Salmonella typhimurium* virulence genes are induced upon bacterial invasion into phagocytic and nonphagocytic cells Infect. Immun. 67: 5690-5698.
33. Reese, M. G. (1994) Degree dissertation, Deutsches Krebsforschungszentrum [German Center for Cancer Research], Heidelberg.
34. Reese, M. G. and Eeckman, F. H. (1995) Novel Neural Network Algorithms for Improved Eukaryotic Promoter Site Recognition, The Seventh International Genome Sequencing and Analysis Conference, Hilton Head Island, South Carolina.
35. Reese, M. G., Harris, N. L. and Eeckman, F. H. (1996) Large Scale Sequencing Specific Neural Networks for Promoter and Splice Site Recognition, Biocomputing: Proceedings of the 1996 Pacific Symposium edited by Lawrence Hunter and Terri E. Klein, World Scientific Publishing Co, Singapore, 1996, Jan. 2-7, 1996.
36. Richter-Dahlfors, A., Buchan, A. M. J. and Finlay, B. B. (1997) Murine salmonellosis studied by confocal microscopy: *Salmonella typhimurium* resides intracellularly inside macrophages and exerts a cytotoxic effect on phagocytes in vivo J. Exp. Med. 186: 569-580.
37. Rokbi, B., Seguin, D., Guy, B., Mazarin, V., Vidor, E., Mion, F., Cadoz, M. and Quentin-Millet, M. J. (2001) Assessment of Helicobacter pylori Gene Expression within Mouse and Human Gastric Mucosae by Real-Time Reverse Transcriptase PCR Infect. Immun. 69: 4759-4766.

38. Salcedo, S. P., Noursadeghi, M., Cohen, J. and Holden, D. W. (2001) Intracellular replication of *Salmonella typhimurium* strains in specific subsets of splenic macrophages in vivo Cell Microbiol. 3: 587-597.
39. Schubert, S., Rakin, A., Fischer, D., Sorsa, J. and Heesemann, J. (1999) Characterization of the integration site of *Yersinia* high-pathogenicity island in *Escherichia coli* FEMS Microbiol. Lett. 179: 409-414.
40. Slauch, J. M., Mahan, M. J. and Mekalanos, J. J. (1994) Measurement of transcriptional activity in pathogenic bacteria recovered directly from infected host tissue Biotechniques 16: 641-644.
41. Valdivia, R. H., Falkow, S. (1997) Fluorescence-based isolation of bacterial genes expressed within host cells Science 277: 2007-2011.
42. Valdivia, R. H., Ramakrishnan, L. (2000) Applications of gene fusions to green fluorescent protein and flow cytometry to the study of bacterial gene expression in host cells Methods Enzymol. 326: 47-73.
43. Wilmes-Risenberg, M. R., Foster, J. W. and Curtiss, R., III (1997) An altered rpoS allele contributes to the avirulence of *Salmonella typhimurium* LT2 Infect. Immun. 65: 203-210.
44. Yarchuk, O., Jacques, N., Guillerez, J., Dreyfus, M. (1992) Interdependence of translation, transcription and mRNA degradation in the lacZ gene. J. Mol. Biol. 226: 581-96.
45. Yrlid, U., Svensson, M., Hakansson, A., Chambers, B. J., Ljunggren, H. G. and Wick, M. J. (2001) In vivo activation of dendritic cells and T cells during *Salmonella enterica* serovar Typhimurium infection Infect. Immun. 69: 5726-5735.

TABLE 1

| Construct | CFU (±standard deviation) | % CFU control | Expression of GFP (±standard deviation) |
|---|---|---|---|
| $P_{pagC}$-GFP.mut3 | 400 ± 300 | <1 | 2,000,000 ± 200,000 |
| $P_{pagC}$-GFP_OVA | 90,000 ± 30,000 | 86 | 237,000 ± 30,000 |
| $P_{pagC}$-GFP_ASV | 25,000 ± 10,000 | 24 | 385,000 ± 40,000 |
| $P_{pagC}$-GFP_LVA | 80,000 ± 20,000 | 76 | 179,000 ± 20,000 |
| $P_{spvA}$-GFP.mut3 | 90,000 ± 30,000 | 86 | 56,000 ± 6000 |
| $P_{spvA}$-GFP_OVA | 100,000 ± 30,000 | 95 | <4000 (too low) |
| $P_{spvA}$-GFP_ASV | 120,000 ± 30,000 | 114 | <4000 (too low) |
| Control SL1344 | 105,000 ± 30,000 | 100 | None |

TABLE 2

| Clone | Insert[a] (size) | Expression of GFP (copies/cell) in vitro | in vivo | Proximal ORF[b] (start codon) | Intergenic region[b] | Putative promoters[b] (transcription start) |
|---|---|---|---|---|---|---|
| 1c | 800 bp | 1500 | 16,000 | bp 289 | bp 207-288 | bp 162* |
| 1f | 564 bp | 1800 | 230,000 | bp 595[c] | whole insert | bp 271 |
| 2a | 640 bp | 3300 | 48,000 | bp 298 | bp 1-297 | bp 255 |
| 3g | 1.0 kb | 3300 | 225,000 | bp 750 | bp 573-749 | bp 736 |
| 4a | 640 bp | 1300 | 28,000 | bp 466 | bp 417-465 | bp 422 |
| 10g | 1.6 kb | 1200 | 38,000 | bp 431 | bp 214-430 | bp 400 |
| 12b | 1.2 kb | 800 | 15,000 | bp 468 | bp 134-467 | bp 384 |

*This promoter is not located in the intergenic region;
[a]size estimated on the basis of PCR products apart from in the case of 1f, for which the complete sequence is available;
[b]bp positions refer to the previously known partial sequence of the insert as given in the annex;
[c]start codon of sifB is located 31 bp downstream of the end of the insert.

TABLE 3

| Plasmid | Sequence in the region of the Shine-Dalgarno sequence (primer) | in-vivo expression copies per cell | % | T cell blasts % |
|---|---|---|---|---|
| pGO_WT | GCTCTAGATTTAAGAAGGAGATATACATATG | 225,000 ± 12,000 | 100 | 40 ± 5 |
| pGO_mut1 | GCTCTAGATTTAAGAAAGAGATATACATATG | 33,000 ± 12,000 | 15 | 22 ± 5 |
| pGO_mut2 | GCTCTAGATTTAAGAAGCAGATATACATATG | 3500 ± 12,000[1] | 2[1] | 16 ± 5 |
| pGO_mut3 | GCTCTAGATTTAAGAGGGAGATATACATATG | 103,000 ± 12,000 | 46 | 39 ± 5 |
| pGO_mut4 | GCTCTAGATTTAAGAAGGGGATATACATATG | 78,000 ± 12,000 | 35 | 41 ± 5 |
| pGO_mut5 | GCTCTAGATTTAAGAAGGAAATATACATATG | 125,000 ± 12,000 | 56 | 42 ± 5 |

[1]: measured values below the in-vivo detection limit; values are based on estimates made with the aid of in-vitro data.

TABLE 4

| Clone | Symbol | Locus | Function | Species | in-vitro expr. | Spleen | in vivo/ in vitro | Notes |
|---|---|---|---|---|---|---|---|---|
| 10.9B | smpA | STM2685 | small membrane protein A | all nine genomes | 288,000 | 51,000 | 0.18 | |
| 4.1A | mgtA | STM4456 | P-type ATPase, Mg2+ ATPase transporter | all nine genomes | 316,000 | 58,000 | 0.18 | |

TABLE 4-continued

| Clone | Symbol | Locus | Function | Species | in-vitro expr. | Spleen | in vivo/ in vitro | Notes |
|---|---|---|---|---|---|---|---|---|
| 10.1B | STM2329 | STM2329 | putative cytoplasmic protein | STM and STY | 167,000 | 40,000 | 0.24 | |
| 10.1A | rsd | STM4165 | regulator of sigma D, shows activity in binding to the large RNA polymerase subunit | all nine genomes | 143,000 | 37,000 | 0.26 | |
| 10.6A | crp | STM3466 | catabolite activator protein (CAP), cAMP receptor protein (CRP family) | all nine genomes | 110,000 | 29,000 | 0.26 | |
| A.7D | rfc | STM1332 | O-antigen polymerase | STM, STY, SPA and SPB | 100,000 | 29,000 | 0.29 | |
| 4.4A | ytfL | STM4407 | putative hemolysin-like protein | all nine genomes | 527,000 | 171,000 | 0.32 | |
| 4.7C | ribB | STM3195 | 3,4-dihydroxy-2-butanone-4-phosphate synthase | all nine genomes | 220,000 | 74,000 | 0.34 | |
| 4.8H | stm4065 | STM4065 | putative permease from the Na+:galactoside symporter family | STM, STY, SPA and SPB | 276,000 | 123,000 | 0.45 | |
| 10.7A | nmpC | STM1572 | new outer membrane protein, bacterial porin (predicted) | STM, SPA, SPB, SAR and SBO | 68,000 | 34,000 | 0.50 | |
| 4.1B | tpx | STM1682 | thiol peroxidase | all nine genomes | 250,000 | 166,000 | 0.66 | |
| CLII.5C | araC | STM0104 | transcription regulator (AraC/XylS family) for ara operon | all nine genomes | 45,000 | 33,000 | 0.73 | |
| A.2G | hilD | STM2875 | regulatory helix-turn-helix protein, araC family | all *salmonellas* | 45,000 | 33,000 | 0.73 | |
| A.8D | ybaJ | STM0474 | putative cytoplasmic protein | all nine genomes | 27,000 | 20,000 | 0.74 | |
| CLII.2B | yeiU | STM2213 | putative permease | all nine genomes | 47,000 | 40,000 | 0.85 | |
| 10.12A | rpoE | STM2640 | sigma E (sigma 24) factor of RNA polymerase, responds to periplasmic stress | all nine genomes | 134,000 | 121,000 | 0.90 | |
| A.3H | pheA | STM2667 | bifunctional: chorismate mutase P; prephenate dehydratase | all nine genomes | 45,000 | 46,000 | 1.02 | |
| A.1A | stm1672 | stm1672 | putative cytoplasmic protein | STM, STY, SPA and SPB | 47,000 | 95,000 | 2.02 | |
| A.8B | STM4157 | STM4157 | putative cytoplasmic protein | STM, SPB and SAR | 45,000 | 124,000 | 2.76 | |
| 4.4G | yejG | STM2220 | putative cytoplasmic protein | all nine genomes | 59,000 | 163,000 | 2.76 | |
| A.11C | stm1633 | stm1633 | putative periplasmic binding protein | STM, STY, SPB and SBO | 16,000 | 44,000 | 2.75 | |
| CLII.8C | mdoB | STM4541 | phosphoglycerol transferase I | all nine genomes | 8500 | 25,000 | 2.94 | |
| A.4H | NT01ST0833 | NT01ST0833 (only TIGR) | | STM | 12,000 | 41,000 | 3.42 | |
| CLII.1B | phoB | STM0397 | response regulator in 2-component regulation system together with PhoR, regulates pho (phosphate) regulon | all nine genomes | 14,000 | 50,000 | 3.57 | |
| A.7H | phoP | STM1231 | response regulator in 2-component regulation system together with PhoQ, transcribed genes which are expressed at low Mg++ concentration | all nine genomes | 12,000 | 42,000 | 3.50 | |
| CLII.7B | marC | STM1521 | putative MarC transporter, multiple antibiotic-resistance protein | all nine genomes | 7500 | 31,000 | 4.13 | |
| A.3D | STM1583 | STM1583 | putative cytoplasmic protein | STM, STY, SPA, SPB and SBO | 7300 | 31,000 | 4.25 | |
| A.11A | ugd | STM2080 | UDP-glucose/GDP-mannose dehydrogenase | all nine genomes | 36,000 | 164,000 | 4.56 | |

TABLE 4-continued

| Clone | Symbol | Locus | Function | Species | in-vitro expr. | Spleen | in vivo/ in vitro | Notes |
|---|---|---|---|---|---|---|---|---|
| CLI.5A | mig14 | STM2782 | putative transcription activator, polymixin | STM, STY, SPA, SPB and SAR | 37,000 | 222,000 | 6.00 | |
| A.8C | rna | STM0617 | RNase I, upregulation during stress probably represents a mechanism for rapidly converting cellular mRNA as a response to new surroundings | all nine genomes | 6700 | 47,000 | 7.01 | |
| CLII.5A | ugtL | STM1601 | putative membrane protein: homology with *Schizosaccharomyces* chitinase, possibly involved in peptidoglycan metabolism | STM, STY, SPA and SPB | 13,000 | 93,000 | 7.15 | |
| CLII.4A | yaoF | STM1275 | putative hemolysin | all *salmonellas* | 4200 | 30,000 | 7.14 | |
| CLII.9C | prpA = PSTK | STM1853 | serine/threonine protein phosphatase | all *salmonellas* | 4700 | 37,000 | 7.87 | |
| A.9E | PSLT046 | PSLT046 | putative carboanhydrase | STM | 8,200 | 65,000 | 7.93 | |
| A.11B | slyA | STM1444 | transcription regulator for hemolysin (MarR family) | all nine genomes | 2900 | 23,000 | 7.93 | 2) |
| A.10F | STM2780 | STM2780 | homolog of pipB, putative pentapeptide repeat (8 copies) | STM, STY, SPA and SPB | 3100 | 26,000 | 8.39 | |
| CLII.3A | stm1630 | stm1630 | putative inner membrane protein | STM, SPB and SAR | 12,000 | 113,000 | 9.42 | |
| CLII.9B | stm1637 | stm1637 | putative inner membrane protein | STM, STY and SPB | 2400 | 24,000 | 10.00 | 2) |
| CLII.12C | STM0859 | STM0859 | putative transcription regulator, LysR family | STM, SPB and SAR | 2100 | 22,000 | 10.48 | 2) |
| 2.2A | phoN | STM4319 | nonspecific acid phosphatase | STM, STY, SPA and SPB | 8000 | 91,000 | 11.38 | |
| CLII.4C | ssaM | STM1413 | from the secretion system apparatus, essential for virulence | all *salmonellas* | 1700 | 25,000 | 14.71 | 1) |
| CLII.11C | sseJ | STM1631 | secreted effector protein of the SPI2 secretion system, necessary for full virulence | STM, SPB and SAR | 1500 | 26,000 | 17.33 | 1) |
| A.11H | STM0809 | STM0809 | putative inner membrane protein | STM and SPB | 1500 | 28,000 | 18.67 | 1) |
| 4.5G | NT01ST5267 | NT01ST5267 (only TIGR) | | STM | 42,000 | 841,000 | 20.02 | |
| A.12A | STM2585A | STM2585A | pagK homolog on Gifsy-1 prophages | STM, SPB and SAR | 1700 | 34,000 | 20.00 | 1) |
| A.2A | aroQ | STM1269 | putative chorismate mutase | all *salmonellas* | 2500 | 60,000 | 24.00 | 2) |
| 2.4A | PagD | STM1244 | PhoP-regulated | all *salmonellas* | 1700 | 41,000 | 24.12 | 1) |
| A.12G | STM0972 | STM0972 | homolog to secreted protein sopD | STM, STY, SPA and SPB | 1600 | 47,000 | 29.38 | 1) |
| A.8H | virK | STM2781 | virulence gene, homologous sequence to virK in *Shigella* | all *salmonellas* | 17,000 | 532,000 | 31.29 | |
| A.9D | ssaB | STM1393 | from the secretion system apparatus | all *salmonellas* | 1400 | 92,000 | 65.71 | 1) |
| A.7A | sseA | STM1397 | secretion system effector, essential for virulence | STM, STY, SPA and SPB | 1800 | 132,000 | 73.33 | 1) |
| 3.4F | pipB | STM1088 | encoded on the pathogenicity island: SPI3, SPI2 effector | all *salmonellas* | 1400 | 139,000 | 99.29 | 1) |
| 3.2E | iicA | STM4504 | putative cytoplasmic protein, is induced intracellularly in cell culture, not essential for virulence | all *salmonellas* | 1600 | 187,000 | 116.88 | 1) |

TABLE 4-continued

| Clone | Symbol | Locus | Function | Species | in-vitro expr. | Spleen | in vivo/ in vitro | Notes |
|---|---|---|---|---|---|---|---|---|
| 3.9A | yjiS | STM4521 | putative cytoplasmic protein | all salmonellas | 1500 | 261,000 | 174.00 | 1) |
| 2.1F | sifB | STM1602 | secreted effector protein of SPI2 secretion system, not essential for virulence | STM, STY, SPA and SPB | 2600 | 473,000 | 181.92 | 2) |
| 1.3G | 3G | not in LT2 genome | | Salmonella enterica serovar Dublin | 2200 | 413,000 | 187.73 | 2) |
| 3.9E | ssaG | STM1406 | from the secretion system apparatus, essential for virulence | all salmonellas | 1700 | 508,000 | 298.82 | 1) |
| 3.6B | sifA | STM1224 | secreted effector protein of SPI2 secretion system, not essential for virulence; replication in macrophages | STM, STY, SPA and SPB | 1500 | 666,000 | 444.00 | 1) |

TABLE 5

| Clone | Insert[a] | Intergenic region[b] | Putative promoter[b] (transcription start) | Proximal ORF (start codon)[b] |
|---|---|---|---|---|
| A.2A | 600 | 149-232 | no prediction | 233 |
| A.7A | 444 | 132-395 | 148 | 396 |
| A.8H | 461 | 1-249 | 45 | 250 |
| A.9D | 585 | 1-219 | 135 | 220 |
| A.10F | 609 | 1-268 | 121 | 269 |
| A.11B | 591 | 588-591 | no prediction | 783[c] |
| A.11H | 559 | no intergenic region | 463 | 653 |
| A.12A | 525 | 1-291 | 191 or 229 | 292 |
| A.12G | 604 | 256-387 | 309 | 388 |
| CLII.3A | 235 | 1-235 | 114 | 236 |
| CLII.4C | 386 | 118-176 | no prediction | 177 |
| CLII.9B | 543 | 405-542 | 465 | 543 |
| CLII.11C | 509 | 1-57 | no prediction | 58 |
| CLII.12C | 704 | 413-677 | no prediction | 678 |
| 3.2E | 658 | 331-607 | 473 | 608 |
| 3.4F | 628 | 465-628 | 485 | 683[c] |
| 3.6B | 875 | 567-875 | 817 | 896[c] |
| 3.9A | 405 | 196-401 | 268 | 402 |
| 3.9E | 691 | 445-539 | 526 | 540 |
| 4.5G | 594 | 487-594 | 504 | 641[c] |
| A.11A | 551 | 350-551 | 512 | 586[c] |
| A.8B | 529 | 1-135 | 94 | 136 |
| CLI.5A | 449 | 1-202 | 176 | 203 (GTG) |
| 4.4G | 566 | 212-566 | 445 | 603[c] |
| A.1A | 518 | 1-324 | 294 | 325 |

[a]length of the inserts in base pairs (bp), estimated on the basis of PCR products in the case of clone A.2A;
[b]positions refer to the partial sequences shown in FIG. 10-29 and 33-37;
[c]the start codon is located downstream of the end of the insert and was deduced from the sequences published in McClelland et al. (2001) and TIGR.

The invention claimed is:

1. A promoter which is contained in the insertion 4.5G, 3G or in a partial sequence thereof having a length of at least 40 nucleotides.

2. The promoter of claim 1 which is contained in insertion 4.5G or in a partial sequence thereof having a length of at least 40 nucleotides.

3. The promoter of claim 1, in operative linkage with a nucleic acid sequence which is heterologous with respect thereto.

4. A method of producing a live vaccine comprising inserting a promoter according to claim 1 into an expression vector, transforming host bacteria with said vector wherein said host bacteria express a nucleic acid sequence, and isolating said host bacteria for use as a live vaccine.

5. A method of expressing recombinant antigens comprising inserting a promoter according to claim 1 into a vector which contains a nucleic acid sequence, and expressing the nucleic acid sequence to produce a recombinant antigen.

6. The method of claim 5 further comprising inserting the nucleic acid which encodes the recombinant antigen into the genome of a host cell.

7. The method of claim 6 wherein the nucleic acid which encodes the recombinant antigen is introduced into a host cell using an expression vector.

8. A nucleic acid which consists essentially of a sequence selected from insertion 4.5G, insertion 3G, or a partial sequence of said nucleic acid having a length of at least 40 nucleotides.

9. A nucleic acid, which contains a sequence which is selected from insertions 4.5G, 3G, or a partial sequence of said nucleic acid having a length of at least 40 nucleotides.

10. The nucleic acid of claim 9, wherein said partial sequence has a length of at least 40, and up to 200 nucleotides.

11. The nucleic acid of claim 9, which comprises insertions commencing 200 bp before the beginning of the putative promoter of 4.5G or 3G and up to the proximal start codon of 4.5G or 3G or a partial sequence of said nucleic acid having a length of at least 40 nucleotides.

12. The nucleic acid of claim 11, which comprises the partial sequences of the insertions commencing 150 bp before the beginning of the putative promoter of 4.5G or 3G and up to the proximal start codon of 4.5G or 3G or a partial sequence of said nucleic acid having a length of at least 40 nucleotides.

13. The nucleic acid of claim 12, which comprises the partial sequences of the insertions commencing 100 bp before the beginning of the putative promoter according to Table 2 and/or 5 and up to the proximal start codon according to Table 2 and/or 5, or a partial sequence of said nucleic acid having a length of at least 40 nucleotides.

14. The nucleic acid of claim 13, which comprises the partial sequences of the insertions commencing 50 bp before the beginning of the putative promoter according to Table 2 and/or 5 and up to the proximal start codon according to Table 2 and/or 5, or a partial sequence of said nucleic acid having a length of at least 40 nucleotides.

15. The nucleic acid of claim 14, which comprises the partial sequences of the insertions commencing 40 bp before the beginning of the putative promoter according to Table 2 and/or 5 and up to the proximal start codon according to Table 2 and/or 5, or a partial sequence of said nucleic acid having a length of at least 40 nucleotides.

16. A recombinant bacterium, that contains a promoter of claim 1 in operative linkage with a nucleic acid sequence which is heterologous with respect thereto.

17. The bacterium of claim 16, wherein the transcription start of the heterologous nucleic acid sequence directly follows the promoter.

18. The bacterium of claim 16, wherein the nucleic acid sequence encodes a recombinant antigen.

19. An immunogenic composition that contains a bacterium of claim 18 and optionally contains pharmaceutically customary carrier substances or auxiliary substances.

20. The immunogenic composition of claim 19, wherein the bacterium is selected from the group consisting of *Salmonella typhimurium, S. typhi, S. paratyphi* A and *S. paratyphi* B, and the promoter is autologous with respect to the bacterium.

21. The promoter of claim 1 which is contained in insertion 3G or a partial sequence thereof having a length of at least 40 nucleotides.

22. The promoter of claim 1 which has an in vivo/in vitro expression ratio of at least about 8.

* * * * *